United States Patent
Eastham et al.

(10) Patent No.: US 10,704,063 B2
(45) Date of Patent: *Jul. 7, 2020

(54) PROCESS FOR THE BIOLOGICAL PRODUCTION OF METHACRYLIC ACID AND DERIVATIVES THEREOF

(71) Applicant: LUCITE INTERNATIONAL UK LIMITED, Billingham (GB)

(72) Inventors: Graham Ronald Eastham, Redcar (GB); Gill Stephens, Nottingham (GB); Andrew Yiakoumetti, Nottingham (GB)

(73) Assignee: LUCITE INTERNATIONAL UK LIMITED, Billingham (GB)

( * ) Notice: Subject to any disclaimer, the term of this patent is extended or adjusted under 35 U.S.C. 154(b) by 118 days.

This patent is subject to a terminal disclaimer.

(21) Appl. No.: 15/574,961

(22) PCT Filed: May 18, 2016

(86) PCT No.: PCT/GB2016/051438
§ 371 (c)(1),
(2) Date: Nov. 17, 2017

(87) PCT Pub. No.: WO2016/185211
PCT Pub. Date: Nov. 24, 2016

(65) Prior Publication Data
US 2018/0171368 A1 Jun. 21, 2018

(30) Foreign Application Priority Data
May 19, 2015 (GB) .................................. 1508582.2

(51) Int. Cl.
| | |
|---|---|
| *C12P 7/40* | (2006.01) |
| *C12N 9/00* | (2006.01) |
| *C12N 9/16* | (2006.01) |
| *C12P 7/62* | (2006.01) |
| *C12P 5/02* | (2006.01) |
| *C07C 67/00* | (2006.01) |
| *C08F 120/06* | (2006.01) |
| *C08F 120/14* | (2006.01) |
| *C12N 9/10* | (2006.01) |
| *C12N 9/02* | (2006.01) |

(52) U.S. Cl.
CPC ............... *C12P 7/40* (2013.01); *C07C 67/00* (2013.01); *C08F 120/06* (2013.01); *C08F 120/14* (2013.01); *C12N 9/001* (2013.01); *C12N 9/1029* (2013.01); *C12N 9/16* (2013.01); *C12P 5/026* (2013.01); *C12P 7/62* (2013.01); *C12Y 103/03006* (2013.01); *C12Y 203/01084* (2013.01); *C12Y 301/02023* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 6,268,521 B1 | 7/2001 | Burghard | |
| 2003/0175912 A1 | 9/2003 | Suga | |
| 2013/0065279 A1* | 3/2013 | Burk | C12P 19/32 |
| | | | 435/88 |

FOREIGN PATENT DOCUMENTS

| | | | |
|---|---|---|---|
| EP | 1697525 | A2 | 9/2006 |
| EP | 2848694 | A1 | 3/2015 |
| JP | 57-134500 | A | 8/1982 |
| JP | 57-183799 | A | 11/1982 |
| JP | 58-35197 | A | 3/1983 |
| JP | 58-67699 | A | 4/1983 |
| JP | 58-77895 | A | 5/1983 |
| JP | 58-192900 | A | 11/1983 |
| JP | 5-7491 | A | 1/1993 |
| JP | 2000-143795 | A | 5/2000 |
| JP | 2000-262288 | A | 9/2000 |
| WO | 99/03988 | | 1/1999 |
| WO | 200018935 | A1 | 4/2000 |
| WO | 2005010175 | A1 | 4/2000 |
| WO | 2006028063 | A1 | 3/2006 |
| WO | 2012/069813 | A1 | 5/2012 |
| WO | 2012/109534 | A2 | 8/2012 |
| WO | 2013044076 | A1 | 3/2013 |
| WO | 2014/038214 | A1 | 3/2014 |
| WO | 201438216 | A1 | 3/2014 |
| WO | 2014062556 | A2 | 4/2014 |
| WO | 2015031653 | A2 | 3/2015 |

OTHER PUBLICATIONS

De Bellis et al., "Purification and Characterization of a Novel Pumpkin Short-Chain Acyl-Coenzyme A Oxidase with Structural Similarity to Acyl-Coenzyme A Dehydrogenases", Plant Physiology, May 2000, vol. 123, pp. 327-334.*

Datsenko, K. A. et al., "One-step inactivation of chromosomal genes in *Escherichia coli* K-12 using PCR products," Jul. 2000, Proc. Natl. Acad. Sci. 97:6640-6645 (Abstract only).

Hoffmeister et al., "Mitochondrial trans-2-Enoyl-CoA Reductase of Wax Ester Fermentation from Euglena gracilis Defines a New Family of Enzymes Involved in Lipids," J. Biol. Chem., 280:4329-4338 (2005) (Abstract only).

(Continued)

*Primary Examiner* — Suzanne M Noakes
(74) *Attorney, Agent, or Firm* — Shumaker, Loop & Kendrick, LLP

(57) ABSTRACT

A process of producing methacrylic acid and/or derivatives thereof including the following steps: (a) biologically converting isobutyryl-CoA into methacrylyl-CoA by the action of an oxidase; and (b) converting methacrylyl-CoA into methacrylic acid and/or derivatives thereof. The invention also extends to microorganisms adapted to conduct the steps of the process.

17 Claims, 12 Drawing Sheets

Specification includes a Sequence Listing.

(56) References Cited

OTHER PUBLICATIONS

Cho, E. H. et al., "Interactions between Integrase and Excisionase in the Phage Lambda Excisive Nucleoprotein Complex," Sep. 2002, J. Bacteriol., vol. 184, No. 18, 5200-5203 (Abstract only).
Sayali, Kulkarni et al., "Microbial Esterases: An overview," Int.J. Curr.Microbiol.App.Sci (2013) 2(7): 135-146.
Zhang et al., "Cells and method for producing isobutyric acid," A. P. 2012 (Abstract only).
International Search Report for PCT/GB2016/051438 dated Jul. 26, 2016 (4 pages).
Database EPO Proteins [online]; Sep. 10, 2014, "Sequencel from Patent WO2014062556", XP002759988, Database acession No. JC537169 (1 page).
Hayashi Hiroshi et al; "A Novel Acyl-CoA Oxidase That Can Oxidize Short-chain Acyl-CoA in Plant Peroxisomes", Journal of Biological Chemistry, American Society for Biochemistry and Molecular Biology, Apr. 30, 1999, US, vol. 274, No. 18, (7 pages).
Database UniProt [Online]; Nov. 2, 2010 RecName: Full=4-dyroxybenzoyl-CoA thioesterase, retrieved from EBI accession No. UNIPROT:QO4416 (2 pages).
Non-Final Office Action for U.S. Appl. No. 15/817,493 dated Nov. 20, 2019 (20 pages).

\* cited by examiner

PROCESS FOR THE BIOLOGICAL PRODUCTION OF METHACRYLIC ACID AND DERIVATIVES THEREOF

FIELD

The present invention relates to a process for the biological production of methacrylic acid and derivatives thereof. In particular the process relates to using particular enzymatic conversions to form methacrylic acid from isobutyryl-CoA via methacrylyl-CoA, and the polymers or copolymers produced therefrom.

BACKGROUND

Acrylic acids and their alkyl esters, in particular methacrylic acid (MAA) and its methyl ester, methyl methacrylate (MMA), are important monomers in the chemical industry. Their main application is in the production of plastics for various applications. The most significant polymerisation application is the casting, moulding or extrusion of polymethyl methacrylate (PMMA) to produce high optical clarity plastics. In addition, many copolymers are used; important copolymers are copolymers of methyl methacrylate and ethyl methacrylate with α-methyl styrene, ethyl acrylate and butyl acrylate. Furthermore, by a simple transesterification reaction, MMA may be converted to other esters such as butyl methacrylate, lauryl methacrylate etc.

Currently, MMA (and MAA) is produced by a number of chemical procedures, one of which is the successful 'Alpha process' whereby MMA is obtained from the ester, methyl propionate, by anhydrous reaction with formaldehyde. In the Alpha process, the methyl propionate is produced by the carbonylation of ethylene. This ethylene feedstock is derived from fossil fuels. Recently, it has become desirable to also source sustainable biomass feedstocks for the chemical industry. Accordingly, an alternative biomass route to MMA instead of using the Alpha process would be advantageous.

Therefore, it is one object of the present invention to address the aforementioned problem, and provide a biological or part biological process for the production of methacrylic acid.

Surprisingly, the present inventors have found a way to apply a novel enzyme substrate combination not previously considered for the formation of methacrylic acid at an industrially applicable level, thereby providing a new and viable bio-based route to key monomers such as MMA.

It is known that the oxidation of isobutyryl-CoA to methacrylyl-CoA occurs naturally in the valine degradation I pathway, and enzymes carrying out this conversion have been observed in some cells. In these systems, the conversion typically uses an acyl-CoA dehydrogenase enzyme which requires a corresponding electron transport system to couple oxidation of the substrate with reduction of ubiquinone, which is then regenerated.

WO201438216 describes a process of producing methacrylic acid from microbes and methacrylyl CoA conversion to the ester using alcohol acyl transferases. The document shows a small amount of conversion of 2-oxoisovaleric acid to isobutyryl CoA and isobutyryl CoA into methacrylyl CoA. It also discusses the theoretical production of methacrylic acid from methacrylyl-CoA in vivo but this is not successfully produced.

However, in WO201438216, the only example of the in vivo production of methacrylic acid uses the *Rhodococcus erythropolis* derived acyl-CoA dehydrogenases recombinantly expressed in a host of the same genus; a *Rhodococcus* bacterium. Other examples attempting to heterologously express the similar acyl-CoA dehydrogenases discovered in *Pseudomonas aeruginosa* in a different host organism did not produce methacrylic acid. The up-regulation or expression of a heterologous acyl-CoA dehydrogenase in a host organism is difficult to achieve and has not yet been reported.

Therefore, it is a further object of the present invention to provide an improved production of methacrylic acid.

There is no known metabolic pathway in which the production of methacrylic acid occurs, either as a product or as an intermediate. Acyl-CoA thioesterase enzymes are known to catalyse the hydrolysis of structurally-related substrates, however these enzymes tend to have very narrow substrate specificity, and either have not been tested for or do not catalyse hydrolysis of methacrylyl-CoA. Furthermore, those rarer varieties that do have broad substrate specificity are likely to be a problem in a biological system, such as the expression host cell, due to off-target hydrolysis of essential cellular thioesters. Again, none are known to catalyse the hydrolysis of methacrylyl-CoA. Accordingly, these enzymes have thus far not been demonstrated as viable for use in industrial applications involving the biological production of methacrylic acid.

Therefore it is a further object of the present invention to address the aforementioned problem and provide a viable enzymatic conversion of methacrylyl-CoA to methacrylic acid which can be used in an industrial process, and which can be used independently of any enzyme functioning to convert isobutyryl CoA into methacrylyl CoA.

STATEMENT OF INVENTION

According to the first aspect of the present invention, there is provided a process of producing methacrylic acid and/or derivatives thereof, comprising the following steps:
(a) Biologically converting isobutyryl-CoA into methacrylyl-CoA by the action of an oxidase; and
(b) Converting methacrylyl-CoA into methacrylic acid and/or derivatives thereof.

According to a second aspect of the present invention, there is provided a process of producing methacrylic acid comprising the following steps:
(a) Converting isobutyryl-CoA into methacrylyl-CoA; and
(b) Biologically converting methacrylyl-CoA into methacrylic acid by the action of a thioesterase, suitably a 4-hydroxybenzoyl-CoA thioesterase (4HBT), transferase, synthetase, and/or a phosphotransacylase and a short chain fatty acid kinase.

Preferably, in the process of the second aspect of the present invention the methacrylyl-CoA is converted to methacrylic acid by the action of a thioesterase, more preferably a 4-hydroxybenzoyl-CoA thioesterase (4HBT), suitably under EC group 3.1.2.23. Most preferably, the methacrylyl-CoA is converted to methacrylic acid by the action of acyl-CoA thioesterase 4HBT from *Arthrobacter* sp. Strain SU.

Advantageously, the processes of the invention provide a further biological route to produce the key chemical methacrylic acid and its known derivatives reducing the industry reliance on fossil fuels and increasing sustainability.

The process enables facile conversion of renewable feedstocks to isobutyryl-CoA by microbial fermentation, and co-expression of enzymes catalysing steps (a) and (b) will provide a direct microbial fermentation route to MAA.

Still further, the processes use enzymes for either step (a) or (b) not previously considered for the production of methacrylic acid and not found in naturally occurring valine pathways. In particular, the enzyme for step (a) acts to convert isobutyryl CoA into methacrylyl CoA without requiring an associated electron transport system, and the enzymes for step (b) have high substrate specificity for methacrylyl CoA to avoid the problem of build-up of this intermediate in host organisms. Therefore either of the enzymes in step (a) or (b) may be used alone to improve partly chemical procedures to form methacrylic acid or to improve biological processes to form methacrylic acid. Alternatively, both enzymes of step (a) and (b) can be used together to form a stand-alone biological process for making methacrylic acid to an industrially applicable level, and which is functional in heterologous host organisms.

Enzymes

In the context of the present invention 'biologically' means using a biological catalyst. Preferably the biological catalysts are enzymes, but may include any catalytic structure derived from a biological source.

In the context of the present invention 'chemically' means using chemical means other than using a biological catalyst such as an enzyme.

In relation to the first aspect, step (b) may be conducted biologically or chemically, preferably biologically.

In relation to the second aspect, step (a) may be conducted biologically or chemically, preferably biologically.

Preferably, step (a) and step (b) are conducted enzymatically using one or more enzymes wherein the enzymes are acting as biological catalysts.

Preferably the oxidase is an oxidase acting on CH—CH bonds, under EC number 1.3.x.x, more preferably an oxidase acting on CH—CH bonds using oxygen as an electron acceptor, under EC number EC 1.3.3.x. Still more preferably, the oxidase is an acyl-CoA oxidase, suitably under EC number EC 1.3.3.6. More preferably the acyl-CoA oxidase is selected from any of the following enzymes: ACX4 from *Arabidopsis thaliana*, short chain acyl-CoA oxidase from *Arthrobacter nicotianae*, peroxisomal acyl-CoA oxidase from *Vigna radiata*, acyl-CoA oxidase from *Candida* sp. and acyl-CoA oxidase 4 from *Candida tropicalis*. Most preferably the acyl-CoA oxidase is ACX4 from *Arabidopsis thaliana*.

Alternatively, isobutyryl-CoA may be converted to methacrylyl-CoA by the action of an oxidoreductase, suitably under EC group number 1.X.X.X. Preferably, the oxidoreductase is an oxidoreductase acting on the CH—CH group of electron donors, suitably under EC group 1.3.X.X. More preferably, the oxidoreductase acting on the CH—CH group of donors is a FAD dependent oxidoreductase, still more preferably the oxidoreductase is a CoA dehydrogenase under EC group 1.3.8.X. More preferably still, the oxidoreductase is a short chain acyl-CoA dehydrogenase, suitably under EC group 1.3.8.1, an isovaleryl-CoA dehydrogenase, suitably under EC group 1.3.8.4, a 2-methyl-branched-chain acyl-CoA dehydrogenase, suitably under EC group 1.3.8.5 or an acyl-CoA dehydrogenase, suitably under EC group 1.3.8.-, such as an isobutyryl-CoA dehydrogenase. Most preferably the oxidoreductase is selected from any of the following enzymes: short/branched chain acyl-CoA dehydrogenase from *Pseudomonas putida*, isobutyryl-CoA dehydrogenase from *Homo sapiens*, isovaleryl-CoA dehydrogenase from *Arabidopsis thaliana*.

The CoA dehydrogenase enzymes would generally require an associated electron transport system to couple oxidation of the substrate with reduction of ubiquinone, which is then regenerated. Such an electron transport system consists of an electron transfer flavoprotein (ETF), and an electron transfer flavoprotein ubiquinone oxidoreductase (ETFQO). The ETF must be compatible with both the acyl-CoA dehydrogenase enzyme and the ETFQO. Accordingly, in the embodiments where an acyl-CoA dehydrogenase is used, one of the following regeneration systems is preferably employed:

In one embodiment, isobutyryl-CoA is converted to methacrylyl-CoA using a host microorganism comprising an endogenous CoA dehydrogenase, with activity on isobutyryl-CoA, and its associated electron transport system, such as is in the case of, for example, *Pseudomonas putida*.

In a second embodiment, isobutyryl-CoA is converted to methacrylyl-CoA in a host organism by the action of a heterologous CoA dehydrogenase enzyme accompanied by the proteins of the electron transport system from the same organism as the heterologous CoA dehydrogenase. For example, the CoA dehydrogenase and electron transport system components from *Homo sapiens, Pseudomonas putida, Paracoccus denitrificans*, or from *Arabidopsis thaliana*, all expressed in *Escherichia coli* (or another host organism).

In a third embodiment, isobutyryl-CoA is converted to methacrylyl-CoA in a host organism by the action of a heterologous CoA dehydrogenase enzyme, accompanied by electron transport system components also from different microorganisms, whereby those components are compatible with each other and with the CoA dehydrogenase. For example, the CoA dehydrogenase from *Homo sapiens* is compatible with the electron transfer flavoprotein of *Sus scrofa* which is in turn compatible with the electron transfer flavoprotein ubiquinone oxidoreductase from *Rhodobacter sphaeroides*. Alternatively, as the ETF-ubiquinone oxidoreductase of *A. thaliana* has good sequence homology with the ETF-ubiquinone oxidoreductase of *R. sphaeroides*, isovaleryl-CoA dehydrogenase and the ETF of *A. thaliana* could form a functional system with the ETF-ubiquinone oxidoreductase from *R. sphaeroides* for the oxidation of isobutyryl-CoA. Finally, the ETF and ETF-ubiquinone oxidoreductase from *Paracoccus denitrificans* are predicted to be compatible with an isobutyryl-CoA dehydrogenase from another source, such as that of *H. sapiens* or homologues from different organisms, due to the similarity of the *P. denitrificans* ETF with the human and porcine ETFs.

Preferably methacrylyl-CoA is converted to methacrylic acid by the action of a thioester hydrolase (also known as a thioesterase), suitably under EC group 3.1.2.X. Still more preferably the enzyme is an acyl CoA thioesterase, suitably under EC group 3.1.2.20, a 3-hydroxyisobutyryl-CoA hydrolase, suitably under EC group 3.1.2.4, an ADP dependent acyl-CoA thioesterase, suitably under EC group 3.1.2.18, a 4-hydroxybenzoyl-CoA thioesterase, suitably under EC group 3.1.2.23, or a thioesterase under EC group 3.1.2.-, such as, for example, a salicyloyl-CoA thioesterase. More preferably the thioesterase is selected from any of the following enzymes: 4HBT from *Arthrobacter* sp. strain SU, 4HBT from *Arthrobacter globiformis*, 4HBT from *Pseudomonas* sp. strain CBS-3, EntH from *Escherichia coli*, YciA from *E. coli*, YciA from *Haemophilus influenzae*, TesA from *Escherichia coli* or TesB from *Escherichia coli*, FcoT from *Mycobacterium tuberculosis*. Still more preferably, the thioesterase is an acyl-CoA thioesterase. Still more preferably, the thioesterase is a 4-hydroxybenzoyl-CoA thioesterase, suitably under EC group 3.1.2.23. Most preferably the acyl-CoA thioesterase is 4HBT from *Arthrobacter* sp. strain SU.

Thus, in one embodiment, isobutyryl-CoA may be converted to methacrylyl-CoA by the action of an oxidase and methacrylyl-CoA may be converted to methacrylic acid by the action of a 4-hydroxybenzoyl-CoA thioesterase, suitably under EC group 3.1.2.23, more preferably the acyl-CoA thioesterase 4HBT from *Arthrobacter* sp. strain SU.

In one embodiment, isobutyryl-CoA may be converted to methacrylyl-CoA by the action of an acyl-CoA oxidase, suitably under EC group number 1.3.3.6, more preferably ACX4 from *Arabidopsis thaliana*, and methacrylyl-CoA may be converted to methacrylic acid by the action of a 4-hydroxybenzoyl-CoA thioesterase, suitably under EC group 3.1.2.23, more preferably the acyl-CoA thioesterase 4HBT from *Arthrobacter* sp. strain SU.

Alternatively, methacrylyl-CoA may be converted to methacrylic acid by the action of one of the following enzymatic routes:

In one embodiment, methacrylyl-CoA is converted to methacrylic acid by the action of a transferase, suitably under EC group number 2.X.X.X. Preferably the transferase is a transferase that transfers sulfur containing groups, suitably under EC group number 2.8.X.X. More preferably, the transferase is a CoA-transferase, suitably under EC group number 2.8.3.X. More preferably still, the transferase is an acetate-dependent acyl-CoA transferase or an acetoacetate-dependent butyric-CoA transferase, suitably under EC group numbers 2.8.3.8 and 2.8.3.9 respectively. Most preferably the transferase is selected from any of the following enzymes: butyryl-CoA:acetoacetate CoA transferase from *Clostridium* sp. SB4, butyryl-CoA:acetoacetate CoA transferase from *Clostridium sticklandii*, butyrate:acetoacetate CoA-transferase from *Clostridium acetobutylicum* ATCC824, acetate coenzyme A transferase ydiF from *Escherichia coli*.

As used herein, the terms ligase, synthetase, and synthase are used interchangeably as is understood in the art.

In a second embodiment, methacrylyl-CoA is converted to methacrylic acid by the action of a synthetase acting in the reverse direction, suitably under EC group number 6.X.X.X. Preferably the synthetase is a carbon-sulfur bond forming synthetase, suitably under EC group number 6.2.X.X. More preferably the synthetase is an acid-thiol ligase, suitably under EC group number 6.2.1.X. Most preferably, the synthetase is a reversible ADP or GDP forming acyl-CoA ligase, such as a GDP forming succinate-CoAsynthetase, suitably under EC group 6.2.1.4, an ADP forming succinate-CoAsynthetase, under EC group 6.2.1.5, an ADP forming glutarate-CoAsynthetase, under EC 6.2.1.6, an ADP forming malate-CoAsynthetase, under EC 6.2.1.9, a GDP forming carboxylic acid-CoAsynthetase, under EC 6.2.1.10, an ADP forming acetate-CoAsynthetase, under EC 6.2.1.13 or an ADP forming citrate-CoAsynthetase, under EC 6.2.1.18.

In a third embodiment, methacrylyl-CoA is converted to methacrylic acid by the combined action of a phosphotransacylase akin to a phosphotransacetylase or a phosphotransbutyrylase under EC group number EC 2.X.X.X, more preferably EC group number EC 2.3.X.X, still more preferably EC 2.3.1.X, most preferably under EC group number 2.3.1.8 or 2.3.1.19, and a short chain fatty acid kinase, under EC group number EC 2.X.X.X, preferably EC 2.7.X.X, more preferably EC 2.7.2.X, most preferably an acetate kinase under EC 2.7.2.1, a formate kinase under EC 2.7.2.6, a butyrate kinase under EC 2.7.2.7, a branched chain fatty acid kinase under EC 2.7.2.14 or a propionate kinase under EC 2.7.2.15. Preferably the phosphotransacylase is a methacrylyl-CoA phosphotransacylase. Preferably the short chain fatty acid kinase is a reversible methacrylic acid kinase. Most preferably the phosphotransacylase is selected from any of the following enzymes: Phosphotransbutyrylase from *Clostridium acetobutylicum* ATCC824. Most preferably the short chain fatty acid kinase is selected from any of the following enzymes: branched chain fatty acid kinase from Spirochete MA-2, butyrate kinase from *Thermotoga maritima*, butyrate kinase form *Clostridium butyricum*.

In the context of the present invention, the term 'derivatives thereof' means any chemical directly related to or comprising either methacrylyl CoA or methacrylic acid, such as the esters thereof, the acyl halides thereof, the anhydrides thereof, the amides thereof, the nitriles thereof, the lactones thereof, the salts thereof, the complexes thereof, the isomers of, the oligomers or polymers thereof and further any substituted versions of these, more preferably, it means the esters or the salts thereof.

Preferably the derivatives thereof of methacrylic acid are methacrylic acid esters. Preferably the methacrylic acid esters are alkyl methacrylates, more preferably lower alkyl (C1-C20) methacrylates, still more preferably, C1-C12 alkyl methacrylates, especially the C1-C4 alkyl esters, such as the methyl, ethyl or butyl methacrylates, or C4-C12 alkyl esters. Most preferably, the methacrylic acid esters are butyl methacrylates, for example n-butylmethacrylate.

The methacrylic acid esters may be formed biologically from the methacrylyl-CoA, preferably by the action of a transferase enzyme under EC group number EC2.X.X.X, more preferably an acyl transferase under EC group number 2.3.X.X, still more preferably an alcohol acyltransferase under EC group number EC2.3.1.84.

Preferably, when methacrylic esters are formed biologically from methacrylyl-CoA, the methacrylyl-CoA is formed biologically from isobutyryl-CoA by the action of an oxidase.

Thus, according to a third aspect of the present invention there is provided a process of producing a methacrylic acid ester comprising the following steps:

(a) biologically converting isobutyryl-CoA into methacrylyl-CoA by the action of an oxidase; and
(b) converting methacrylyl-CoA into a methacrylic acid ester by the action of an alcohol acyltransferase.

Preferably the oxidase of the third aspect is an oxidase acting on CH—CH bonds, under EC number 1.3.x.x, more preferably an oxidase acting on CH—CH bonds using oxygen as an electron acceptor, under EC number EC 1.3.3.x. Still more preferably, the oxidase is an acyl-CoA oxidase, suitably under EC number EC 1.3.3.6. More preferably the acyl-CoA oxidase is selected from any of the following enzymes: ACX4 from *Arabidopsis thaliana*, short chain acyl-CoA oxidase from *Arthrobacter nicotianae*, peroxisomal acyl-CoA oxidase from *Vigna radiata*, acyl-CoA oxidase from *Candida* sp. and acyl-CoA oxidase 4 from *Candida tropicalis*. Most preferably the acyl-CoA oxidase is ACX4 from *Arabidopsis thaliana*.

Preferably, the methacrylic acid esters of the third aspect are alkyl methacrylates, more preferably lower alkyl (C1-C20) methacrylates, still more preferably, C1-C12 alkyl methacrylates, especially the C1-C4 alkyl esters, such as the methyl, ethyl or butyl methacrylates, or C4-C12 alkyl esters. Most preferably, the methacrylic acid esters are butyl methacrylates, for example n-butylmethacrylate.

Suitably the alcohol acyltransferase acts in the presence of an alcohol or phenol, preferably a linear or branched C1-20 unsubstituted alcohol, aralkyl alcohol or phenol, and particularly preferably a C1-8 or C1-4 alkyl alcohol such as methanol, ethanol, n-propanol, isopropanol, n-butanol, isobutanol, sec-butanol, tert-butanol, n-pentylalcohol, isopentyl alcohol, tert-pentyl alcohol, n-hexyl alcohol, isohexyl alcohol, 2-hexyl alcohol, dimethylbutyl alcohol, ethylbutyl alcohol, heptyl alcohol, octyl alcohol, 2-ethylhexyl alcohol; a benzyl alcohol or a phenol. Preferably, the alcohol acyltransferase acts in the presence of an alcohol, more preferably a C1-C12 alcohol, more preferably a C1 to C4 or C4-C12 alcohol, still more preferably in the presence of butanol, such as n-butanol, isobutanol, sec-butanol or tert-butanol. Most preferably, the alcohol acyltransferase acts in the presence of n-butanol.

By the term alcohol herein is meant a species having a hydroxyl group (—OH group) and which is capable of forming an ester group with the methacrylate. Preferably, the alcohol may be a C1 to C20 alkanol, more preferably a C1 to C12 alkanol, still more preferably a C1 to C4 alkanol or a C4 to C12 alkanol, most preferably a C4 alkanol.

Preferably the alcohol acyltransferase is derived from a plant origin, more preferably the plant belongs to any order selected from the group consisting of Zingiberales, Rosales, Ericales, Cucurbitales, Brassicales and Laurales; still more preferably the plant belongs to any family selected from the group consisting of Musaceae, Rosaceae, Ericaceae, Actinidiaceae, Cucurbitaceae, Caricaceae and Lauraceae; still more preferably the plant belongs to any genus selected from the group consisting of *Musa, Fragaria, Malus, Prunus, Pyrus, Vaccinium, Actinidia, Cucumis, Carica* and *Persea*; still more preferably the plant is any one selected from the group consisting of banana, strawberry, apple, *Prunus mume, Pyrus communis*, blueberry, kiwi, melon, papaya and avocado. Most preferably, the alcohol acyltransferase is derived from a fruit origin such as apple, melon or tomato origin, suitably apple origin.

The biological tissue or processed product thereof may be used e.g., fruit, leaves, petals, stem, seed, fruit skin, sarcocarp, etc in which the alcohol acyltransferase is present. Alternatively, the crude enzyme liquid extracted from these biological tissues, purified enzyme, or the like may be used. Alternatively, the gene for the alcohol acyltransferase may be isolated, and introduced into a host microorganism for expression therein.

The use of an alcohol acyltransferase to convert methacrylyl CoA into methacrylic acid esters is fully described in WO2014/038214, the disclosure of which is incorporated herein by reference, in particular the alcohol acyltransferase genes and sequences thereof, and the vector plasmids comprising said sequences.

Further Process Steps

Optionally the process of the first or second aspects of the present invention may further comprise step (c) of converting any methacrylic acid formed in step (b) into a methacrylic acid ester.

Preferably the methacrylic acid esters are alkyl methacrylates, more preferably lower alkyl (C1-C20) methacrylates, more preferably C1-C12 alkyl methacrylates, still more preferably C1-C4 or C4-C12 alkyl methacrylates. Most preferably, the methacrylic acid esters are butyl methacrylate.

The methacrylic acid esters formed in step (c) may be formed biologically or chemically, preferably they are formed biologically.

Optionally, step (c) may be conducted chemically by an esterification reaction with a suitable alcohol. The reaction conditions under which esterification is effected, can be varied considerably. The reaction proceeds very slowly at room temperature, but quite rapidly at elevated temperatures. Typically one of the reactants is used in stoichiometric excess in order to drive the reaction. The other reactant is then called the limiting reagent. About 99% of the limiting reagent, e.g., acids, alcohols or polyols, can be converted to an ester within a few hours. Limiting reagents are typically reagents which are not present in stoichiometric excess, e.g., limiting reagents used to make polyol esters are polyols.

Because the esterification of an alcohol and an organic acid is a reversible reaction, the esterification reaction normally does not go to completion. However, conversions of over 99% can be achieved by removing at least one of the esterification products, typically water. If one of the products is boiling at a lower temperature than the other one, and than the reagents, this removal is typically achieved by distillation. A variety of distillation techniques are known in the art to remove the produced water from the reaction zone. One method of water removal includes carrying out the reaction in a liquid medium which may form an azeotrope having a boiling point that is lower than that of either or each component of the reaction. If the reagents and the resulting ester have boiling points above 100° C. at atmospheric pressure, then the reaction temperature can simply be adjusted to remove water and no liquid medium capable of forming an azeotrope with water is required. Additionally, an entrainer may be used to aid in the distillation of the water from the reaction mixture. Inert materials such as cyclohexane, hexane, benzene, toluene, or xylene may be used as an entrainer in the production of esters. In addition, the reactant having the lower boiling point may also be employed as the entrainer. In this latter case, the reactant used as the entrainer is typically charged into the reaction mixture in excess over the stoichiometric quantities required for the reaction. Esterification processes, including those employing water removal, may be conducted in a batch or continuous mode of operation. Various esterification processes are disclosed in Volume 9 of the Kirk-Othmer Encyclopaedia of Chemical Technology, Fourth Edition (1994), pp. 762-768, the entirety of which is hereby incorporated by reference.

A conventional batch esterification procedure includes charging all of the reactants into the reactor at the beginning of the reaction cycle. In catalytic esterification processes, the catalyst is typically added to the reaction mixture after the batch reaches a target temperature. The reaction mixture may then be heated further. The temperature of the reaction mixture rises until the boiling point of the reaction mixture is achieved, at which point the entrainer, if used, and water by-product boil out of the reaction mixture. Typically, the overhead vapours are condensed, the water separated from the entrainer, and the entrainer recycled to the reactor vessel. The reaction temperature, and therefore the rate of reaction, is limited by the boiling point of the reaction mixture. When the reactant with the lower boiling point is also used as the entrainer, its concentration is gradually reduced as the reaction proceeds. Also the concentrations of the reactants decrease during the reaction, which negatively affects the reaction rate. Thus the reaction temperature, and, therefore, the rate constant for the reaction, increases as the reaction proceeds, irrespective whether an entrainer is used or not, particularly if heat input is continued during the course of the reaction.

Preferably step (c) is conducted biologically by the action of an esterase or hydrolase enzyme acting in relation to an ester bond under EC group number EC 3.1.x.x., more preferably, the enzymes are under. EC 3.1.1.X and are the enzymes of the hydrolase class involved in catalysis of cleavage and formation of ester bonds. A recent review of microbial esterases is as follows: *Int. J. Curr. Microbiol. App. Sci* (2013) 2(7): 135-146.

Preferably the process further comprises one or more further step/s of producing isobutyryl-CoA, more preferably producing isobutyryl-CoA from 2-ketoisovaleric acid, and/or from isobutyric acid.

In one embodiment, the process further comprises the one or more further step/s of producing isobutyryl-CoA from 2-ketoisovaleric acid, the one or more further step/s being any of the following:

Preferably the process further comprises a step of converting 2-ketoisovaleric acid into isobutyryl-CoA. More preferably 2-ketoisovaleric acid is converted to isobutyryl-CoA by a branched chain keto acid dehydrogenase enzyme complex, consisting of the alpha subunit component, the lipoamide acyltransferase component and the lipoamide dehydrogenase component. Most preferably, the dehydrogenase is selected from any of the following enzymes: branched chain keto acid dehydrogenase (BCKD) from *P. putida*, BCKD from *Bacillus subtilis*, BCKD from *P. aeruginosa*, BCKD from *A. thaliana*, BCKD from *Streptomyces coelicolor* and BCKD from *Thermus thermophilus*.

Alternatively, the conversion of 2-ketoisovaleric acid to isobutyryl-CoA may be catalyzed by an oxidoreductase enzyme, suitably under EC group 1.X.X.X, preferably an oxidoreductase acting on the aldehyde or oxo group of donors, suitably under EC group 1.2.X.X, more preferably an oxidoreductase enzyme acting on the aldehyde or oxo group of donors, using an iron-sulfur protein as the electron acceptor, suitably under EC group 1.2.7.X, most preferably a 2-ketoisovalerate ferredoxin reductase (known also as ketovaline ferredoxin oxidoreductases), suitably under EC group number 1.2.7.7, which is a tetramer consisting alpha, beta, gamma and delta subunits. Examples of such enzymes are 2-ketoisovalerate ferredoxin reductase from *Pyrococcus furiosis*; 2-ketoisovalerate ferredoxin reductase from *Pyrococcus* sp.; 2-ketoisovalerate ferredoxin reductase from *Thermococcus* sp; 2-ketoisovalerate ferredoxin reductase from *Thermococcus litoralis*; 2-ketoisovalerate ferredoxin reductase from *Thermococcus profundus* and 2-ketoisovalerate ferredoxin reductase from *Methanobacterium thermoautotrophicum*.

In a second embodiment, the process further comprises the one or more further step/s of producing isobutyryl-CoA from isobutyric acid, the one or more further step/s being any of the following:

Preferably the process further comprises a step of converting isobutyric acid into isobutyryl-CoA.

Optionally, isobutyric acid is converted to isobutyryl-CoA by the action of a ligase enzyme, suitably under EC group number 6.X.X.X, preferably a carbon-sulfur bond forming ligase under EC group 6.2.X.X, more preferably an acid-thiol forming ligase under EC group 6.2.1.X, more preferably a GDP-forming, an ADP forming or an AMP forming ligase, such as an AMP forming acetate-CoA ligase, suitably under EC group 6.2.1.1, a butyrate-CoA ligase, suitably under EC group 6.2.1.2, a carboxylic acid-CoA ligase, suitably under EC group 6.2.1.10, an ADP forming acetate-CoA ligase, suitably under EC group 6.2.1.13, a propionate-CoA ligase, suitably under EC group 6.2.1.17 or an acid-thiol ligase in EC group 6.2.1.-. Most preferably the ligase is selected from any of the following enzyme: AcsA from *Pseudomonas chlororaphis*, butyryl-CoA synthetase from *Paecilomyces varioti*, butyryl-CoA synthetase from bovine heart mitochondria.

In a third embodiment, the process further comprises one or more further step/s of producing isobutyryl-CoA from isobutyrate, the one or more further step/s being any of the following:

Preferably the process further comprises the step of converting isobutyrate to isobutyryl-phosphate, and the step of converting isobutyryl-phosphate to isobutyryl-CoA.

Preferably the isobutyrate is converted to isobutyryl-phosphate by a kinase enzyme, suitably under EC group number EC 2.X.X.X, preferably under EC 2.7.X.X, more preferably under EC group number EC 2.7.2.X, most preferably an acetate kinase, suitably under EC group 2.7.2.1, a formate kinase under EC 2.7.2.6, a butyrate kinase under EC 2.7.2.7, a branched chain fatty acid kinase under EC 2.7.2.14 or a propionate kinase under EC 2.7.2.15. Most preferably the kinase is selected from any of the following enzymes: branched chain fatty acid kinase from Spirochete MA-2, butyrate kinase from *C. butyricum*.

Preferably the isobutyryl-phosphate is converted to isobutyryl-CoA by the action of a transferase enzyme, under EC group number 2.X.X.X, more preferably by the action of an acyltransferase under EC group number 2.3.X.X, still more preferably by the action of acyltransferase transferring groups other than amino-acyl groups under EC group number 2.3.1.X. Still more preferably a phosphate acetyltransferase or a phosphate butyryltransferase, under EC group numbers 2.3.1.8 and 2.3.1.19, respectively. More preferably the transferase is phosphate butyryltransferase from *Clostridium acetobutylicum* ATCC824 or phosphate acetyltransferase from *Bacillus subtilis, Corynebacterium glutamicum* ATCC13032, *Thermotoga maritima* and *Clostridium kluyveri*. Other sources of these enzymes include other anaerobic bacteria, especially *Clostridium* species such as *Clostridium pasteurianum* or *Clostridium beijerinckii*.

Most preferably the process further comprises a step of producing isobutyryl-CoA from isobutyric acid by the action of the synthetase enzyme, preferably an isobutyryl-CoA synthetase, most preferably isobutyryl-CoA synthetase (AcsA) from *P. chloraphis* 823.

Optionally, any of the further process steps as described hereinabove in relation to the first and/or second and/or third embodiments may be combined.

Microorganisms

The enzymes of the above process may be contained within one or more microorganism/s, or present free of a microorganism, for example as a cell-free extract or purified enzyme in a reaction vessel, or held on a column.

Preferably the biological conversions of the process are conducted in one or more host microorganism/s. More preferably the one or more enzymes for conducting the biological conversions are contained within one or more microorganism/s.

Preferably the one or more microorganism/s express the one or more enzymes necessary to catalyse the relevant step/s. More preferably, the relevant step/s and any further enzymatic steps are conducted in vivo, within the one or more microorganism/s.

According to a fourth aspect of the present invention, there is provided a microorganism for use in producing methacrylic acid and/or derivatives thereof according to the process of any of the first, second or third aspects.

The one or more microorganism/s may express the one or more enzymes naturally, or may be genetically engineered to express the one or more enzymes, or may express a combination of both wild type or genetically engineered enzymes. Such a genetically engineered organism may be described as a recombinant organism.

The one or more microorganism/s may express the one or more enzymes endogenously or heterologously, or a combination of endogenous and heterologous enzymes.

In the context of the present invention, the term 'recombinant organism' means a genetically modified or engineered organism comprising genetic material which has been artificially constructed an inserted into the organism. The genetic material may comprise endogenous or heterologous nucleic acids which may or may not have been further genetically modified.

In the context of the present invention, the term 'endogenous' means deriving from the same species of organism.

In the context of the present invention, the term 'heterologous' means deriving from a different species of organism.

In the context of the present invention, the term 'adapted', when used with respect to a microorganism, means a genetically modified or engineered organism, as defined above, or a mutant strain of an organism which, for example, has been selected on the basis that it expresses the one or more enzymes naturally.

The microorganism/s for use in any of the above processes, genetically engineered or modified as described above, may be selected from naturally-occurring wild type or non-naturally occurring recombinant microorganism/s, for example, bacteria, archaea, yeast, fungus, algae or any of a variety of other microorganism/s applicable to fermentation processes.

Therefore, according to a fifth aspect of the present invention there is provided a recombinant microorganism for use in a process of producing methacrylic acid, the microorganism being adapted to conduct the following steps:
 (a) Biologically converting isobutyryl-CoA into methacrylyl-CoA by expression of an oxidase; and
 (b) Biologically converting methacrylyl-CoA into methacrylic acid; wherein the recombinant microorganism is *Escherichia coli*.

According to a sixth aspect of the present invention there is provided a microorganism, for use in a process of producing methacrylic acid, the microorganism being modified by one or more heterologous nucleic acids to conduct the following steps:
 (a) biologically converting isobutyryl-CoA into methacrylyl-CoA by expression of an oxidase; and
 (b) biologically converting methacrylyl-CoA into methacrylic acid.

According to a seventh aspect of the present invention there is provided a microorganism adapted to conduct the following steps:
 (a) Biologically converting isobutyryl-CoA into methacrylyl-CoA by expression of an oxidase; and
 (b) Biologically converting methacrylyl-CoA into methacrylic acid and/or derivatives thereof.

According to a eighth aspect of the present invention there is provided a microorganism adapted to conduct the following steps:
 (a) Biologically converting isobutyryl-CoA into methacrylyl-CoA; and
 (b) Biologically converting methacrylyl-CoA into methacrylic acid by expression of a thioesterase, suitably a 4-hydroxybenzoyl-CoA thioesterase (4HBT), a transferase, a synthetase, and/or a phosphotransacylase and a short chain fatty acid kinase.

According to a further aspect of the present invention there is provided a microorganism adapted to convert methacrylyl-CoA into methacrylic acid by expression of a thioesterase, suitably a 4-hydroxybenzoyl-CoA thioesterase (4HBT), a transferase, a synthetase, and/or a phosphotransacylase and a short chain fatty acid kinase.

According to a still further aspect of the present invention, there is provided a microorganism modified by one or more recombinant nucleic acids encoding one or more enzymes that convert methacrylyl-CoA into methacrylic acid.

According to a still further aspect of the present invention, there is provided a microorganism modified by one or more recombinant nucleic acids encoding one more enzymes that convert methacrylyl-CoA into methacrylic acid esters.

According to a further still aspect of the present invention, there is provided a process of production of methacrylic acid using one or more enzyme/s according to the further aspects.

According to a still further aspect of the present invention, there is provided a process of production of methacrylic acid esters using one or more enzyme/s according to the further aspects.

Further preferred features of the process of the first, second or third aspects may be combined in any combination with the microorganism of the fourth, fifth, sixth, seventh, eighth or further aspects defined hereinabove.

In one embodiment the microorganism/s expresses at least the following enzymes:
 (a) (i) an acyl-CoA oxidase; and/or
  (ii) a CoA dehydrogenase; and optionally one or more of
 (b) (i) an acyl-CoA thioesterase suitably a 4-hydroxybenzoyl-CoA thioesterase (4HBT); and/or
  (ii) an acyl-CoA transferase; and/or
  (iii) acyl-CoA synthetase; and/or
  (iv) a phosphotransacylase and a short chain fatty acid kinase; and optionally
  (v) an alcohol acyltransferase.

In one embodiment, the microorganism/s expresses at least the following enzymes:
 (a) (i) an acyl-CoA oxidase; and optionally one or more of
 (b) (i) an acyl-CoA thioesterase; and/or
  (ii) an acyl-CoA transferase; and/or
  (iii) acyl-CoA synthetase; and/or
  (iv) a phosphotransacylase and a short chain fatty acid kinase; and optionally
  (v) an alcohol acyltransferase.

In one embodiment of the fourth, fifth or eighth aspects, the microorganism/s expresses at least the following enzymes:
 (a) (i) an acyl-CoA thioesterase, suitably a 4-hydroxybenzoyl-CoA thioesterase (4HBT); and/or
  (ii) an acyl-CoA transferase; and/or
  (iii) acyl-CoA synthetase; and/or
  (iv) a phosphotransacylase and a short chain fatty acid kinase; and optionally one or more of:
 (b) (i) an acyl-CoA oxidase; and/or
  (ii) an acyl-CoA dehydrogenase; and further optionally
 (c) (i) an alcohol acyltransferase.

Preferably, when present, the CoA dehydrogenase is accompanied by a complementary electron transport system.

In a preferred embodiment, the microorganism/s express at least one of the following enzymes:
 (a) an acyl-CoA oxidase, such as ACX4; and
 (b) an acyl-CoA thioesterase, such as 4HBT.

In a more preferred embodiment, the microorganism/s express at least one of the following enzymes:
 (a) ACX4, suitably from *A. thaliana*; and
 (b) 4HBT, suitably from *Arthrobacter* sp.

In some embodiments, the microorganism is adapted to conduct the following steps:
 (a) biologically converting isobutyryl-CoA into methacrylyl-CoA by expression of an acyl-CoA oxidase; and (b) biologically converting methacrylyl-CoA into a C1 to C20 methacrylic acid ester, suitably a C1 to C12 methacrylic acid ester, such as a C1 to C4 or a C4 to C12 methacrylic acid ester by expression of an alcohol acyltransferase.

Preferably, the methacrylic acid ester is a C1 to C20 methacrylic acid ester, more preferably a C1 to C12 methacrylic acid ester, still more preferably a C1 to C4 or C4 to C12 methacrylic acid ester, most preferably butyl methacrylate.

In these embodiments, the microorganism may be *Escherichia coli* and/or the acyl-CoA oxidase is ACX4 from *Arabidopsis thaliana* and/or the alcohol acyltransferase is derived from plant origin as set out herein, for example fruit such as apple and/or the microorganism is a recombinant microorganism. Preferably the microorganism may be *Escherichia coli*, the acyl-CoA oxidase may be ACX4 from *Arabidopsis thaliana*, the alcohol acyltransferase may be derived from apple, melon or tomato origin and the microorganism may be a recombinant organism.

Preferably the microorganism/s express both of the said enzymes (a) and (b) of said preferred or some embodiments.

Preferably the microorganism/s further express one or more of the following enzymes: a branched chain keto acid dehydrogenase enzyme or either an ADP forming, a GDP forming, or an AMP forming acyl-CoA synthetase/synthase/ligase; or a short chain fatty acid kinase and a phosphotransacylase.

More preferably the microorganism/s further express one or more of the following enzymes: 2-ketoisovalerate dehydrogenase, an isobutyrate-CoA ligase, an ADP forming, GDP forming or an AMP forming acyl-CoA synthetase/synthase/ligase, or a short chain fatty acid kinase and a phosphotransacylase.

Most preferably, the microorganism/s further express an isobutyryl-CoA synthetase, in particular AcsA from *Pseudomonas chloraphis*, in particular *Pseudomonas chloraphis* B23

In relation to the fourth, sixth, seventh, eighth and further aspects, preferably the host microorganism/s are bacteria, examples of suitable bacteria include: enterobacteria belonging to proteobacteria of the genus *Escherichia, Enterobacter, Pantoea, Klebsiella, Serratia, Erwinia, Salmonella, Morganella*, or the like, so-called coryneform bacteria belonging to the genus *Brevibacterium, Corynebacterium* or *Microbacterium* and bacteria belonging to the genus *Alicyclobacillus, Bacillus, Hydrogenobacter, Methanococcus, Acetobacter, Acinetobacter, Agrobacterium, Axorhizobium, Azotobacter, Anaplasma, Bacteroides, Bartonella, Bordetella, Borrelia, Brucella, Burkholderia, Calymmatobacterium, Campylobacter, Chlamydia, Chlamydophila, Clostridium, Coxiella, Ehrlichia, Enterococcus, Francisella, Fusobacterium, Gardnerella, Haemophilus, Helicobacter, Kelbsiella, Methanobacterium, Micrococcus, Moraxella, Mycobacterium, Mycoplasma, Neisseria, Pasteurella, Peptostreptococcus, Porphyromonas, Prevotella, Pseudomonas, Rhizobium, Rickettsia, Rochalimaea, Rothia, Shigella, Staphylococcus, Stenotrophomonas, Streptococcus, Treponema, Vibrio, Wolbachia, Yersinia*, or the like.

Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens, Hydrogenobacter thermophilus, Methanococcus jannaschii* and *Pseudomonas putida*.

In relation to the fourth, sixth, seventh, eighth and further aspects, preferably the bacterium is *Escherichia coli*.

Exemplary yeasts or fungi include those belonging to the genera *Saccharomyces, Schizosaccharomyces, Candida, Kluyveromyces, Aspergillus, Pichia, Crytpococcus*, or the like. Exemplary yeast or fungi species include those selected from *Saccharomyces cerevisiae, Schizosaccharomyces pombe, Kluyveromyces lactis, Kluyveromyces marxianus, Aspergillus terreus, Aspergillus niger, Pichia pastoris*, or the like.

The one or more microorganism/s of any of the fourth, sixth, seventh, eighth or further aspects may be genetically modified to enhance or reduce the activity of the above natural or genetically engineered enzymes.

Preferably the microorganism/s are genetically engineered to enhance production of methacrylic acid and/or derivatives thereof.

Enhancing the production of methacrylic acid and/or derivatives thereof may include making modifications to existing cellular metabolic processes, nucleic acids and/or proteins by the use of various genetic engineering techniques known in the art. Enhancing the production of methacrylic acid and/or derivatives thereof may also include modifying the microorganism/s to express one or more heterologous genes in the microorganism/s. These may include genes encoding enzymes of the desired pathway to methacrylic acid from carbon based feedstocks such as those set out herein, or may include other auxiliary genes which act to promote the functioning and expression of the enzymes in such pathways either directly or indirectly as discussed in detail below.

Accordingly, the microorganism/s may be modified to express the one or more genes for production of methacrylic acid and/or derivatives thereof and preferably, the microorganism/s are further modified to enhance production of methacrylic acid and/or derivatives thereof.

The one or more gene/s which may be expressed within the microorganism/s such that it is modified to produce methacrylic acid and/or derivatives thereof include those encoding any of the following enzymes: ACX4 from *Arabidopsis thaliana*, short chain acyl-CoA oxidase from *Arthrobacter nicotianae*, peroxisomal acyl-CoA oxidase from *Vigna radiata*, acyl-CoA oxidase 4 from *Candida tropicalis*, acyl-CoA oxidase from *Candida* sp. and related oxidases with broad substrate range, 4-hydroxybenzoyl-CoA thioesterase from *Arthrobacter* sp, YciA from *Escherichia coli*, YciA from *Haemophilus influenzae*, TesA from *Escherichia coli*, TesB from *Escherichia coli*, 4HBT from *Arthrobacter globiformis*, 4HBT from *Pseudomonas* sp. Strain CBS-3, EntH from *Escherichia coli*, butyryl-CoA acetoacetate CoA transferase from *Clostridium* sp. SB4, butyryl-CoA acetoacetate CoA transferase from *Clostridium sticklandii*, butyrate-acetoacetate CoA-transferase from *Clostridium acetobutylicum* ATCC824, acetate coenzyme A transferase ydiF from *Escherichia coli*, phosphotransbutyrylase from *Clostridium acetobutylicum* ATCC824, branched chain fatty acid kinase from Spirochete MA-2, butyrate kinase from *Thermotoga maritima*, butyrate kinase from *Clostridium butyricum*, branched chain acyl-CoA dehydrogenase from *Pseudomonas putida*, isobutyryl-CoA dehydrogenase from *Homo sapiens*, isovaleryl-CoA dehydrogenase from *Arabidopsis thaliana*, electron transfer flavoprotein from *H. sapiens*, electron transfer flavoprotein from *Sus scrofa*, electron transfer flavoprotein from *Arabidopsis thaliana*, electron transfer flavoprotein from *Pseudomonas*

*putida*, electron transfer flavoprotein from *Paracoccus denitrificans*, electron transfer flavoprotein ubiquinone oxidoreductase from *H. sapiens*, electron transfer flavoprotein ubiquinone oxidoreductase from *Sus scrofa*, electron transfer flavoprotein ubiquinone oxidoreductase from *Pseudomonas putida*, electron transfer flavoprotein ubiquinone oxidoreductase from *Arabidopsis thaliana*, electron transfer flavoprotein ubiquinone oxidoreductase from *Rhodobacter sphaeroides*, electron transfer flavoprotein ubiquinone oxidoreductase from *Paracoccus denitrificans*.

The one or more gene/s which may be expressed within the microorganism/s such that it is modified to enhance production of methacrylic acid and/or derivatives thereof include those encoding any of the following enzymes: AcsA from *Pseudomonas chlororaphis*; bkdA1, bkdA2, bkdB and IpdV from *Bacillus subtilis*; bkdA1, bkdA2, bkdB and IpdV from *Pseudomonas putida*; alsS from *Bacillus subtilis*, ilvD from *Escherichia coli*, ilvC from *Escherichia coli*, ilvB from *Escherichia coli*, ilvN from *Escherichia coli*, ilvI from *Escherichia coli*, ilvG from *Escherichia coli*, ilvM from *Escherichia coli*, ilvH from *Escherichia coli* and ilvH from *Escherichia coli* with G14D and S17F mutations, ilvC from *Corynebacterium glutamicum* R harbouring S34G, L48E and R49F mutations, ilvB and ilvN from *Corynebacterium* R and ilvN from *Corynebacterium* R harbouring a G156E mutations well as homologues from other organisms, baring similar mutations as described above, to alleviate feedback inhibition of enzymes and to alter cofactor dependence, where appropriate.

The present invention may further comprise modifications which decrease or eliminate the activity of an enzyme that catalyses synthesis of a compound other than methacrylic acid and/or derivatives thereof by competing for the same substrates and/or intermediates in the above mentioned biosynthesis pathways. Examples of such enzymes include YciA, TesA, TesB from *Escherichia coli*, and those encoded by fadB, ilvA, panB, leuA, ygaZ, ygaH, aceF, aceE, lpdA, tpiA, pfkA, pfkB, mdh, poxB, ilvE, ldhA and lldD, in *Escherichia coli*, as well as homologues in other host strains as described herein.

The present invention may further comprise modifications that decrease or eliminate the activity of an enzyme which metabolises methacrylic acid and/or derivatives thereof or metabolises an intermediate in the above-mentioned biosynthesis pathways. Examples of such enzymes related to the metabolism are enzymes of the native valine degradation pathway in *E. coli*, or other thioesterases that may consume thioester intermediates of the engineered pathway.

The present invention may also further comprise modifications which decrease or eliminate the activity of proteins involved in other cellular functions that remove intermediates in the above mentioned biosynthesis pathways. Examples of such cellular functions may include storage mechanisms such as vacuolar storage (e.g. in yeasts) or other intracellular bodies capable of storing metabolites (e.g. bacterial microcompartments), the bacterial periplasm or transport mechanisms such as transmembrane pumps or porins capable of exporting metabolites.

Sources of nucleic acids for genes encoding the proteins, in particular the enzymes expressed in the microorganism/s according to the present invention can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, *Homo sapiens*, *Propionibacterium fredenreichii*, *Methylobacterium extorquens*, *Shigella flexneri*, *Salmonella enterica*, *Yersinia frederiksenii*, *Propionibacterium acnes*, *Rattus norvegicus*, *Caenorhabditis elegans*, *Bacillus cereus*, *Acinetobacter calcoaceticus*, *Acinetobacter baylyi*, *Acinetobacter* sp., *Clostridium kluyveri*, *Pseudomonas* sp., *Thermus thermophilus*, *Pseudomonas aeruginosa*, *Pseudomonas putida*, *Oryctolagus cuniculus*, *Clostridium acetobutylicum*, *Leuconostoc mesenteroides*, *Eubacterium barkeri*, *Bacteroides capillosus*, *Anaerotruncus colihominis*, *Natranaerobius thermophilus*, *Campylobacter jejuni*, *Arabidopsis thaliana*, *Corynebacterium glutamicum*, *Sus scrofa*, *Bacillus subtilus*, *Pseudomonas fluorescens*, *Serratia marcescens*, *Streptomyces coelicolor*, *Methylibium petroleiphilum*, *Streptomyces cinnamonensis*, *Streptomyces avermitilis*, *Archaeoglobus fulgidus*, *Haloarcula marismortui*, *Pyrobaculum aerophilum*, *Saccharomyces cerevisiae*, *Clostridium cochlearium*, *Clostridium tetanomorphum*, *Clostridium tetani*, *Citrobacter amalonaticus*, *Ralstonia eutropha*, *Mus musculus*, *Bos taurus*, *Fusobacterium nucleatum*, *Morganella morganii*, *Clostridium pasteurianum*, *Rhodobacter sphaeroides*, *Xanthobacter autotrophicus*, *Clostridium propionicum*, *Megasphaera elsdenii*, *Aspergillus terreus*, *Candida*, *Sulfolobus tokodaii*, *Metallosphaera sedula*, *Chloroflexus aurantiacus*, *Clostridium saccharoperbutylacetonicum*, *Acidaminococcus fermentans*, *Helicobacter pylori*, as well as other exemplary species disclosed herein or available as source organisms for corresponding genes.

It should be noted that the one or more genes encoding enzymes which may be expressed in microorganism/s of the invention also comprise genes encoding variants of said enzymes, for example, variant enzymes which include substitutions, deletions, insertions or additions of one or several amino acids in the polypeptide sequence, and wherein said polypeptide retains the activity of the unmodified enzyme. Such variant enzymes also include variant enzymes which have a reduced enzymatic activity when compared to the unmodified enzyme and enzymes with modified allosteric control, for example ilvH from *Escherichia coli* with G14D and S17F mutations, ilvC from *Corynebacterium glutamicum* R harbouring S34G, L48E and R49F mutations, ilvB and ilvN from *Corynebacterium* R and ilvN from *Corynebacterium* R harbouring a G156E mutation.

Methods for constructing and testing the expression of a protein in a non-naturally occurring methacrylic acid producing microorganism can be performed, for example, by recombinant techniques and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of methacrylic acid and/or derivatives thereof or an intermediate in the formation thereof can be introduced stably or transiently into a microorganism cell using techniques well known in the art including, but not limited to, conjugation, electroporation, chemical transformation, transduction, transfection, and ultrasound transformation.

Examples of transformation methods can include treating recipient microorganism/s_cells with calcium chloride so to increase permeability of the DNA, and preparing competent cells from cells which are in the growth phase, followed by transformation with DNA. Alternatively, a method of making DNA-recipient cells into protoplasts or spheroplasts, which can easily take up recombinant DNA, followed by introducing the recombinant DNA into the cells, which is known to be applicable to *Bacillus subtilis*, actinomycetes and yeasts can also be employed. In addition, transformation of microorganisms can also be performed by electroporation. Such methods are well known in the art.

For exogenous expression in *E. coli* or other prokaryotic microorganism cells, some nucleic acid sequences in the genes or cDNAs of eukaryotic nucleic acids can encode targeting signals such as an N-terminal mitochondrial or other targeting signal, which can be removed before transformation into prokaryotic microorganism cells, if desired. For example, removal of a mitochondrial leader sequence led to increased expression in *E. coli* (Hoffmeister et al., J. Biol. Chem. 280:4329-4338 (2005). For exogenous expression in yeast or other eukaryotic microorganism cells, genes can be expressed in the cytosol without the addition of leader sequence, or can be targeted to mitochondria or other organelles, or targeted for secretion, by the addition of a suitable targeting sequence such as a mitochondrial targeting or secretion signal suitable for the target organelle. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins within the microorganism/s.

An expression vector or vectors can be constructed to include one or more biosynthetic pathway enzyme(s) encoding nucleic acids as exemplified herein operably linked to expression control sequences functional in the microorganism/s. Expression vectors applicable for use in the microorganism/s of the invention include, for example, plasmids, cosmids, phage vectors, viral vectors, episomes and artificial chromosomes, including vectors and selection sequences or markers operable for stable integration into a host chromosome.

Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive, inducible or repressible promoters, transcription enhancers, transcription terminators, translation signals and the like which are well known in the art. When two or more exogenous encoding nucleic acid sequences are to be co-expressed, both nucleic acid sequences can be inserted, for example, into a single expression vector or in separate expression vectors. For single vector expression, the encoding nucleic acids can be operationally linked to one common expression control sequence or linked to different expression control sequences, such as inducible promoters and constitutive promoters. In some embodiments, the vector may have two or more promoters for the co-expression of multiple genes or operons. In some embodiments, the genes/operons may be expressed on one or more different vectors with one or more corresponding promoters.

The vector used for transformation can be a vector autonomously replicable in a cell of the microorganism/s. Examples of vectors autonomously replicable in bacteria of the Enterobacteriaceae bacteria such as *E. coli* can include plasmid vectors pUC19, pUC18, pBR322, RSF1010, pHSG299, pHSG298, pHSG399, pHSG398, pSTV28, pSTV29, pET20b(+), pET28b(+) (pET vectors are available from Novagen), pLysS, (pHSG and pSTV vectors are available from Takara Bio Inc.), pMW119, pMW118, pMW219, pMW218 (pMW vectors are available from Nippon Gene Co., Ltd.) and so forth, and their derivatives. Furthermore, vectors for coryneform bacteria can include pAM330 (Japanese Patent Laid-open No. 58-67699), pHM1519 (Japanese Patent Laid-open No. 58-77895), pSFK6 (Japanese Patent Laid-open No. 2000-262288), pVK7 (USP2003-0175912A), pAJ655, pAJ611, pAJ1844 (Japanese Patent Laid-open No. 58-192900), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491) and so forth. Furthermore, vectors for yeast can include yeast plasmids, such as for example pD902 or pD905 for *Pichia pastoris*, or pD1201, pD1204, pD1205, pD1207, pD1211, pD1214 pD1215, pD1217, pD1218, pD1221, pD1224, pD1225, pD1227, pD1231, pD1234, pD1235, pD1237 for *Saccharomyces cerevisiae*. Genes can also be integrated into the host chromosome, using well known methods (e.g. Datensko and Wanner (Datsenko, K. A. and Wanner, B. L. 2000, Proc. Natl. Acad. Sci. USA, 97:6640-6645)).

Enhancement of the activity of an enzyme can include enhancing expression of a target gene by replacing an expression regulatory sequence of the target gene such as a promoter on the genomic DNA or plasmid with a promoter which has an appropriate strength. For example, the thr promoter, lac promoter, trp promoter, trc promoter, pL promoter, tac promoter, etc., are known as frequently used promoters. Examples of promoters with high expression activity in microorganisms such as bacteria can include promoters of the elongation factor Tu (EF-Tu) gene, tuf, promoters of genes that encode co-chaperonin GroES/EL, thioredoxin reductase, phosphoglycerate mutase, glyceraldehyde-3-phosphate dehydrogenase, and the like (WO2006/028063, EP1697525). Examples of strong promoters and methods for evaluating the strength of promoters are well known in the art.

Moreover, it is also possible to substitute several nucleotides in a promoter region of a gene, so that the promoter has an appropriate strength, as disclosed in WO 2000/18935. Substitution of the expression regulatory sequence can be performed, for example, in the same manner as in gene substitution using a temperature sensitive plasmid. Examples of vectors having a temperature sensitive replication origin which can be used for *Escherichia coli* or *Pantoea ananatis* can include, for example, plasmid pMAN997 described in International Publication WO 1999/03988, its derivative, and so forth. Furthermore, substitution of an expression regulatory sequence can also be performed by methods which employ linear DNA, such as a method called "Red-driven integration" using Red recombinase of A-phage (Datsenko, K. A. and Wanner, B. L. 2000, Proc. Natl. Acad. Sci. USA, 97:6640-6645), a method combining the Red-driven integration method and the A-phage excisive system (Cho, E. H. et al. 2002. J. Bacteriol. 184:5200-5203) (WO2005/010175), and so forth. The modification of an expression regulatory sequence can be combined with increasing the gene copy number.

Furthermore, it is known that substitution of several nucleotides in a spacer between the ribosome binding site (RBS) and the start codon, and particularly, the sequences immediately upstream of the start codon profoundly affect the mRNA translatability. Translation can be enhanced by modifying these sequences.

When a target gene is introduced into the aforementioned plasmid or chromosome, any promoter can be used for expression of the gene so long as a promoter that functions in the microorganism/s used is chosen. The promoter can be the native promoter of the gene, or a modified promoter. Expression of a gene can also be controlled by suitably choosing a promoter that potently functions in the chosen microorganism/s, or by approximating −35 and −10 regions of a promoter close to the consensus sequence.

The transformation, transduction, conjugational or chromosomal insertion of exogenous nucleic acid sequences involved in a metabolic or synthetic pathway can be confirmed using methods well known in the art. Such methods include, for example, extraction of plasmid or chromosomal DNA followed by polymerase chain amplification of specific target sequences, or restriction mapping, further nucleic acid analysis such as Northern blots or polymerase chain reaction (PCR) amplification of mRNA, or polyacrylamide gel electrophoresis, or enzymatic activity measurements, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired gene product, and it is further understood that expression levels can be optimized to obtain sufficient expression using methods well known in the art.

Optionally, the one or more microorganism/s of the fourth, sixth, seventh, eighth or further aspects for use in any of the above processes of the invention may further be modified to reduce or eliminate the activity of an enzyme or protein partaking in a cellular function which:
(i) diverts material from methacrylic acid producing pathways; and/or
(ii) metabolises methacrylic acid and/or derivatives thereof.

In order to reduce or eliminate the activities of the aforementioned enzymes or proteins, mutations for reducing or eliminating intracellular activities of the enzymes or proteins can be introduced into the genes of the aforementioned enzymes or proteins by conventional random or site directed mutagenesis or genetic engineering techniques. Examples of the mutagenesis can include, for example, X-ray or ultraviolet ray irradiation, treatment with a mutagen such as N-methyl-N'-nitro-N-nitrosoguanidine, in vitro site directed or random mutagenesis by high fidelity or error-prone polymerase chain reaction, respectively, and so forth. The site on the gene where the mutation is introduced can be in the coding region encoding the enzyme or protein or an expression control region such as a promoter. Examples of genetic engineering techniques can include genetic recombination, transduction, cell fusion, gene knockouts, and so forth.

A decrease or elimination of the intracellular activity of the objective enzyme or protein and the degree of decrease can be confirmed by measuring the enzyme or protein activity in a cell extract or a purified fraction thereof obtained from a candidate strain, and comparing it with that of a wild-type strain, or by measuring formation of the target product by whole cells.

Examples of other methods for imparting or enhancing methacrylic acid and/or derivatives thereof producing ability and/or intermediates thereof can include imparting resistance to methacrylic acid or an organic acid analogue, respiratory inhibitor or the like and imparting sensitivity to a cell wall synthesis inhibitor. These methods can include, for example, selecting for resistant cells by growing with increasing concentrations of the toxic substance, imparting monofluoroacetic acid resistance, imparting adenine resistance or thymine resistance, attenuating urease, imparting malonic acid resistance, imparting resistance to benzopyrones or naphthoquinones, imparting HOQNO resistance, imparting alpha-ketomalonic acid resistance, imparting guanidine resistance, imparting sensitivity to penicillin, and so forth as is known in the art.

Examples of such resistant bacteria can include the following strains: *Brevibacterium flavum* AJ3949 FERM BP-2632; *Corynebacterium glutamicum* AJ11628 FERM P-5736; *Brevibacterium flavum* AJ11355 FERM P-5007; *Corynebacterium glutamicum* AJ11368 FERM P-5020; *Brevibacterium flavum* AJ11217 FERM P-4318; *Corynebacterium glutamicum* AJ11218 FERM P-4319; *Brevibacterium flavum* AJ11564 FERM P-5472; *Brevibacterium flavum* AJ11439 FERM P-5136; *Corynebacterium glutamicum* H7684 FERM BP-3004; *Brevibacterium lactofermentum* AJ11426 FERM P-5123; *Corynebacterium glutamicum* AJ11440 FERM P-5137; and *Brevibacterium lactofermentum* AJ11796 FERM P-6402.

Further methods for imparting or enhancing methacrylic acid and/or derivatives thereof producing ability and/or intermediates thereof can include imparting resistance to down-regulators/inhibitors, imparting sensitivity to up-regulators/activators or alleviating the need for allosteric activation of enzymes by other compounds. For example, alleviation of the need for allosteric activation of branched chain keto acid dehydrogenase from *Pseudomonas putida* by valine, or alleviation of allosteric inhibition of acetolactate synthase from *Escherichia coli*.

Fermentation

Accordingly, the above-mentioned processes of the invention may be conducted by culturing microorganism/s of the fourth, sixth, seventh, eighth or further aspects of the invention which are able to produce the methacrylyl-CoA intermediate and/or methacrylic acid and/or derivatives thereof such as methacrylic acid esters, suitably in a medium.

Suitably therefore, the processes of the first, second or third aspects of the invention may further comprise the step of culturing one or more microorganism/s to produce methacrylic acid and/or derivatives thereof such as methacrylic acid esters.

Preferably said culturing takes place in a fermentation medium.

Therefore, according to an ninth aspect of the present invention, there is provided a process of fermentation comprising culturing one or more microorganism/s of the fourth, fifth, sixth, seventh, eighth or further aspects in a fermentation medium to produce methacrylic acid and/or derivatives thereof such as methacrylic acid esters.

The methacrylic acid and/or derivative thereof may be present in the fermentation medium or within the cells of the microorganism/s.

Suitably, therefore, the processes of the first, second or third aspects of the invention may further comprise the step of collecting the methacrylic acid and/or an intermediate in the formation thereof and/or a derivative thereof such as a methacrylic acid ester from the fermentation medium or from the microorganism/s cells.

The methacrylic acid and/or a derivative thereof such as a methacrylic acid ester may be present in the fermentation medium by the microorganism/s secreting methacrylic acid and/or a derivative thereof such as a methacrylic acid ester as described hereinabove.

The methacrylic acid and/or a derivative thereof such as a methacrylic acid ester may be present in the cells of the microorganism/s by the microorganism accumulating methacrylic acid and/or derivatives thereof such as a methacrylic acid ester as described hereinabove.

Suitably therefore the cells are removed from the fermentation medium by any means known in the art, such as filtration, centrifugation, etc, and methacrylic acid or salt thereof and/or methacrylic acid ester is collected from the fermentation medium by any means known in the art, such as: distillation, liquid-liquid extraction, etc. Suitably therefore, the processes of the invention may comprise a further step of collecting the methacrylic acid and/or derivative thereof such as a methacrylic acid ester from the surrounding medium, this may be implemented by first removing the cells from the medium by filtration or centrifugation and then extracting the methacrylic acid and/or derivative thereof from the clarified medium by distillation or liquid-liquid extraction.

Optionally, collecting the methacrylic acid and/or derivative thereof such as a methacrylic acid ester may further comprise a step of releasing the methacrylic acid and/or derivative thereof such as a methacrylic acid ester from the cell which may be performed by any means known in the art, preferably where the cell is lysed to release the desirable product, such as: by sonication, homogenization, enzymatic treatment, bead-milling, osmotic shock, freeze-thaw, acid/base treatment, phage lysis, etc. followed by a similar collection method from the fermentation medium as detailed above. Suitably therefore, the processes of the invention may comprise the further steps of collecting the methacrylic acid and/or derivative thereof such as a methacrylic acid ester from the cells, this may be implemented by lysing the cells, and subsequent filtration of cell debris followed by the extraction of methacrylic acid and/or derivative thereof such as a methacrylic acid ester.

Suitably, culturing or cultivation of a microorganism requires a carbon based feedstock upon which the microorganism may derive energy and grow. Preferably, therefore, the microorganism/s are cultured on a carbon based feedstock, and the processes of the first or second aspects of the invention may further comprise the step of culturing the one or more microorganism/s which are able to produce methacrylic acid and/or derivatives thereof from a carbon based feedstock.

Preferably the culturing or cultivation takes place in a fermentation medium, suitably a surrounding medium which surrounds the microorganism/s, preferably the carbon based feedstock is present in the medium, optionally dissolved or suspended in the medium, bubbled through the medium and/or mixed with the medium. Preferably therefore the medium comprises the microorganism/s and the carbon based feedstock together with any buffers and salts.

Therefore, according to a tenth aspect of the present invention there is provided a fermentation medium comprising one or more microorganism/s of the fourth, fifth, sixth, seventh, eighth or further aspects.

Preferably the fermentation medium further comprises methacrylic acid and/or derivatives thereof such as methacrylic acid esters.

Preferably the microorganism/s produce methacrylic acid and/or derivatives thereof such as methacrylic acid esters at an increased rate above that of the basal rate as explained above, such that preferably the concentration of methacrylic acid and/or derivatives thereof such as methacrylic acid esters present in the medium, either from direct secretion or from lysing the cells, is at high titre.

Preferably the titre of methacrylic acid and/or derivatives thereof such as methacrylic acid esters present in the fermentation medium is at least 5 mg/L. For example, 5, 15, 25, 35, 45, 55, 65, 75, 85, 95, 105, 115, 125, 135, 145, 155 mg/L, preferably at least greater than 130 mg/L.

Preferably, in an embodiment where the methacrylic acid and/or derivatives thereof such as methacrylic acid esters accumulate within the microorganism/s, the concentration of methacrylic acid and/or an intermediate thereof and/or derivatives thereof such as methacrylic acid esters present in the cell is at least 0.05 mM, more preferably at least 0.1 mM, more preferably at least 1 mM, more preferably at least 2 mM, more preferably at least 5 mM, more preferably at least 10 mM. Preferably the concentration of methacrylic acid or an intermediate thereof and/or derivatives thereof such as methacrylic acid esters in the cell ranges between 10 mM to about 300 mM, more preferably about 20 mM to about 200 mM, still more preferably about 30 mM to about 100 mM most preferably about 40 mM to about 70 mM.

The microorganism/s of the invention may be cultivated or cultured as a batch, a repeated batch, a fed-batch, a repeated fed-batch or a continuous cultivation process.

Suitably, the cultivation process takes place in a culture medium, otherwise known herein as the surrounding medium or fermentation medium. Preferably a fed-batch or repeated fed-batch process is applied, wherein the carbon source and/or the nitrogen source and/or additional compounds are fed to the cultivation process. More preferably, the carbon and/or nitrogen source are fed into the cultivation process.

The fermentation medium in which the microorganism/s of the present invention are cultured may be any commercially available medium suitable for the needs of the organism in question, provided that the relevant nutrients required by said organism are limiting. The culture may be aerobic or anaerobic, however in the context of the invention where the oxidase enzyme is employed, the culture is preferably aerobic.

The fermentation medium suitably contains a carbon based feedstock as described above, and a nitrogen source, as well as additional compounds required for growth of the microorganism/s and/or the formation of methacrylic acid and/or methacrylic acid ester.

Examples of suitable carbon based feedstocks known in the art include glucose, maltose, maltodextrins, sucrose, hydrolysed starch, starch, lignin, aromatics, syngas or its components, methane, ethane, propane, butane, molasses and oils. Preferably the carbon based feedstock is derived from biomass. Mixtures may also be used, as well as wastes, such as municipal waste, food waste and lignocellulosic wastes from food processing, forestry or agriculture.

Examples of suitable nitrogen sources known in the art include soy bean meal, corn steep liquor, yeast extract, ammonia, ammonium salts, nitrate salts, urea, nitrogen gas or other nitrogenous sources.

Examples of additional compounds required for growth of the microorganism/s include antibiotics, antifungals, antioxidants, buffers, phosphate, sulphate, magnesium salts, trace elements and/or vitamins.

The total amount of carbon based feedstock and nitrogen source to be added to the medium may vary depending on the needs of the microorganism/s and/or the length of the cultivation process.

The ratio between the carbon based feedstock and the nitrogen source in the culture medium may vary considerably.

Additional compounds required for growth of the microorganism/s and/or for the production of methacrylic acid and/or derivatives thereof such as methacrylic acid esters, like phosphate, sulphate or trace elements, may be added in amounts that may vary between different classes of microorganisms, i.e. between fungi, yeasts and bacteria. In addition, the amount of additional compound to be added may be determined by whether methacrylic acid and/or derivatives thereof such as methacrylic acid esters are formed and what pathways are used to form them.

Typically, the amount of each fermentation medium component necessary for growth of a microorganism is determined by measuring the growth yield on the nutrient and further assessed in relation to the amount of carbon based feedstock used in the culturing or cultivation process, since the amount of biomass formed will be primarily determined by the amount of carbon based feedstock used, and the nutrient limitations imposed during any feeding regime.

The culturing or cultivation process according to the invention is preferably performed on an industrial scale. An industrial scale process is understood to encompass a culturing or cultivation process in one or more fermenters of a volume scale which is $\geq 0.01$ m$^3$, preferably $\geq 0.1$ m$^3$, preferably $\geq 0.5$ m$^3$, preferably $\geq 5$ m$^3$, preferably $\geq 10$ m$^3$, more preferably $\geq 25$ m$^3$, more preferably $\geq 50$ m$^3$, more preferably $\geq 100$ m$^3$, most preferably $\geq 200$ m$^3$.

Preferably, the culturing or cultivation of the microorganism/s of the invention is generally performed in a bioreactor. A Bioreactor is generally understood to mean a container in which microorganisms are industrially cultured. Bioreactors can be of any size, number and form, and can include inlets for providing nutrients, additional compounds for growth, fresh medium, carbon based feedstocks, additives of gases, such as, but not limited to, air, nitrogen, oxygen or carbon dioxide. Bioreactors may also comprise outlets for removing volumes of the culture medium to collect the methacrylic acid and/or methacrylic acid ester either from the fermentation medium itself or from within the microorganism/s. The bioreactor preferably also has an outlet for sampling of the culture. The bioreactor can generally be configured to mix the fermentation medium, for example, by stirring, rocking, shaking, inverting, bubbling of gas through the culture etc. Alternatively, some continuous cultures do not require mixing, for example microreactor systems using a plug flow system. Bioreactors are common and well known in the art and examples may be found in standard texts, such as 'Biotechnology: A Textbook of Industrial Microbiology, Second Edition' (1989) Authors: Wulf Cruegar and Annelise Crueger, translated by Thomas D. Brock Sinauer Associates, Inc., Sunderland, Mass.

Therefore, according to an eleventh aspect of the invention, there is provided a bioreactor comprising one or more microorganism/s of the fourth, fifth, sixth, seventh, eighth or further aspects and/or the fermentation medium of the tenth aspect.

Optionally, the bioreactor may comprise a plurality of different microorganism/s of the present invention.

Preferably, the bioreactor comprises only microorganism/s capable of performing the process of the invention.

More preferably the bioreactor comprises only microorganism/s of the same species such that the same culturing conditions can be used throughout.

Biomass Feedstock

Preferably the biomass used comprises a high amount of carbohydrates, particularly preferable are carbohydrates which are sources of C5 or C6 sugars, carbon based gases, or aromatics, preferably C5 or C6 sugars, more preferably glucose, such as, but not limited to starch, lignin, cellulose, glycogen, arabinoxylan, chitin, or pectin.

Alternatively, the biomass used comprises a high amount of fats, particularly preferable are fats or oils which are sources of glycerol and fatty acids, specifically triglycerides. Suitable triglycerides include any oil or fat which is readily available from a plant or animal source. Examples of such oils and fats include: palm oil, linseed oil, rapeseed oil, lard, butter, herring oil, coconut oil, vegetable oil, sunflower oil, castor oil, soybean oil, olive oil, cocoa butter, ghee, blubber etc.

The biomass may be composed of one or more different biomass sources. Examples of suitable biomass sources are as follows; virgin wood, energy crops, agricultural residues, food waste, municipal waste and industrial waste or co-products.

Virgin wood biomass sources may include but are not limited to; wood chips; bark; brash; logs; sawdust; wood pellets or briquettes.

Energy crop biomass sources may include but are not limited to; short rotation coppices or forestry; non-woody grasses such as *miscanthus*, hemp switchgrass, reeds or rye; agricultural crops such as sugar, starch or oil crops; or aquatic plants such as micro or macroalgae and weeds.

Agricultural residues may include but are not limited to; husks; straw; corn stover; flour; grains; poultry litter; manure; slurry; syngas; or silage.

Food wastes may include but are not limited to; peel/skin; shells; husks; cores; pips/stones; inedible parts of animals or fish; pulp from juice and oil extraction; spent grains or hops from brewing; domestic kitchen waste; lard or oils or fats.

Industrial wastes may include but are not limited to; untreated wood including pallets, treated wood, shale gases, wood composites including MDF/OSD, wood laminates, paper pulp/shreddings/waste; textiles including fibre/yarn/effluent; or sewage sludge.

Further Products

Furthermore, the production of other useful organic compounds, for example derivatives of methacrylic acid such as various esters thereof is also envisaged. Accordingly, the methacrylic acid product may be esterified to produce an ester thereof. Potential esters may be selected from $C_1$-$C_{20}$ alkyl or $C_2$-$C_{12}$ hydroxyalkyl, glycidyl, isobornyl, dimethylaminoethyl, tripropyleneglycol esters. Most preferably the alcohols or alkenes used for forming the esters may be derived from bio sources, e.g. biomethanol, bioethanol, biobutanol. Preferred esters are ethyl, n-butyl, i-butyl, hydroxymethyl, hydroxypropyl or methyl methacrylate, most preferably, methyl methacrylate or butyl methacrylate.

Preferably methacrylic acid is converted to alkyl or hydroxyalkyl methacrylate by an esterification reaction. Suitable reaction conditions for such a conversion are well known in the art and are described in conjunction with the production of methacrylic acid in WO/2012/069813.

According to a twelfth aspect of the present invention there is provided a method of preparing polymers or copolymers of methacrylic acid or methacrylic acid esters, comprising the steps of:
  (i) preparation of methacrylic acid and/or derivatives thereof in accordance with the first, second or third aspects or further aspects of the invention;
  (ii) optional esterification of the methacrylic acid prepared in (i) to produce the methacrylic acid ester;
  (iii) polymerisation of the methacrylic acid and/or derivatives thereof prepared in (i) and/or, if present, the ester prepared in (ii), optionally with one or more comonomers, to produce polymers or copolymers thereof.

Step (i) may comprise any of the further features outlined in relation to the first, second and third aspects hereinabove in combination with those of the twelfth aspect.

Preferably, the methacrylic acid ester of (ii) above is selected from $C_1$-$C_{20}$ alkyl or $C_2$-$C_{12}$ hydroxyalkyl, glycidyl, isobornyl, dimethylaminoethyl, tripropyleneglycol esters, more preferably, ethyl, n-butyl, i-butyl, hydroxymethyl, hydroxypropyl or methyl methacrylate, most preferably, methyl methacrylate, ethyl methacrylate, butyl methacrylate or butyl methacrylate.

Thus, according to a further aspect of the present invention there is provided a method of preparing polymers or copolymers of methacrylic acid esters, comprising the steps of:
(i) preparation of methacrylic acid esters in accordance with the third aspect or further aspects of the invention;
(ii) polymerisation of the methacrylic acid and/or derivatives thereof prepared in (i), optionally with one or more comonomers, to produce polymers or copolymers thereof.

Step (i) may comprise any of the further features outlined in relation to the third aspect hereinabove in combination with those of the twelfth aspect.

Advantageously, such polymers will have an appreciable portion if not all of the monomer residues derived from a source other than fossil fuels.

In any case, preferred comonomers include for example, monoethylenically unsaturated carboxylic acids and dicarboxylic acids and their derivatives, such as esters, amides and anhydrides.

Particularly preferred comonomers are acrylic acid, methyl acrylate, ethyl acrylate, propyl acrylate, n-butyl acrylate, iso-butyl acrylate, t-butyl acrylate, 2-ethylhexyl acrylate, hydroxyethyl acrylate, iso-bornyl acrylate, methacrylic acid, methyl methacrylate, ethyl methacrylate, propyl methacrylate, n-butyl methacrylate, iso-butyl methacrylate, t-butyl methacrylate, 2-ethylhexyl methacrylate, hydroxyethyl methacrylate, lauryl methacrylate, glycidyl methacrylate, hydroxypropyl methacrylate, iso-bornyl methacrylate, dimethylaminoethyl methacrylate, tripropyleneglycol diacrylate, styrene, α-methyl styrene, vinyl acetate, isocyanates including toluene diisocyanate and p,p'-methylene diphenyl diisocyanate, acrylonitrile, butadiene, butadiene and styrene (MBS) and ABS subject to any of the above comonomers not being the momomer selected from methacrylic acid or a methacrylic acid ester in (i) or (ii) above in any given copolymerisation of the said acid monomer or ester in (i) or a said ester monomer in (ii) with one or more of the comonomers.

It is of course also possible to use mixtures of different comonomers. The comonomers themselves may or may not be prepared by the same process as the monomers from (i) or (ii) above.

According to a twelfth aspect of the present invention there is provided polymethacrylic acid, polymethylmethacrylate (PMMA) and polybutylmethacrylate homopolymers or copolymers formed from the method of the eleventh aspect of the invention herein.

EXAMPLES

The invention will now be illustrated with reference to the following non-limiting examples and figures in which:—

Figure 3:
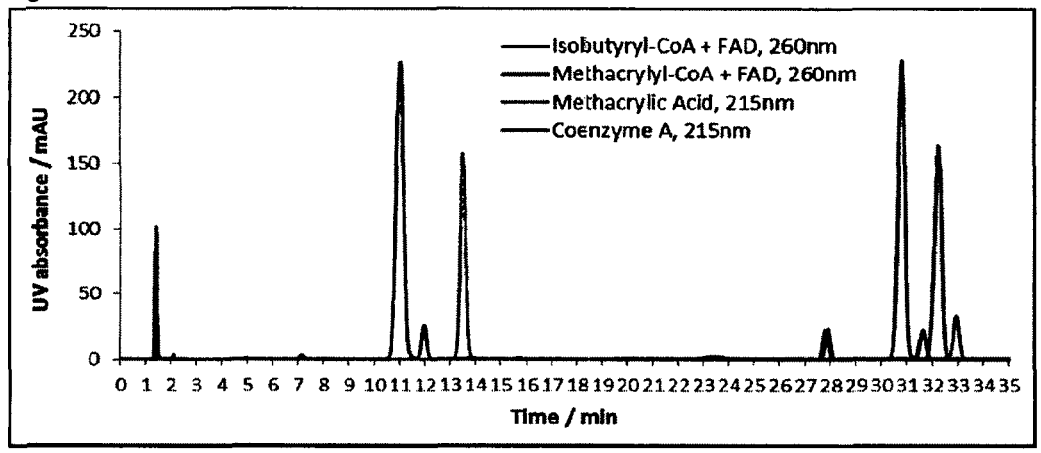

FIG. 3 shows overlaid HPLC traces of standards isobutyryl-CoA (major peak at 32.2 min and minor peak at 32.9 min), methacrylyl-CoA (major peak at 30.8 min and minor peak at 31.6 min), methacrylic acid (peak at 13.5 mins) and coenzyme A (major peak at 11 min and minor peak at 12 min) using the HPLC method to determine in vitro activity of the short chain acyl-CoA oxidase (ACX4) from *Arabidopsis thaliana* for the oxidation of isobutyryl-CoA to methacrylyl-CoA. Flavin adenine dinucleotide eluted at 27.8 min, and was used as an internal standard for isobutyryl-CoA and methacrylyl-CoA.

Figure 4:
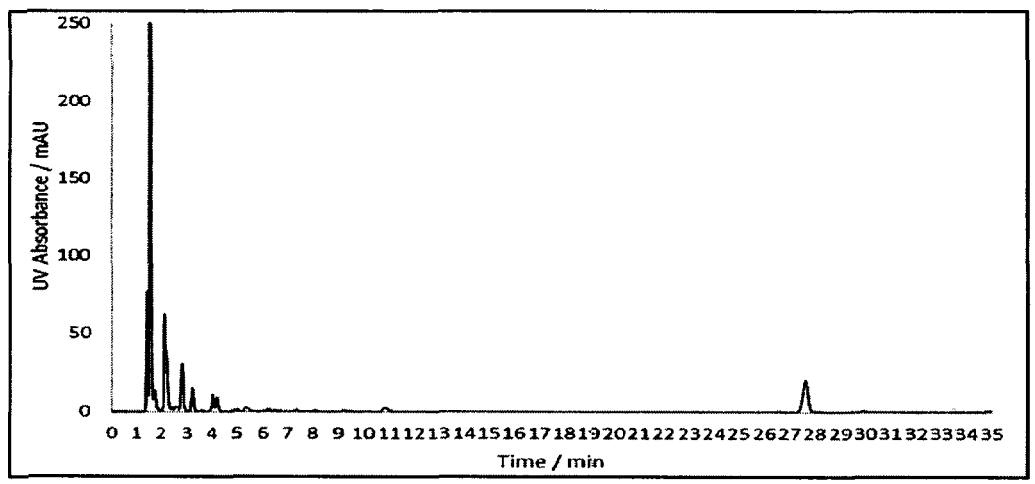

FIG. 4 shows the HPLC trace of the assay mixture containing ACX4 cell free extract, purified carboxy-terminal hexahistidine tagged 4HBT and flavin adenine dinucleotide in HEPES assay buffer, with no substrate added, as a negative control.

Figure 5:
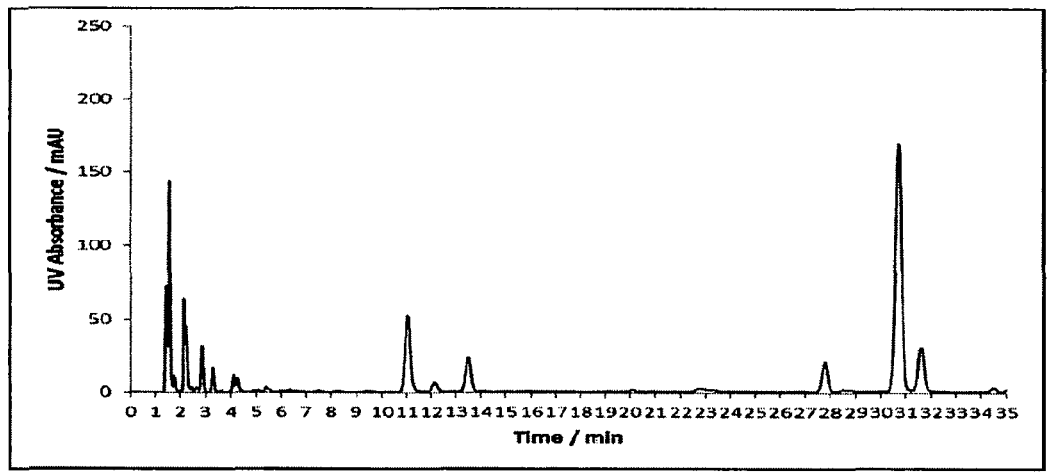

FIG. 5 shows the HPLC analysis of an assay mixture after 30 min incubation of the cell free extract of ACX4 with isobutyryl-CoA in HEPES assay buffer containing flavin adenine dinucleotide.

Figure 6:
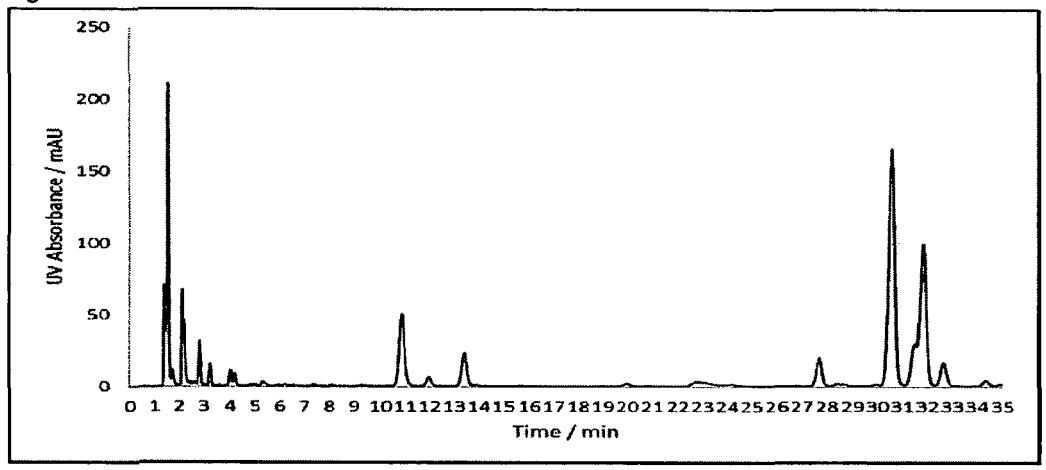

FIG. 6 shows the HPLC analysis of an assay mixture after 30 min incubation of the cell free extract of ACX4 with isobutyryl-CoA in HEPES assay buffer containing flavin adenine dinucleotide that was spiked with additional isobutyryl-CoA after the reaction mixture was stopped by acidification.

Figure 7:
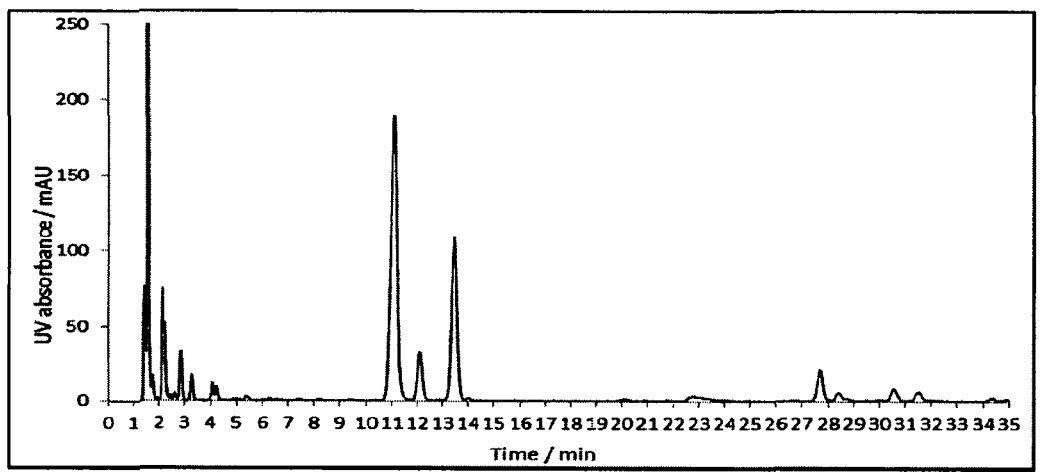

FIG. 7 shows the HPLC analysis of the enzyme coupled reaction for the conversion of isobutyryl-CoA to methacrylic acid and coenzyme A by the ACX4 cell free extract and the purified carboxy-terminal His-tagged 4HBT.

Figure 8:
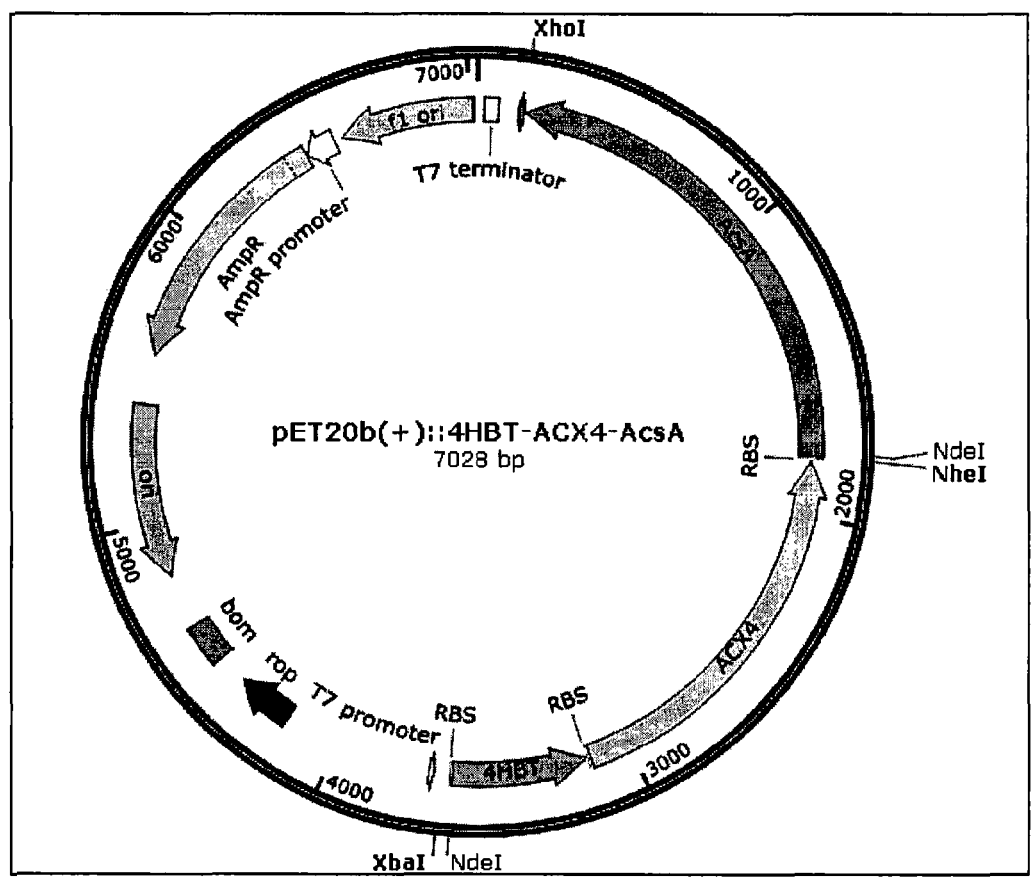

FIG. 8 shows the pET20b(+)::4HBT-ACX-AcsA plasmid, a pET20b(+) plasmid containing the 4HBT gene, ACX4 gene and the AcsA gene all under the control of a single T7 promoter.

Figure 9:
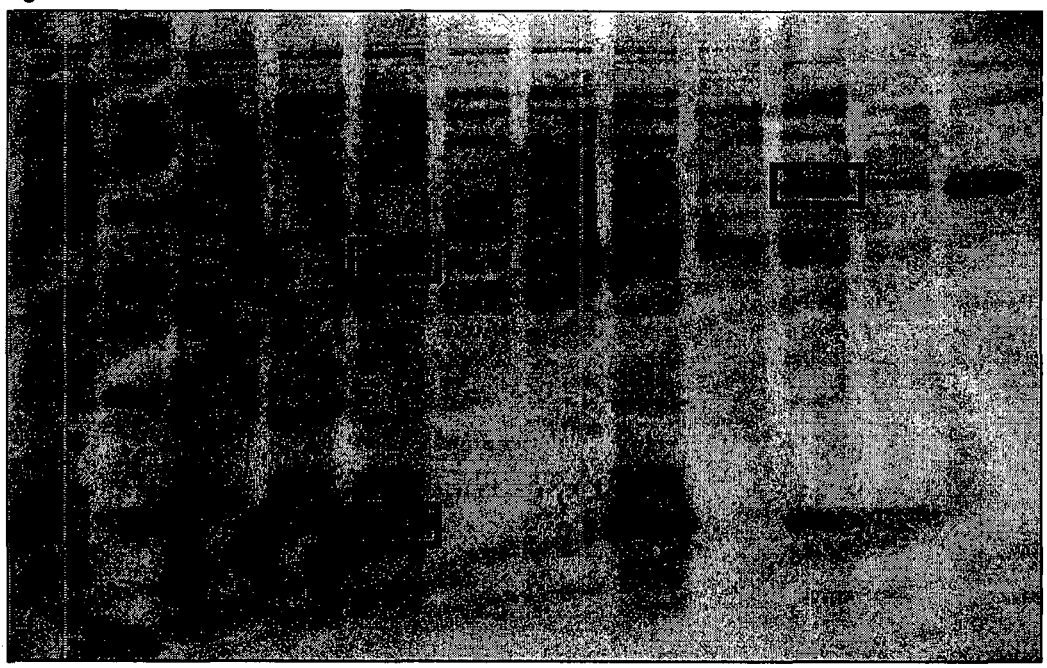

FIG. 9 shows an SDS-PAGE analysis of 4HBT, ACX4 and AcsA co-expression by *E. coli* BL21 (DE3) pLysS pET20b(+)::4HBT-ACX4-AcsA.

Figure 10:
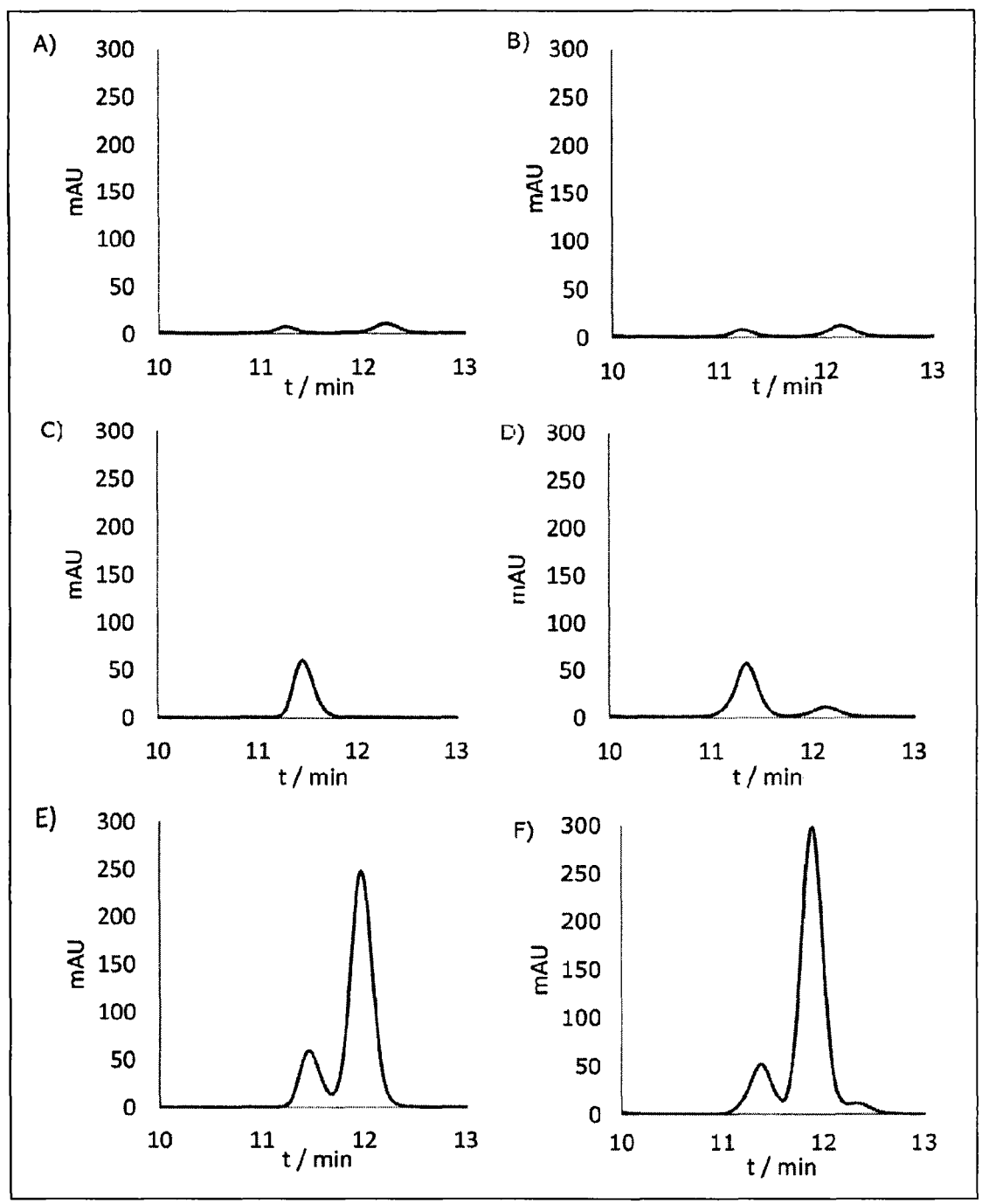

FIG. 10 shows the HPLC traces performed for the analysis of the biotransformation of isobutyric acid to methacrylic acid and all relevant controls, 20.5 h post induction, whereby FIG. 10A shows traces performed for the culture of *E. coli* BL21 (DE3) pLysS pET20b(+)::4HBT-ACX4-AcsA in which no isobutyric acid was added; FIG. 10B shows the culture of *E. coli* BL21 (DE3) pLysS pET20b(+) in which no isobutyric acid was added; FIG. 10C shows the HPLC trace of a 5 mM standard of isobutyric acid; FIG. 10D shows the HPLC trace of a culture of *E. coli* BL21 (DE3) pLysS pET20b(+) that was supplemented with isobutyric acid (5 mM) 1 h after the induction of recombinant protein expression, FIG. 10E shows the HPLC trace of a cocktail of isobutyric acid (5 mM) and methacrylic acid (200 μM) standards and FIG. 10F shows the HPLC trace of the *E. coli* BL21 (DE3) pLysS pET20b(+)::4HBT-ACX4-AcsA culture in which isobutyric acid (5 mM) was added 1 h after the induction of recombinant protein expression.

Figure 11:
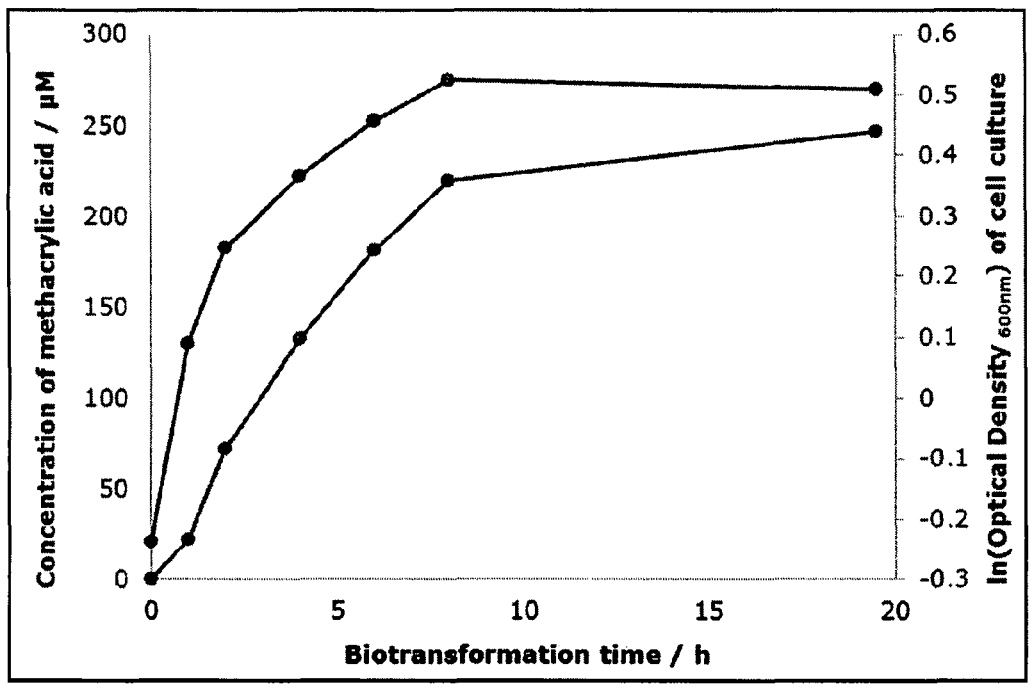

FIG. 11 shows the change in concentration of methacrylic acid with time (bottom line) in the *E. coli* BL21 (DE3) pLysS pET20b(+)::4HBT-ACX4-AcsA culture that was supplemented with isobutyric acid, as well as the change in the $\ln(OD_{600})$ of the culture with time (top line), since the addition of isobutyric acid to the culture.

Figure 12:
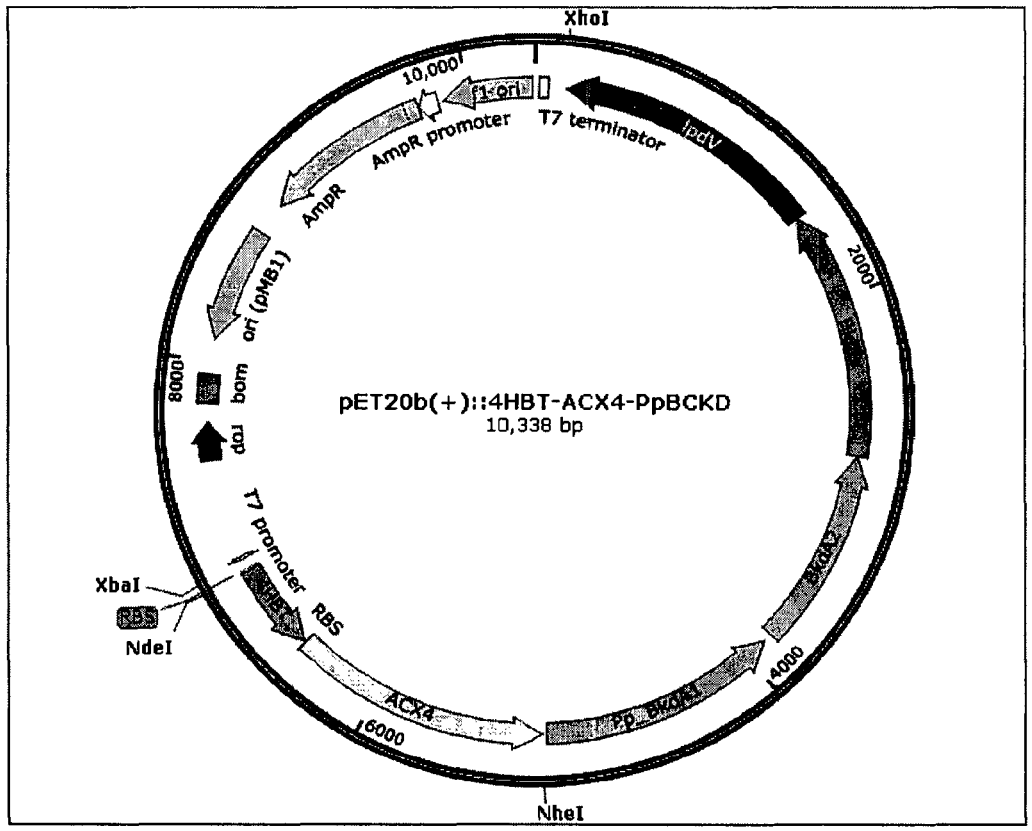

FIG. 12 shows the pET20b(+)::4HBT-ACX4-ppBCKD plasmid, the pET20b(+) plasmid with the codon optimised genes encoding 4HBT from *Arthrobacter* sp. strain SU, ACX4 from *Arabidopsis thaliana* as well as the bkdA1, bkdA2, bkdB and IpdV genes from *Pseudomonas putida* KT2440, all under the control of a single T7 promoter.

Figure 13:
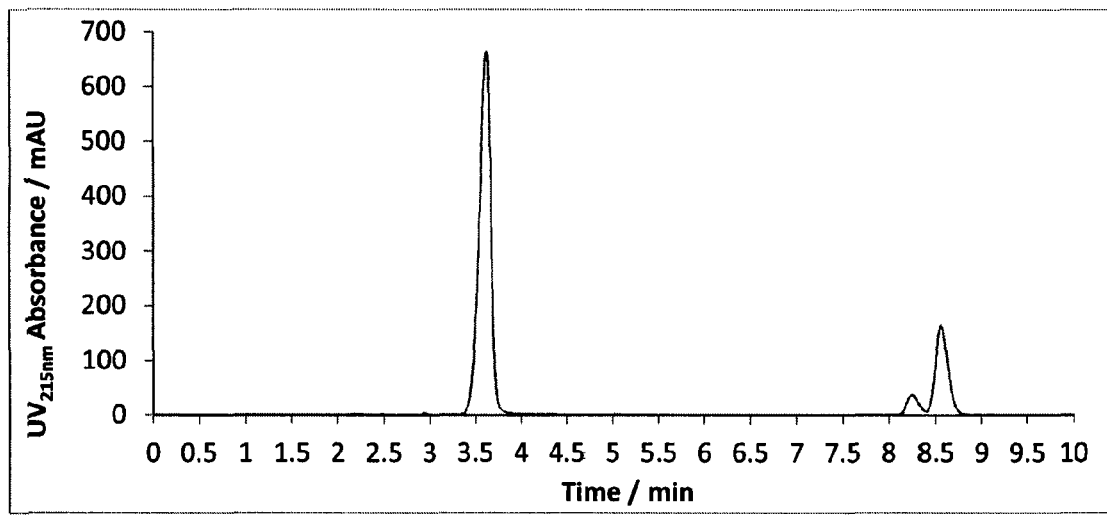

FIG. 13 shows the HPLC analysis of a cocktail of 2-ketoisovaleric acid (5 mM), isobutyric acid (5 mM) and methacrylic acid (200 μM) standards, whereby the components were separated by isocratic elution, using 14% acetonitrile in 50 mM $KH_2PO_4$ that was acidified to pH 2.5 with HCl, at a flow-rate of 1 ml·min$^{-1}$.

Figure 14:
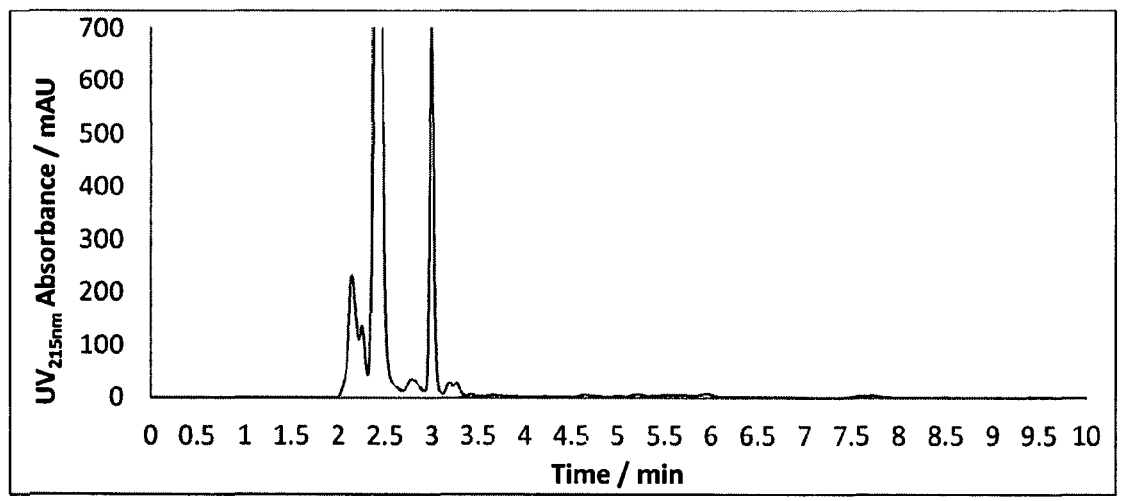

FIG. 14 shows the HPLC analysis of the culture of the *E. coli* BL21 (DE3) pLysS pET20b(+) negative control strain, whereby components were separated by isocratic elution, using 14% acetonitrile in 50 mM $KH_2PO_4$ that was acidified to pH 2.5 with HCl, at a flow-rate of 1 ml·min$^{-1}$.

Figure 15:
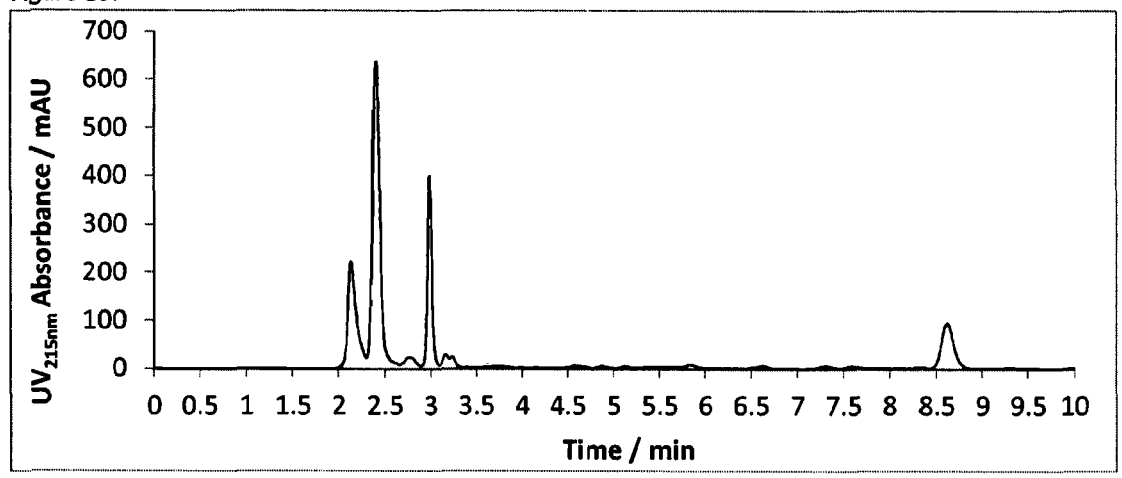

FIG. 15 shows the HPLC analysis of the culture of *E. coli* BL21 (DE3) pLysS pET20b(+)::4HBT-ACX4-ppBCKD, whereby components were separated by isocratic elution, using 14% acetonitrile in 50 mM $KH_2PO_4$ that was acidified to pH 2.5 with HCl, at a flow-rate of 1 ml·min$^{-1}$, demonstrating the production of methacrylic acid from glucose.

Figure 16:
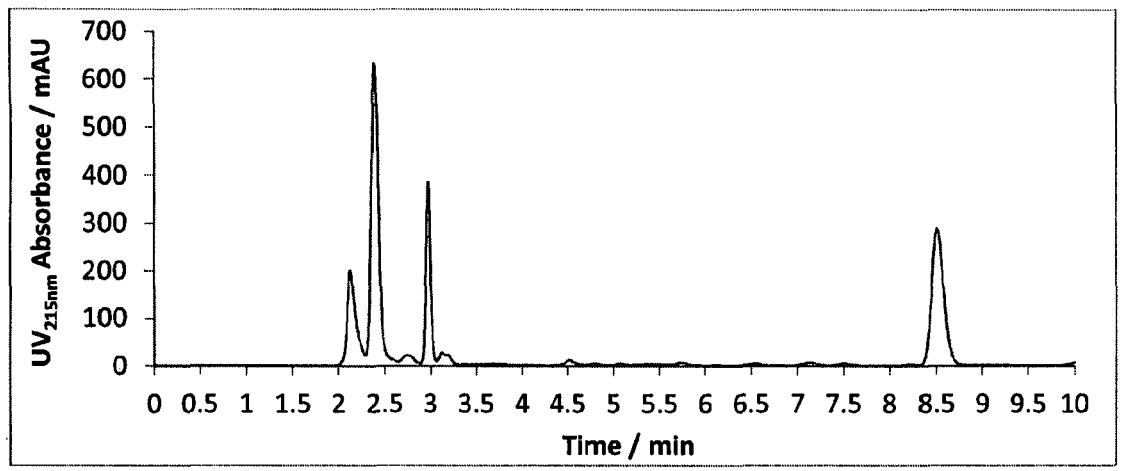

FIG. 16 shows the HPLC analysis of a sample of the culture of *E. coli* BL21 (DE3) pLysS pET20b(+)::4HBT-ACX4-ppBCKD, that was spiked with an additional 0.24 mM authentic methacrylic acid, whereby components were separated by isocratic elution, using 14% acetonitrile in 50 mM $KH_2PO_4$ that was acidified to pH 2.5 with HCl, at a flow-rate of 1 ml·min$^{-1}$.

Figure 17:
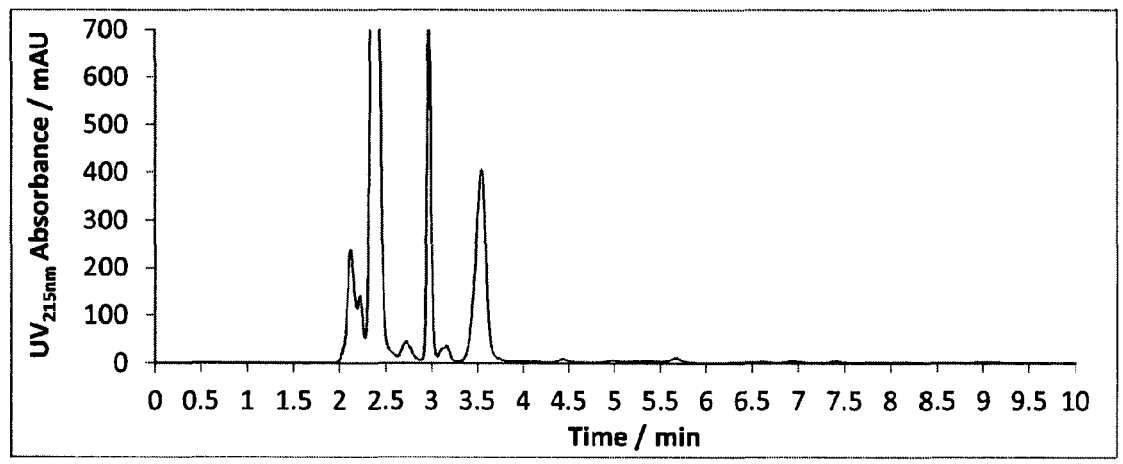

FIG. 17 shows the HPLC analysis of the culture of the *E. coli* BL21 (DE3) pLysS pET20b(+) negative control strain that was supplemented with 2-ketoisovaleric acid, whereby components were separated by isocratic elution, using 14% acetonitrile in 50 mM $KH_2PO_4$ that was acidified to pH 2.5 with HCl, at a flow-rate of 1 ml·min$^{-1}$.

Figure 18:
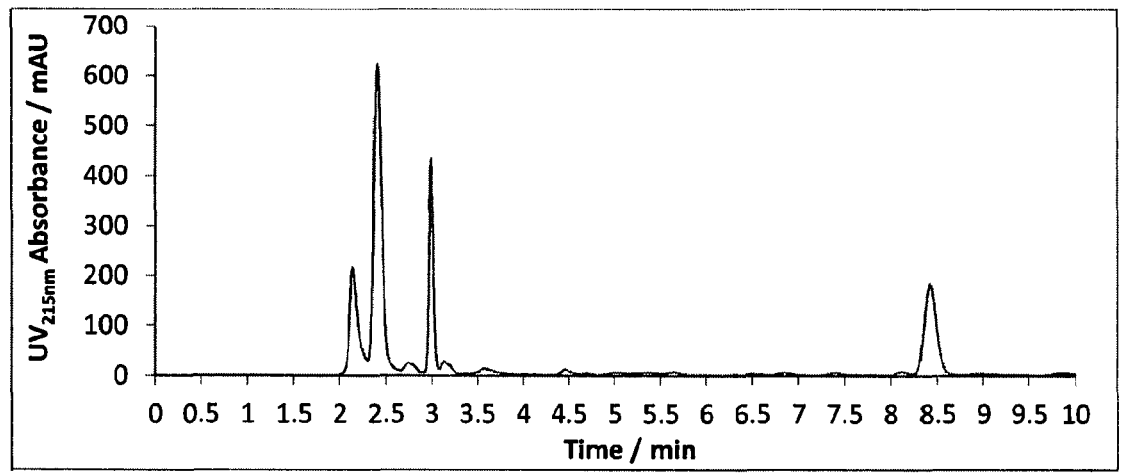

FIG. 18 shows the HPLC analysis of the culture of *E. coli* BL21 (DE3) pLysS pET20b(+)::4HBT-ACX4-ppBCKD that was supplemented with 2-ketoisovaleric acid (5 mM), whereby the components were separated by isocratic elution, using 14% acetonitrile in 50 mM $KH_2PO_4$ that was acidified to pH 2.5 with HCl, at a flow-rate of 1 ml·min$^{-1}$, demonstrating that supplementing the culture with 2-ketoisovaleric acid boosts methacrylic acid production by this strain.

Figure 19:
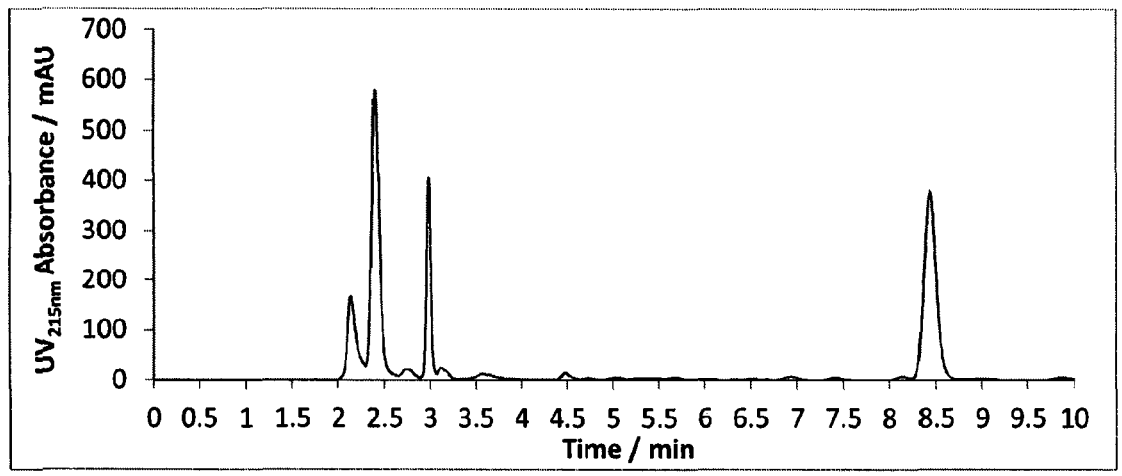

FIG. 19 shows the HPLC analysis of a sample of the culture of *E. coli* BL21 (DE3) pLysS pET20b(+)::4HBT-ACX4-ppBCKD that was supplemented with 2-ketoisovaleric acid (5 mM), that was spiked with an additional 0.24 mM authentic methacrylic acid, whereby the components were separated by isocratic elution, using 14% acetonitrile in 50 mM $KH_2PO_4$ that was acidified to pH 2.5 with HCl, at a flow-rate of 1 ml·min$^{-1}$.

Figure 20:
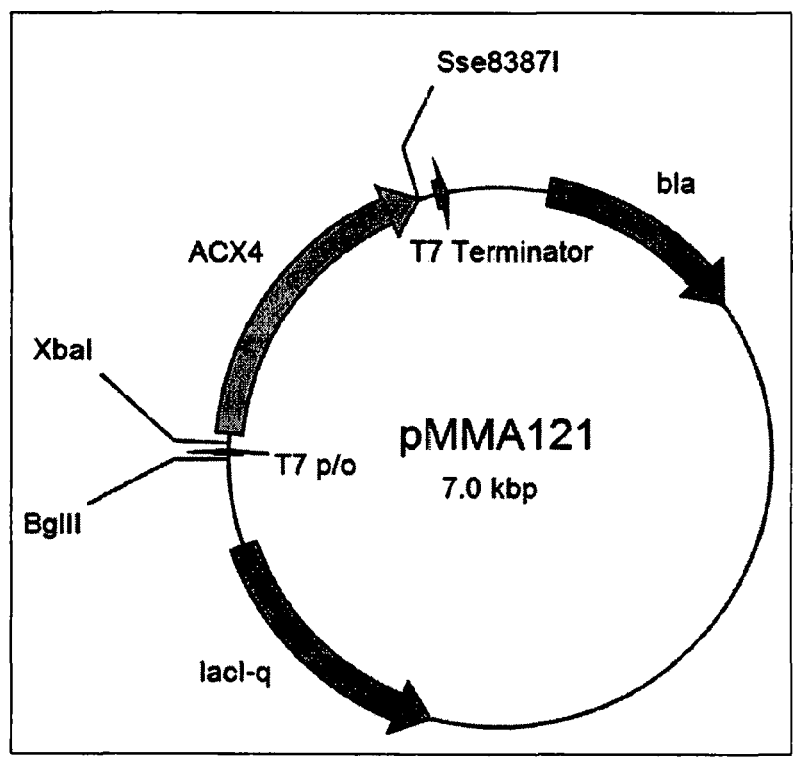

FIG. 20 shows the structure of plasmid pMMA121 for expression of the *Arabidopsis thaliana* ACX4 protein in *E. coli*.

Figure 21:
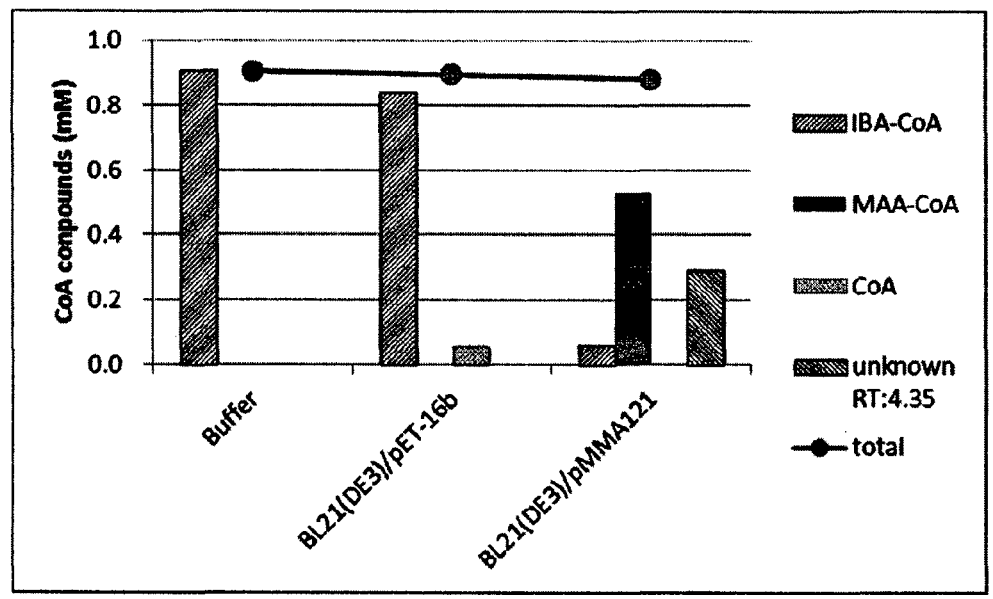

FIG. 21 shows the production of methacrylyl-CoA from isobutyryl-CoA using the *Arabidopsis thaliana* ACX4 protein produced from recombinant *E. coli* of example 5.

Figure 22:
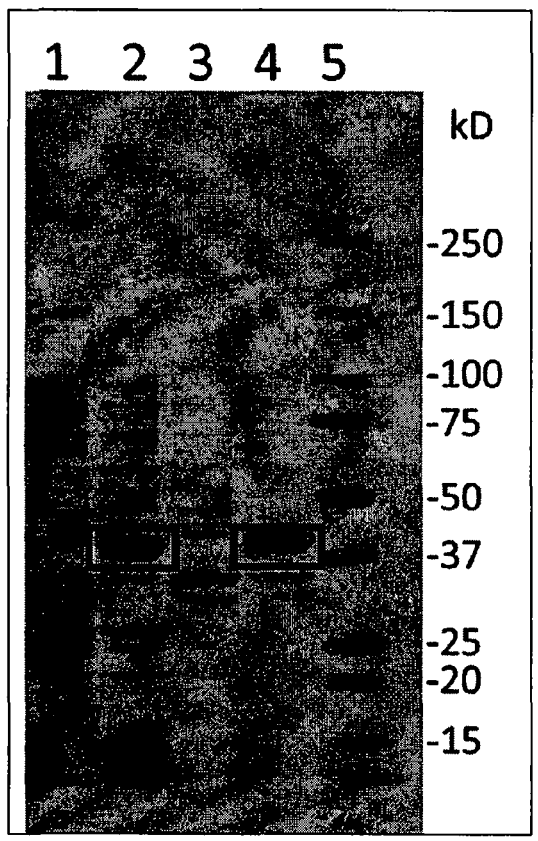

FIG. 22 shows the SDS-PAGE analysis of fractions of the recombinant *E. coli* of example 5 containing the *Arabidopsis thaliana* ACX4 protein.

Figure 23:
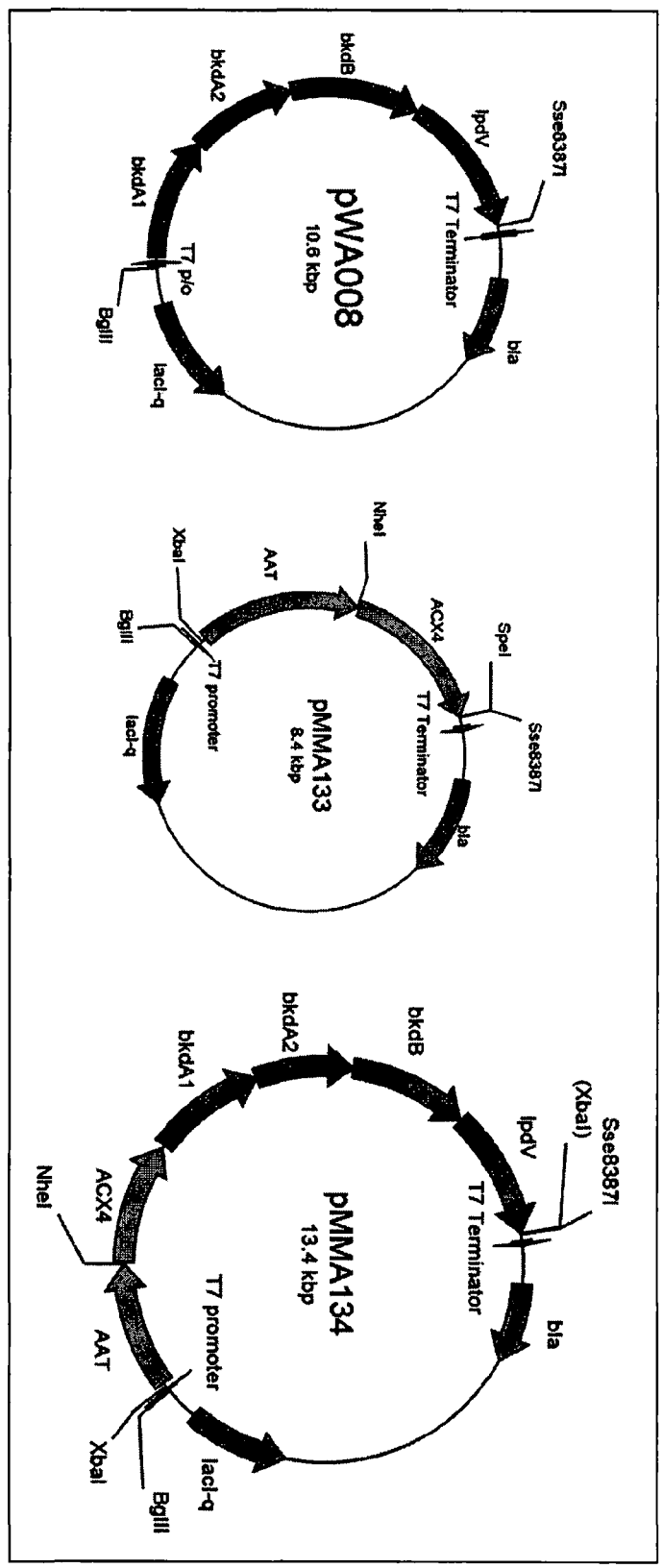

FIG. 23 shows the structure of plasmids pWA008, pMMA133 and pMMA134 for the expression of apple AAT (MpAAT1), ACX4 from *Arabidopsis*, and bkdA1, bkdA2, bkdB and IpdV: BCKAD complex genes from *Pseudomonas aeruginosa* PA01 strain in recombinant *E. coli*.

Figure 24:
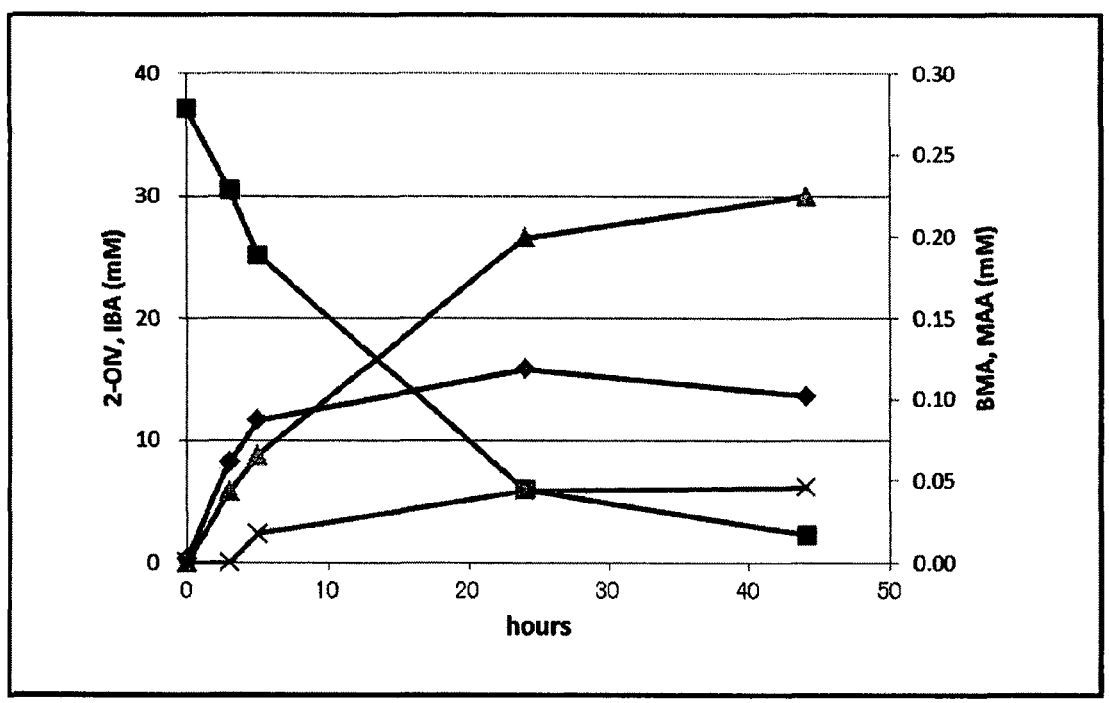

FIG. 24 shows the production of butyl methacrylate from 2-ketoisovalerate and butanol by HPLC analysis of a sample of the culture of recombinant *E. coli* production expressing plasmid pMMA134.

Example 1: The selective hydrolysis of methacrylyl-CoA

Example 2: The oxidation of isobutyryl-CoA to methacrylyl-CoA and the in vitro conversion of isobutyryl-CoA to methacrylic acid and coenzyme A in an enzyme coupled reaction.

Example 3: The whole cell biotransformation of isobutyric acid to methacrylic acid.

Example 4: The whole cell production of methacrylic acid from glucose via a 2-ketoisovalerate intermediate.

Example 5: The whole cell production of butyl methacrylate from 2-ketoisovalerate by recombinant *Escherichia coli*

1.1 Materials for Examples 1 to 4

The bacterial strains used throughout examples one to four are listed, as well as the growth media and agar plates used throughout the experiments. A table of primers lists all the primers used in this study, and a table of plasmids lists all the plasmids used and constructed during this study.

1.1.1 Bacterial Strains

*E. coli* JM107 was used as a plasmid cloning host whilst *E. coli* BL21 (DE3) pLysS was used as a gene expression host.

1.1.2 Bacterial Growth Media and Nutrient Agar Plates 1.1.2.1 Luria Bertani Broth (LB Media)

Luria Bertani high salt media (Melford) (25 g·L$^{-1}$) was used wherever LB media is referred to, whereby 25 g of LB high salt media in 1 litre consists of peptone from casein digest (10 g·L$^{-1}$), yeast extract (5 g·L$^{-1}$) and sodium chloride (10 g·L$^{-1}$). LB media was often supplemented with carbenicillin (50 μg·ml$^{-1}$), chloramphenicol (34 μg·ml$^{-1}$) and/or glucose (1% w/v). LB media was sterilised by autoclave, whilst stock solutions of glucose (20% w/v) in water, carbenicillin (100 mg·ml$^{-1}$) in water and chloramphenicol (34 mg·ml$^{-1}$) in ethanol were filter sterilised and added separately.

1.1.2.2 MSX Minimal Media

MSX media was prepared by combining MSA media (760 ml·L$^{-1}$), MSB media (200 ml·L$^{-1}$) and a 12.5% (w/v) glucose stock solution (40 ml·L$^{-1}$) at room temperature. MSB media was composed of $NH_4Cl$ (15 g·L$^{-1}$) and $MgSO_4.7H_2O$ (2.0 g·L$^{-1}$) and was sterilised by autoclave. MSA media was composed of $KH_2PO_4$ (7.89 g·L$^{-1}$), vishniac trace elements (2.63 ml·L$^{-1}$) and KOH solution was added until the pH reached 7.0 before MSA was sterilised by autoclave. Vishniac trace elements were prepared as previously described (Vishniac W, Santer M. THE THIOBACILLI, Bacteriological Reviews 1957; 21(3):195-213.) but using only 3.9 g·L$^{-1}$ of $ZnSO_4.7H_2O$. The glucose was filter sterilised using a 0.22 μm sterile filter. MSX media was sometimes supplemented with riboflavin (1 mg·L$^{-1}$) and this was achieved by dissolving riboflavin into MSB media first (5 mg·L$^{-1}$). This solution was then filter sterilised and the MSB+Riboflavin solution was then mixed with MSA and glucose in the same volumetric as for MSX media alone, to form MSX supplemented with riboflavin. Both MSX and MSX supplemented with riboflavin were always supplemented with carbenicillin (50 μg·ml$^{-1}$) and chloramphenicol (34 μg·ml$^{-1}$), prepared as previously described for LB media.

1.1.2.3 Luria Bertani Agar Plates

Luria Bertani agar plates were prepared using Luria Bertani high salt media (Melford) (25 g·L$^{-1}$) and agar (20 g·L$^{-1}$). The LB and agar mixture was sterilised by autoclave and allowed to cool for 1 h in a 50° C. water bath prior to pouring. The LB agar plates were often supplemented with carbenicillin (50 μg·ml-1), chloramphenicol (34 μg·ml-1) and/or glucose (1% w/v). The carbencillin, chloramphenicol and glucose stock solutions were prepared as previously described for Luria Bertani liquid broth and added to the LB agar solution just prior to pouring. The glucose stock solution was pre-warmed in a 50° C. water bath for 1 h prior to its addition to the LB agar.

1.1.3 Table of Primers and List of Sequences

| REF | PRIMER SEQUENCE (5' to 3') | SEQ ID |
|---|---|---|
| HHT.F | TATACATATGCACCGTACCTCTAACGGTTCTCACGC | 2 |
| HHT.R | CTCGAGTCCGTCACGACGCGGACG | 3 |
| OE.A.F | ACATATGCACCGTACCTCTAACGGTTC | 7 |
| OE.A.R | CTGCCATATCTATATCTCCTGTTAGTCACGACGCGGACG | 8 |
| OE.B.F | GTGACTAACAGGAGATATAGATATGGCAGTTCTGAGCAGC | 9 |
| OE.B.R | CTCGAGATATTATAGCTAGCTTACAGACGGCTACGGGTTG | 10 |
| BCKAD.F | GGCCTGTCATGAGTGATTACGAGCCG | 16 |
| BCKAD.R | CGGCCCTGCAGGTTCGCGGGAATCAGATGTGC | 17 |
| AAT.F | AGGAGATATACCATGAAAAGCTTTTCTGTACTC | 18 |
| AAT.R | AGCAGCCGGATCCCCTGCAGGACTAGTTTACTGGCTGGTGCTAC | 19 |
| ACX4.F | CACCAGCCAGTAAGCTAGCAAGGAGATATACCATGGCTG | 20 |
| ACX4.R | TCCCCTGCAGGACTAGTTTACAGGCGAGAACGGGTAG | 21 |

SEQ ID NO.1—codon optimised gene sequence for 4-Hydroxybenzoyl-CoA Thioesterase (4HBT) from *Arthobacter* sp. strain SU for expression in *Escherichia coli*.

SEQ ID NO.4—The product of the polymerase chain reaction performed to modify the 4HBT gene such that sub-cloning the PCR product into the pET20b(+) plasmid to form the pET20b(+)::CtHis-4HBT plasmid.

SEQ ID NO.5—The gene encoding the carboxy-terminal histidine tagged 4HBT enzyme in the pET20b(+)::CtHis-4HBT plasmid.

SEQ ID NO. 6—codon optimised gene encoding short chain acyl-CoA oxidase (ACX4) from *Arabidopsis thaliana* for expression in *Escherichia coli*.

SEQ ID NO.11—The product of the overlap extension polymerase chain reaction to concatenate 4HBT and ACX4 into one polynucleotide SEQ ID NO.12—codon optimised gene encoding acyl-CoA synthetase (AcsA) from *Pseudomonas chlororaphis* B23 for expression in *Escherichia coli*.

SEQ ID NO.13—The sequence between, and inclusive of, the NdeI and XhoI restriction sites in pET20b(+)::4HBT-ACX4-AcsA.

SEQ ID NO 14—The 'ppBCKD' polynucleotide synthesised by Biomatik containing the four genes encoding the subunits of the *Pseudomonas putida* KT2440 branched chain keto acid dehydrogenase, delivered in the pBSK::ppBCKD plasmid.

SEQ ID NO.15—The sequence between, and inclusive of, the NdeI and XhoI restriction sites in the pET20b(+)::4HBT-ACX4-ppBCKD plasmid.

SEQ ID NO. 22—The sequence of the pET16b (Sse) expression vector containing a modified Sse8387I restriction site.

SEQ ID NO. 23—codon optimised gene encoding short chain acyl-CoA oxidase (ACX4) from *Arabidopsis thaliana* for expression in the pET16b (Sse) expression vector.

SEQ ID NO. 24—codon optimised gene encoding alcohol acyl transferase (AAT) from Apple for expression in the pET16b (Sse) expression vector.

Table of plasmids

| PLASMID REFERENCE | SOURCE | DESCRIPTION |
|---|---|---|
| pBMH::4HBT | Biomatik Corporation | A cloning vector conferring resistance to ampicillin containing a codon optimised gene encoding 4HBT flanked by the NdeI and NotI restriction sites. |
| pBMH::AcsA | Biomatik Corporation | A cloning vector conferring resistance to ampicillin containing a codon optimised gene encoding AcsA flanked by a 3' XhoI restriction site and a 5' sequence containing an NheI restriction site, a ribosome binding site, a spacer sequence and an NdeI restriction site. |
| pBSK::ppBCKD | Biomatik Corporation | A cloning vector with the four genes encoding the branched chain keto acid dehydrogenase complex of *Pseudomonas putida* KT2440, flanked by a 3' XhoI restriction site and a 5' sequence composed of an XbaI restriction site, a spacer sequence, an NheI restriction site, a ribosome binding site and a second spacer sequence. |
| pMA-RQ::ACX4 | Life Technologies | A cloning plasmid conferring resistance to ampicillin, and containing a codon optimised gene encoding ACX4 from *Arabidopsis thaliana*, flanked by a 5' NdeI and a 3' XhoI restriction site. |
| pJET1.2 | Thermo Scientific | The pJET1.2 linearised blunt end cloning vector by Thermo Scientific. |
| pJET1.2::CtHIS-4HBT | This work | The pJET1.2 cloning vector containing the product of a polymerase chain reaction to replace the stop codon of 4HBT with a 5'-GGA-3' sequence followed by a XhoI site, such that on sub-cloning the insert into pET20b(+), the gene formed encodes 4HBT with a C-terminal His-tag appended to the end, with a tripeptide linker in between. |
| pJET1.2::4HBT-ACX4 | This work | The pJET1.2 cloning vector containing the product of an overlap extension |

Table of plasmids

| PLASMID REFERENCE | SOURCE | DESCRIPTION |
| --- | --- | --- |
| | | polymerase chain reaction that linked the 4HBT and ACX4 genes into a single polynucleotide with a new ribosome binding site in between the two genes. |
| pET20b(+) | Novagen | The pET20b(+) expression vector by Novagen. |
| pET20b(+)::4HBT | This work | The pET20b(+) expression vector containing the codon optimised gene encoding 4HBT from *Arthrobacter* sp. strain SU between the NdeI and NotI restriction sites. |
| pET20b(+)::CtHIS-4HBT | This work | The pET20b(+) expression vector with the insert from pJET1.2::CtHIS-4HBT subcloned in between the NdeI and XhoI restriction sites, for the expression of 4HBT with a Gly-Leu-Glu-His-His-His-His-His peptide appended to the carboxy-terminus of each subunit. |
| pET20b(+)::ACX4 | This work | The pET20b(+) expression vector containing the codon optimised gene encoding short chain acyl-CoA oxidase from *Arabidopsis thaliana*, cloned in between the NdeI and XhoI restriction sites. |
| pET20b(+)::AcsA | This work | The pET20b(+) expression vector containing the codon optimised gene encoding AcsA, cloned in between the NdeI and XhoI restriction sites. |
| pET20b(+)::4HBT-ACX4 | This work | The pET20b(+) expression vector containing the 4HBT and ACX4 genes subcloned as a single polynucleotide from the pJET1.2::4HBT-ACX4 plasmid into the pET20b(+) plasmid in between the NdeI and XhoI restriction sites, such that an expression unit is formed for the co-expression of both 4HBT and ACX4, and capable of accepting a second insert between the newly introduced NheI site and the XhoI site. |
| pET20b(+)::4HBT-ACX4-AcsA | This work | The pET20b(+)::4HBT-ACX4 expression vector containing the AcsA gene subcloned from the pBMH::AcsA plasmid in between its NheI and XhoI sites. |
| pET20b(+)::ppBCKD | This work | The pET20b(+) expression vector containing the four genes encoding the ppBCKD complex, subcloned from the pBSK::ppBCKD plasmid in between the XbaI and XhoI restriction sites. |
| pET20b(+)::4HBT-ACX4-ppBCKD | This work | The pET20b(+)::4HBT-ACX4 expression vector containing the four genes encoding the ppBCKD complex, subcloned from the pBSK::ppBCKD plasmid into it in between its NheI and XhoI restriction sites. |
| pET16b (Sse) | This work | The pET16b expression vector with a modified Sse8387I restriction site. |
| pMMA121 | This work | The pET16b (Sse) expression vector containing the ACX4 gene from *A. thaliana* optimised for expression in pET16b (Sse) between its XbaI and Sse8387I restriction sites. |
| pWA008 | This work | The pET16b(Sse) expression vector containing the operon which encodes the BCKAD complex from *P. aeruginosa* PA01 strain inserted between its NcoI and Sse8387I restriction sites. |
| pAAT212 | This work | The pET(Sse) expression vector containing the AAT gene from Apple optimised for expression in pET16b (Sse) inserted between its NcoI and Sse8387I restriction sites |
| pMMA133 | This work | The pAAT212 plasmid further containing the ACX4 gene from *A. thaliana* optimised for expression in the pET16b (Sse) vector inserted between the SpeI restriction site and the AAT gene. |
| pMMA134 | This work | The pMMA133 and the pWA008 plasmids ligated together and containing the ACX4 gene from *A. thaliana* optimised for expression in the pET16b (Sse) vector, the AAT gene from Apple optimised for expression in the pET16b (Sse) vector, and the BCKAD complex from *P. aeruginosa* PA01 strain inserted between the XbaI and Sse8387I restriction sites. |

1.2 General Methods for Examples 1 to 4

1.2.1 Transformation of Plasmids into *E. coli* JM107 Cloning Host.

Plasmids (1 ng) were transformed into *E. coli* JM107 (541) that was made competent using the Fermentas TransformAid™ bacterial transformation kit. Freshly transformed cells were incubated on ice for 5 min, then plated on prewarmed LB agar plates supplemented with carbenicillin (50 ng·µl$^{-1}$). Plates were incubated at 37° C. for 16 h.

1.2.2 Restriction Digests of Plasmids

To isolate the gene or polynucleotide inserts from plasmids, restriction digests of plasmids were performed using the Fermentas FastDigest® series of restriction endonucleases, according to the instructions provided. All restriction digest reactions were performed in a water bath at 37° C. for 3 h.

1.2.3 Preparation of Linear Expression Vector

Plasmids were linearised in restriction digestion reactions (100 µl) containing plasmid DNA (100 ng·µl$^{-1}$), Fermentas FastDigest® Green buffer (1×) and Fermentas FastDigest® restriction endonucleases, as described above. Linearised vectors were purified by agarose gel electrophoresis and gel extraction without first heat-inactivating the restriction endonucleases. The 5' phosphates of the linearised vectors were then hydrolysed by Antarctic phosphatase (New England Biolabs) according to the instructions provided. The dephosphorylated vector was concentrated by ethanol precipitation, which required the addition of 3M sodium acetate, pH 5.2, to the sample (volume added: $\frac{1}{10}^{th}$ of the original sample volume) followed by the addition of absolute ethanol (volume added: 2× the new sample volume). The precipitation mixture was incubated overnight at −20° C. The precipitated DNA was then centrifuged in an Eppendorf miniSpin F-45-12-11 rotor at 13400 rpm for 30 min. The supernatant was discarded and the cell pellet was washed with 70% (v/v) ethanol. The DNA pellet was then centrifuged in the same rotor and at the same speed as before for a further 10 min. The supernatant was removed and the DNA pellet was air dried in a fume hood for 20 min before being resuspended in nuclease free water (50 µl). The concentration of the linearised vector was determined by analytical agarose gel electrophoresis.

1.2.4 Agarose Gel Electrophoresis and Gel Extraction

Linear DNA fragments from plasmid digestion or PCR amplification were purified by agarose gel electrophoresis. The digests or PCR products were loaded onto an agarose gel consisting of agarose (1% (w/v)), ethidium bromide (1.78 µM), Tris acetate (4 mM) and ethylenediaminetetraacetic acid (EDTA) (1 mM). A potential difference of 7V per centimetre of gel length was applied across the gel to resolve the polynucleotides. DNA was visualised on the gel with a transluminator, and a gel slice containing the polynucleotide of interest was excised with a scalpel. The polynucleotide was purified from the gel slice with the QIAquick® Gel extraction kit. The concentration of the polynucleotide was determined by analytical agarose gel electrophoresis.

1.2.5 Ligation of Inserts into Linearised Plasmids

Gene inserts were ligated into linearised plasmid in a ligation reaction (20 µl). Ligation reactions consisted of gene insert and linear vector (50 ng) in a 3:1 molar ratio for gene inserts less than 3 kb in length, or a 1:1 molar ratio for gene inserts greater than 3 kb in length, along with T4 DNA ligase (1 unit) and Fermentas buffer for T4 DNA ligase (1×). Ligations were performed at room temperature for 20 min and ligation mixture (2.5 µl) was used as the source of plasmid for the transformation into *E. coli* JM107, which was performed using the Fermentas TransformAid bacterial transformation kit, as before. Transformed cells were plated on prewarmed LB agar plates supplemented with carbenicillin and were incubated at 37° C. for 16 h.

1.2.6 Subcloning a Polynucleotide into an Expression Vector

To sub-clone a polynucleotide into a new vector, the source vector was first amplified by transforming it (1 ng) into *E. coli* JM107 using the Fermentas TransformAid™ bacterial transformation kit and then preparing an LB culture (5 ml) supplemented with carbenicillin for each of 5 unique colonies on the agar plate. The 5×5 ml LB+Carbenicillin cultures were incubated at 37° C. with shaking at 250 rpm for 16 h and plasmids were purified out of the culture using the QIAGEN QIAprep® Spin miniprep kit as described in the manual. The polynucleotides of interest were digested out of each plasmid preparation in restriction digest reactions (20 µl) using 1 µl of the required restriction endonuclease for each of the desired 5' and 3' cloning sites. The restriction digests were pooled together and the polynucleotide to be subcloned into the new vector was purified from the remainder of the source vector by agarose gel electrophoresis and gel extraction. A ligation reaction was established to ligate the polynucleotide insert into a linearised expression vector previously prepared with complementary cohesive ends to the insert. The ligation reaction (2.5 µl) was used as the source of plasmid for transformation into *E. coli* JM107, as already described. The expression plasmid was amplified by inoculating an LB+Carbenicillin culture (100 ml) with a single colony from the plate of transformants, incubating the culture at 37° C. with shaking at 200 rpm for 16 h, and purifying the plasmid from the culture using the QIAGEN Plasmid MidiPrep kit.

1.2.7 Transformation of *E. coli* BL21 (DE3) pLysS with Expression Vector

Expression vector (1 ng) was transformed into *E. coli* BL21 (DE3) pLysS expression host. Competent cells were purchased from Novagen, and ice cold circular plasmid (1 ng) was added to ice cold competent cells (20 µl). The transformation mixture was incubated on ice for 5 min prior to a 30 s heat shock at 42° C. After the heat shock, cells were incubated on ice for a further 2 min. SOC media (Novagen) (80 µl) was added to the transformed cells and the cells were incubated at 37° C. with shaking at 250 rpm for 60 min prior to plating on LB agar plates supplemented with carbenicillin (50 µg·ml$^{-1}$), chloramphenicol (34 µg·ml$^{-1}$) and glucose (1%, w/v). Plates were incubated at 37° C. for 16 h.

1.2.8 Analytical Agarose Gel Electrophoresis

Linear DNA homogeneity and concentration was determined by analytical agarose gel electrophoresis. Agarose gels consisted of agarose (1% (w/v)), ethidium bromide (1.78 µM), Tris acetate (4 mM) and EDTA (1 mM). A fixed volume (5 µl) of DNA sample was loaded onto the gel alongside GeneRuler™ 1 kb Plus DNA ladder (Thermo Scientific) (5 µl). To estimate the concentration of the sample, the intensity of the sample band was visually compared to the intensities of bands of similar size and known mass in the ladder, as described in the manual for the GeneRuler™ 1 kb Plus DNA ladder.

1.2.9 Sodium-Dodecyl-Sulphate Polyacrylamide Gel Electrophoresis

Samples (1.5 ml) were taken from cell culture and cells were pelleted by centrifugation at 5000 g for 10 min. Cell pellets were resuspended in cell lysis buffer, using 100 µl for each OD$_{600}$ unit the cell culture was at when the samples were taken. Cell lysis buffer contained potassium phosphate buffer (100 mM, pH 7.5), BugBuster cell lysis detergent (Merck-Millipore) (1×), Benzonase nuclease (Sigma Aldrich) (0.01%, v/v) and protease inhibitor cocktail (Roche). Resuspended cells were incubated for 20 min with shaking at 250 rpm and centrifuged at 18,000 g for 20 min at 4° C. The insoluble fraction was re-suspended in potassium phosphate buffer (100 mM, pH 7.5) using the same volume as was used to resuspend the cell pellet. Soluble and insoluble fractions were mixed in a 1:1 ratio with 2× Laemmli sample buffer (Bio-Rad), containing β-mercaptoethanol (5%, v/v). Samples were boiled at 100° C. for 5 min and loaded onto a Bio-Rad AnyKD TGX precast gel. Electrophoresis was performed at 200V in Tris/Glycine/SDS running buffer (Bio-Rad). Gels were washed by soaking them in double distilled water at room temperature with gentle agitation (50 rpm) for 5 min. The water was removed and the wash procedure was repeated a further four times. Gels were then stained by soaking overnight (16 h) in EZBlue™ Gel Staining Reagent (Sigma-Aldrich) at room temperature with gentle agitation for 16 h.

1.3 Example 1—Production of Methacrylic Acid from Methacrylyl-CoA

The enzyme 4-hydroxybenzoyl-CoA thioesterase (4HBT) from *Arthrobacter* sp. strain SU (Genbank accession number AAC80224.1, Uniprot accession number Q04416, EC number 3.1.2.23) was identified as a candidate thioesterase for the hydrolysis of methacrylyl-CoA after a database and literature search for thioesterases with known activity on substrates that are structurally related to methacrylyl-CoA.

A gene encoding the amino acid sequence for 4HBT was codon optimised for expression in *E. coli* and synthesised by Biomatik Corporation with an NdeI restriction site integrated into the 5' end and a NotI restriction site appended to the 3' end.

The synthesised polynucleotide (SEQ. ID 1) was delivered in the pBMH::4HBT cloning vector and the 4HBT gene insert was sub-cloned into a previously linearised pET20b (+) expression vector, at the NdeI and NotI restriction sites, to form pET20b(+)::4HBT. The newly constructed pET20b (+)::4HBT plasmid was then transformed into *E. coli* BL21 (DE3) pLysS to form *E. coli* BL21 (DE3) pLysS pET20b (+)::4HBT.

To express the 4-hydroxbenzoyl-CoA thioesterase enzyme, a starter culture (20 ml) of LB media supplemented with glucose, carbencillin and chloramphenicol was first inoculated with a single colony of *E. coli* BL21 (DE3) pLysS pET20b(+)::4HBT from an LB agar plate supplemented with glucose chloramphenicol and carbenicillin. The starter culture was incubated at 37° C. with shaking at 200 rpm until the culture reached an $OD_{600}$ of 1.0. The cells were then harvested by centrifugation at 5000 g for 15 min at 4° C. and used to inoculate an intermediate culture (100 ml) of LB media, also supplemented with glucose, carbenicillin and chloramphenicol. The intermediate culture was also incubated at 37° C. with shaking at 200 rpm until an $OD_{600}$ of 1.0. The cells in the intermediate culture were then harvested by centrifugation at 5000 g for 15 min at 4° C. before being re-suspended into fresh LB media (1 L), again supplemented with glucose, carbenicillin and chloramphenicol, in a 2.5 L baffled shake flask. This culture was incubated at 37° C. with shaking at 200 rpm until an $OD_{600}$ of 1.0 and expression of 4HBT was then induced by the addition of isopropyl-3-D-thiogalactopyrannoside (IPTG) to a final concentration of 0.4 mM. The culture was incubated for a further 5.5 h under the same conditions. The culture was divided evenly into three centrifuge tubes and cells were then harvested by centrifugation at 5000 g for 20 min at 4° C. A sample of the culture taken prior to the cells being harvested was analysed by SDS-PAGE which showed the protein to be highly soluble and well expressed. Cell pellets in each centrifuge tube were washed three times in assay buffer (50 ml), which comprised of 2-[4-(2-hydroxyethyl) piperazin-1-yl])ethanesulfonic acid (HEPES) (50 mM), that was adjusted to pH 7.5 with potassium hydroxide. The cell pellets were frozen at −80° C. until lysed. This process was repeated for the *E. coli* BL21 (DE3) pLysS pET20b(+), an empty pET20b(+) vector negative control strain.

To prepare a cell free extract of the 4HBT enzyme, one of the cell pellets of *E. coli* BL21 (DE3) pLysS pET20b(+):: 4HBT that was prepared previously was re-suspended in HEPES (50 mM, pH 7.5) assay buffer and lysed in a Constant Systems One Shot cell disrupter. The cell lysate was centrifuged at 18,000 g for 15 min at 4° C. and the supernatant of this was centrifuged at 57,750 g for a further 60 min at 4° C. This supernatant was washed using a VivaSpin Viva6 10,000 Molecular Weight Cut-Off centrifugal concentrator, centrifuging at 10,000 g at 18° C. until a six-fold volume reduction, followed by a six-fold re-dilution in the HEPES assay buffer and a further 6-fold volume reduction in the centrifugal concentrator. The total protein concentration of the cell free extracts from *E. coli* BL21 (DE3) pLysS pET20b(+)::4HBT overexpression cultures was performed using the BioRad DC assay kit, using bovine serum albumin as the protein standard. The same procedure was followed in order to prepare cell free extracts from a cell pellet of the *E. coli* BL21 (DE3) pLysS pET20b(+), the negative control strain.

In order to assay the 4HBT enzyme for activity on methacrylyl-CoA, methacrylyl-CoA was first prepared. The synthesis of methacrylyl-CoA was performed by the reaction of coenzyme A with methacrylic anhydride. The reaction consisted of coenzyme A (20 mM) and methacrylic anhydride (40 mM) in sodium phosphate buffer (100 mM, pH 8.5). The reaction was incubated on ice and vortexed every 2 min for 30 min and the final reaction mix was acidified to pH 3.5 with hydrochloric acid. Methacrylic acid byproduct and unreacted methacrylic anhydride were removed by extraction with 4×10 ml water saturated diethyl ether. Methacrylyl-CoA was purified by reverse phase high performance liquid chromatography (RP-HPLC) on an analytical scale column (Agilent Zorbax Eclipse XDB C18 column, 4.6 mm×150 mm). Sample (75 µl) was injected onto the C18 column, and eluted over 40 min by a linear acetonitrile gradient (1.8%-13.5%) in 0.1% trifluoroacetic acid (TFA), at a flowrate of 1 ml·$min^{-1}$. The main peak was the methacrylyl-CoA containing peak, and the methacrylyl-CoA containing fractions were collected and pooled. Acetonitrile was removed by rotary evaporation (21° C., 3 kPa), leaving behind an aqueous solution of methacrylyl-CoA and trifluoroacetic acid. This solution of methacrylyl-CoA and trifluoroacetic acid was brought to pH 7 by sodium hydroxide and flash frozen with liquid nitrogen prior to lyophilisation. TFA was removed by re-dissolving the freeze dried sample in nuclease free water (10 ml), and repeating the freeze-dry-redissolve cycle twice more, once in 5 ml, and finally in 1 ml nuclease free water. The concentration of methacrylyl-CoA was determined by absorbance at 260 nm with a molar extinction coefficient of $16800 M^{-1} \cdot cm^{-1}$.

Crude enzymatic assays of 4HBT were performed in cuvettes (1 ml) containing cell free protein extract (1 mg·$ml^{-1}$), methacrylyl-CoA (approximately 100 µM), 5'5-dithiobis-(2-nitrobenzoic) acid (DTNB) (500 µM). Reactions were started by the addition of substrate and were monitored at 412 nm. Enzymatic assays were repeated for cell free extracts of *E. coli* BL21 (DE3) pLysS pET20b(+). Enzyme assays for cell free extracts of both the 4HBT overexpressing strain and the empty vector control strain were repeated for isobutyryl-CoA as a substrate also.

Crude enzyme assays of 4HBT demonstrated that 4HBT catalysed the hydrolysis of methacrylyl-CoA, and exhibited a selectivity for methacrylyl-CoA over isobutyryl-CoA as a substrate.

In order to better characterise 4-hydroxybenzoyl-CoA thioesterase, the enzyme was His-tagged so that it could be assayed as a pure enzyme as opposed to as a part of a cell free extract. To His-tag the enzyme, a polymerase chain reaction was established. Forward and reverse primers for 4HBT His-tagging, HHT.F (SEQ. ID 2) and HHT.R (SEQ. ID 3), were designed to replace the (5'-TAA-3') stop codon from the gene encoding 4HBT with a (5'-GGA-3') sequence and to introduce a 3' XhoI restriction site immediately after. Thus, on cloning the PCR product back into pET20b(+) between the NdeI and XhoI restriction sites, an open reading frame encoding 4HBT with a glycine-leucine-glutamate spacer sequence and a carboxy-terminal hexahistidine (His) tag was created.

Polymerase chain reaction mixtures contained the pET20b(+)::4HBT plasmid as template DNA (50 pg·µl$^{-1}$), KOD DNA polymerase (1 unit), primer HHT.F (0.4 µM), primer HHT.R (0.4 µM), deoxyadenosinetriphosphate (dATP) (0.2 mM), deoxythymidine triphosphate (dTTP) (0.2 mM), deoxycytidinetriphosphate (dCTP) (0.2 mM), deoxyguanosinetriphosphate (dGTP) (0.2 mM), MgCl$_2$ (1 mM) and Novagen buffer #1 for KOD DNA polymerase (1×). PCR mixtures were loaded into a thermocycler programmed to start at 94° C. for 3 min, then to cycle through 30 iterations of 30 s melting at 94° C., 30 s annealing at 55° C., 80 s elongation at 72° C., before ending with 5 min at 72° C.

The PCR product (SEQ. ID 4) was purified by agarose gel electrophoresis followed by gel extraction, and was blunt end ligated into the pJET1.2 cloning vector to form pJET1.2::CtHis-4HBT. The insert was then sub-cloned from pJET1.2::CtHis-4HBT into pET20b(+) in between the NdeI and XhoI restriction sites to form pET20b(+)::CtHis-4HBT. The *E. coli* BL21 (DE3) pLysS expression host was then transformed with pET20b(+)::CtHis-4HBT to form the C-terminal hexahistidine tagged 4HBT expression host, *E. coli* BL21 (DE3) pLysS pET20b(+)::CtHis-4HBT.

Pure carboxy-terminal His-tagged 4HBT enzyme was then prepared by first growing cultures of *E. coli* BL21 (DE3) pLysS pET20b(+)::CtHis-4HBT and inducing expression in the exact same manner as was performed for *E. coli* BL21 (DE3) pLysS pET20b(+)::4HBT. A sample from the culture taken 5.5 h after expression showed that the carboxy-terminal His-tagged 4HBT enzyme was also very soluble and was expressed at high levels. Cells were harvested by splitting the cell culture into three centrifuge tubes and centrifuging at 5000 g for 20 min at 4° C. Cell pellets were not washed though, and were instead directly stored at −80° C. A cell free extract of carboxy-terminal hexahistidine tagged 4HBT was prepared by re-suspending one of the *E. coli* BL21 (DE3) pLysS pET20b(+)::CtHis-4HBT cell pellets in binding buffer (6 ml) for a Nickel-sepharose FPLC column. Binding buffer consisted of NaH$_2$PO$_4$ (10 mM), Na$_2$HPO$_4$ (10 mM), NaCl (500 mM), imidazole (30 mM) and was adjusted to pH 7.4 with HCl. Benzonase® nuclease (0.6 µl) was added to the re-suspended cells before they were lysed in the Constant Systems One Shot cell disrupter. The cell lysate was then clarified by centrifugation at 18,000 g for 15 min at 4° C., followed by centrifugation of the supernatant at 57,750 g for 60 min at 4° C. This supernatant was then loaded onto a GE Healthcare HisTrap™ FF Crude column (1 ml) that was equilibrated with binding buffer. Unbound proteins were washed off the column with five column volumes of binding buffer, and His-tagged protein was eluted with a linear imidazole concentration gradient, from 30 mM to 500 mM over 20 column volumes. Protein elution was monitored at 280 nm and fractions were checked for the presence and purity of carboxy-terminal His-tagged 4HBT by SDS-PAGE. Fractions containing pure CtHis-4HBT protein were pooled and a buffer exchange to replace the elution buffer with potassium phosphate assay buffer (100 mM, pH 7.5) was performed in a VivaSpin Viva6 10,000 Molecular Weight Cut-Off centrifugal concentrator. To perform the buffer exchange, the pooled fractions were centrifuged through the ultrafiltration membrane of the centrifugal concentrator at 10,000 g at 18° C. until the volume of the pooled fractions was reduced to 1 ml. The remaining protein fraction was diluted six-fold in the potassium phosphate assay buffer and the samples concentrated by further centrifugation through the ultrafiltration membrane under the same conditions until a six-fold volume reduction was achieved. The latter dilution in potassium phosphate assay buffer and re-concentration was performed once more and the concentration of CtHIS-4HBT protein was determined by UV$_{280}$ absorbance in a NanoDrop ND1000 spectrophotometer, using a molar extinction coefficient of 20970M$^{-1}$·cm$^{-1}$ and a molecular weight of 17516.5 mg·mmol$^{-1}$ for the carboxy-terminal His-tagged 4HBT enzyme. The values for the molar extinction coefficient and molecular weight were determined using the Expasy ProtParam tool, using the amino acid translation of the gene sequence encoding the carboxy-terminal his tagged 4HBT enzyme (SEQ. ID 5) in the pET20b(+)::CtHis-4HBT plasmid.

Kinetic characterisation of the purified carboxy-terminal hexahistidine tagged 4HBT enzyme was performed for the methacrylyl-CoA that was previously prepared, and for isobutyryl-CoA (Purchased from Sigma Aldrich as isobutyryl-CoA lithium salt).

Methacrylyl-CoA hydrolysis reactions (200 µl) were performed in Nunc 96 well plates using purified CtHis-4HBT protein (0.075 mg·ml$^{-1}$) and DTNB (0.5 mM) to monitor the reaction. Initial rates were determined for methacrylyl-CoA starting concentrations of 0.375 mM, 0.3 mM, 0.225 mM, 0.15 mM and 0.075 mM. The reactions were started by the addition of enzyme.

Isobutyryl-CoA hydrolysis reactions (200 µl) were also performed in Nunc 96 well plates, using purified CtHIS-4HBT protein (1 mg·ml$^{-1}$) and DTNB (0.5 mM) to monitor the reaction. Initial rates were determined for isobutyryl-CoA starting concentrations of 0.5 mM, 0.4 mM, 0.3 mM, 0.2 mM and 0.1 mM. The reactions were again started by the addition of enzyme.

Figure 1:
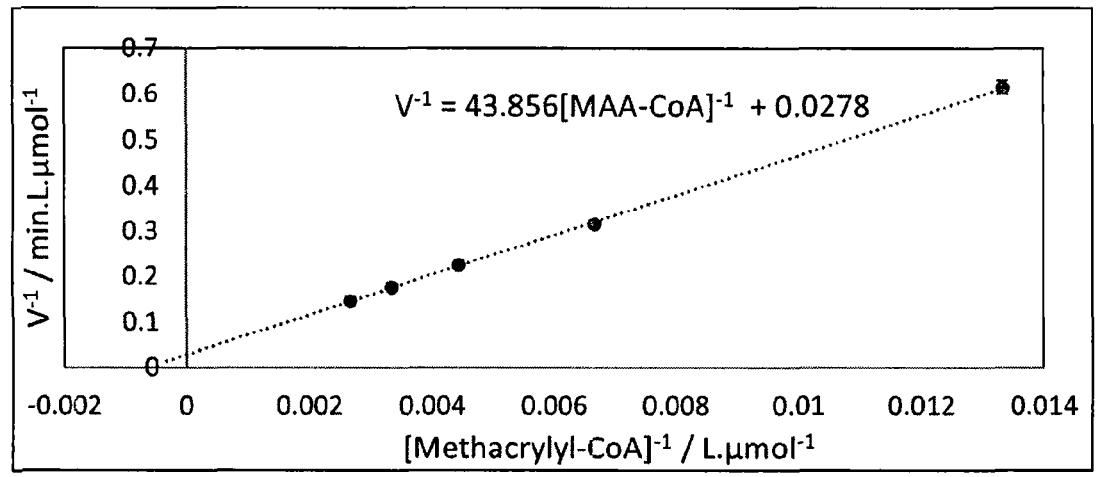
FIG. 1 shows a Lineweaver-Burke plot for the kinetic characterisation of carboxy-terminal hexahistidine tagged 4-hydroxybenzoyl-CoA thioesterase (75 μg·ml$^{-1}$) from *Arthrobacter* sp. SU with methacrylyl-CoA as a substrate.
Figure 2:
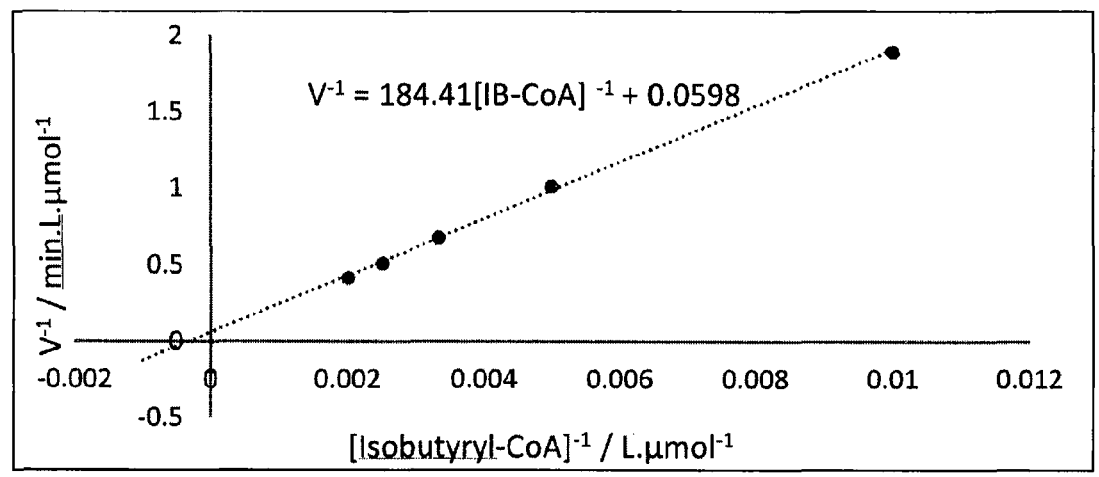
FIG. 2 shows a Lineweaver-Burke plot for the kinetic characterisation of carboxy-terminal hexahistidine tagged 4-hydroxybenzoyl-CoA thioesterase (1 mg·ml$^{-1}$) from *Arthrobacter* sp. SU with isobutyryl-CoA as a substrate.

Lineweaver-Burke plots were plotted for the kinetic characterisation of both methacrylyl-CoA (FIG. 1) and isobutyryl-CoA (FIG. 2). The kinetic constants for carboxy-terminal hexahistidine tagged 4HBT for methacrylyl-CoA were a $K_M$ of 1.6 mM and a $V_{max}$ of 470 nmols·mg$^{-1}$·min$^{-1}$, whereas for isobutyryl-CoA, they were a $K_m$ of 3 mM and a $V_{max}$ of 16.7 nmols·mg$^{-1}$·min$^{-1}$.

Thus, it has been demonstrated that 4HBT catalyses hydrolysis of methacrylyl CoA and can be used to produce methacrylic acid. Since 4HBT hydrolyses methacrylyl-CoA with lower $K_M$ values and higher $V_{max}$ values than for isobutyryl-CoA, the hydrolysis of methacrylyl-CoA by 4HBT is advantageously highly selective.

1.4 Example 2—Formation of Methacrylyl-CoA and Methacrylic Acid from Isobutyryl-CoA The enzyme short chain acyl-CoA oxidase (ACX4) from *Arabidopsis thaliana* (Genbank accession number AB017643.1, Uniprot accession number Q96329, EC number 1.3.3.6) was identified through a literature search as an acyl-CoA oxidase enzyme with detectable activity on isobutyryl-CoA as a substrate when expressed in insect cell lines.

To determine whether this oxidase could be functionally expressed in Escherichia coli with useful levels of activity on isobutyryl-CoA as a substrate for its integration into a metabolic pathway, a gene encoding the amino acid sequence for ACX4 was codon optimised for expression in E. coli by Life Technologies with an NdeI restriction site integrated at the 5' end and a XhoI restriction site at the 3' end.

The synthesised polynucleotide (SEQ. ID 6) was delivered in the µMA-RQ::ACX4 plasmid and the gene insert was subcloned into a previously linearised pET20b(+) vector, at the NdeI and XhoI restriction sites, to form pET20b(+)::ACX4. The newly constructed pET20b(+)::ACX4 plasmid was then transformed into E. coli BL21 (DE3) pLysS to form E. coli BL21 (DE3) pLysS pET20b(+)::ACX4.

In order to test the expression of ACX4, an MSX starter culture supplemented with carbenicillin and chloramphenicol was inoculated with a single colony of E. coli BL21 (DE3) pLysS pET20b(+)::ACX4 from an LB agar plate that was supplemented with glucose, chloramphenicol and carbenicillin. The starter culture (20 ml) was incubated at 37° C. with shaking at 200 rpm for 16 h. The cells were harvested from the starter culture by centrifugation at 5000 g for 15 min at 4° C. and then re-suspended into a fresh MSX media intermediate culture (100 ml) that was also supplemented with chloramphenicol and carbenicillin. The intermediate culture was incubated at 37° C. with shaking at 200 rpm until an $OD_{600}$ of 1.0. The cells were then harvested from the intermediate culture by centrifugation at 5000 g for 15 min at 4° C. and re-suspended into a fresh MSX culture (1 L) supplemented with chloramphenicol, carbenicillin and also with riboflavin, in a 2.5 L baffled shake flask. The culture was incubated at 37° C. with shaking at 200 rpm until an $OD_{600}$ of 0.7 and expression was then induced by the addition of IPTG to a final concentration of 0.4 mM. The culture was incubated for a further 7 h under the same conditions before cells were split into three centrifuge tubes and harvested by centrifugation at 5000 g for 20 min at 4° C. A sample of the culture taken prior to the cells being harvested and was analysed by SDS-PAGE, which showed the ACX4 protein to be well expressed and for approximately one third of the ACX4 protein to lie in the soluble fraction and two thirds in the insoluble fraction. The cell pellets were washed three times in HEPES buffer (50 mM) that was adjusted to pH 7.5 with KOH. The cell pellets were frozen at −80° C. until lysed. The process was repeated for the E. coli BL21 (DE3) pLysS pET20b(+) negative control strain.

To prepare a cell free extract of the ACX4 enzyme, one of the cell pellets that was prepared previously was re-suspended in HEPES (50 mM, pH 7.5) buffer (6 ml) that was supplemented with flavin adenine dinucleotide (FAD) at a final concentration of 10 µM. The re-suspended cells were then lysed in a Constant Systems One Shot cell disrupter. The lysate was centrifuged at 18,000 g for 15 min at 4° C. and the supernatant of this was further centrifuged at 57,750 rpm for 60 min at 4° C. The supernatant was concentrated in a VivaSpin Viva6 10,000 Molecular Weight Cut-Off centrifugal concentrator, centrifuging at 10,000 g at 18° C. until a six-fold volume reduction of the retentate. The retentate was washed once by a six-fold re-dilution in HEPES buffer (50 mM, pH 7.5) that was again supplemented with FAD (10 µM), followed by a second concentration step in the centrifugal concentrator through a six-fold volume reduction. The total protein concentration in the retentate was determined using the BioRad DC protein assay kit, using bovine serum albumin as the protein standard.

An analytical HPLC method was developed to resolve isobutyryl-CoA (IB-CoA), methacrylyl-CoA (MAA-CoA), flavin adenine dinucleotide (FAD), methacrylic acid (MAA) and coenzyme A (CoA-SH). Coenzyme A, methacrylyl-CoA and isobutyryl-CoA eluted at 11.0 min, 30.8 min and 32.2 min respectively. Coenzyme A, methacrylyl-CoA and isobutyryl-CoA each had a small tailing (minor) peak assocated with the main peak at 12 min, 31.6 min and 32.9 min, respectively (FIG. 3). Methacrylic acid eluted at 13.5 min, and FAD, used in the crude assays of ACX4 and as an internal standard for the isobutyryl-CoA and methacrylyl-Coa standards, eluted at 27.8 min.

To ensure that coenzyme A, methacrylic acid, isobutyryl-CoA and methacrylyl-CoA were not be confused with peaks from the cell free extract, a no-substrate control was performed, using ACX4 cell free extract (0.8 mg·ml$^{-1}$), purified CtHis-4HBT (0.6 mg·ml$^{-1}$) and FAD (10 µM) in HEPES buffer. No peaks were observed eluting at the coenzyme A, methacrylic acid, methacrylyl-CoA or isobutyryl-CoA elution times (FIG. 4).

The activity test of ACX4 was performed in 1.5 ml micro-centrifuge tubes. Crude enzyme reactions consisted of cell free ACX4 protein extract (0.8 mg·ml$^{-1}$), isobutyryl-CoA (500 µM) and flavin adenine dinucleotide (10 µM) in HEPES buffer (50 mM, pH 7.5). The reaction was incubated at 30° C. in the 1.5 ml micro-centrifuge tube, with shaking at 250 rpm for 30 min and the final reaction product was analysed by analytical HPLC (FIG. 5). Methacrylyl-CoA was the major product, with a peak at 30.7 min. The concentration of methacrylic acid formed during the crude enzyme assay was 74 µM.

In order to confirm that the methacrylyl-CoA peak was genuine, and that it was not an isobutyryl-CoA peak with a shifted elution time, the sample was spiked with isobutyryl-CoA and analysed by HPLC again. ACX4 was inactivated when the sample was acidified and this ensured that any additional isobutyryl-CoA would not be converted to methacrylyl-CoA. Indeed, the isobutyryl-CoA spiked sample showed not only the original methacrylyl-CoA peak, but also an additional peak at 32 min with the characteristic tail peak of isobutyryl-CoA (FIG. 6).

To determine whether methacrylic acid could be produced from isobutyric acid in an enzyme couple reaction, an experiment was established whereby crude ACX4 was incubated with purified CtHis-4HBT enzyme. The same cell free extract of ACX4 was used as the protein source for the ACX4, though pure CtHis-4HBT was prepared again, in the same manner as for its kinetic characterisation in example 1, but performing a buffer exchange into HEPES buffer (50 mM, pH 7.5) at the end, instead of the previously used phosphate buffer. Thus, crude ACX4 (0.8 mg·ml$^{-1}$) was co-incubated with pure CtHis-4HBT (0.6 mg·ml$^{-1}$) along with FAD (10 µM) and isobutyryl-CoA (500 µM) in HEPES buffer. The sample was incubated at 30° C. with shaking at 250 rpm for 30 min, and analysed by HPLC. Methacrylic acid and coenzyme A were the major products. The methacrylic acid peak was observed at 13.45 min whilst the coenzyme A major and minor peaks were observed at 11.1 min and 12.1 min, respectively. The concentration of methacrylic acid generated during the coupled enzyme reaction (FIG. 7) was 345 µM, 4.7 times greater than that during the crude ACX4 assay alone.

This confirms that ACX4 oxidises isobutyryl-CoA. It has further been demonstrated that the combination of ACX4 with 4HBT in vitro enables the conversion of isobutyryl-CoA to methacrylic acid to industrially applicable levels.

1.5 Example 3—a Whole Cell Biotransformation of Isobutyric Acid to Methacrylic Acid Further biotransformation of isobutyric acid to methacrylic acid using an acyl-CoA synthetase to activate isobutyric acid with coenzyme A to form isobutyryl-CoA is shown in the present example, and for the acyl-CoA oxidase ACX4 from *Arabidopsis thaliana* to oxidise isobutyryl-CoA to methacrylyl-CoA as well as for the acyl-CoA thioesterase 4HBT from *Arthrobacter* sp. strain SU to hydrolyse methacrylyl-CoA to methacrylic acid and coenzyme A is also shown.

The acyl-CoA synthetase AcsA from *Pseudomonas chlororaphis* B23 (Genbank accession number: BAD90933.1, uniprot accession number: Q5CD72) was identified from a database and literature search as an AMP-forming acyl-CoA synthetase capable of activating isobutyric acid to isobutyryl-CoA, with a published Michaelis constant ($K_m$) of 0.14 mM, and turnover number ($k_{cat}$) of 10.6 $s^{-1}$.

In this example, we demonstrate the construction of a pET20b(+) based vector, pET20b(+)::4HBT-ACX4-AcsA, for the co-expression of the genes encoding 4HBT, ACX4 and AcsA from a single operon under the control of the T7 promoter of pET20b(+), and its use to encode the metabolic pathway for the whole cell biotransformation of isobutyric acid to methacrylic acid.

The construction of the operon was performed in two stages. The first stage comprised the construction of a pET20b(+) based vector, pET20b(+)::4HBT-ACX4, for the co-expression of the genes encoding just 4HBT and ACX4, whilst the second stage involved sub-cloning the gene encoding AcsA into the pET20b(+)::4HBT-ACX4 vector, with its own ribosome binding site in place, in order to construct the final pET20b(+)::4HBT-ACX4-AcsA plasmid.

In order to construct the pET20b(+)::4HBT-ACX4 vector, the genes encoding 4HBT and ACX4 were first conjoined into a single polynucleotide, with a new ribosome binding site between the gene encoding 4HBT and that encoding ACX4, in order to ensure efficient translation of the latter. To conjoin the two genes together, an overlap extension polymerase chain reaction was performed. The overlap extension polymerase chain reaction was itself performed in two steps. First, the genes encoding 4HBT and ACX4 were amplified out of their respective expression vectors, pET20b(+)::4HBT and pET20b(+)::ACX4, in two separate polymerase chain reactions, reactions 'A' and 'B'.

The primers used for the overlap extension polymerase chain reaction were primer OE.A.F (SEQ. ID 7), the forward primer for overlap extension polymerase chain reaction A; primer OE.A.R (SEQ. ID 8), the reverse primer for polymerase chain reaction A; primer OE.B.F (SEQ. ID 9), the forward primer for overlap extension polymerase chain reaction B and finally, OE.B.R (SEQ. ID 10), the reverse primer for overlap extension polymerase chain reaction B. The overhang of primer OE.A.F was designed to maintain an NdeI restriction site at the 5' end of the new polynucleotides. The overhangs of primers OE.A.R and OE.B.F were designed to contain complementary sequences to each other in order to enable the concatenation of the two PCR products from reactions A and B. The complementary sequence was designed such that on the concatenation of the two PCR products, an intergenic sequence between the 4HBT gene and the ACX4 gene would be introduced, containing a new ribosome binding site for the latter gene. Finally, the overhang of primer OE.B.R was designed to contain two restriction sites, an NheI restriction site and a XhoI restriction site. This allowed for the concatenated polynucletide containing the 4HBT and ACX4 genes to be cloned into the pET20b(+) plasmid at its NdeI and XhoI restriction sites to form pET20b(+)::4HBT-ACX4 and for the AcsA gene to be cloned into the pET20b(+)::4HBT-ACX4 plasmid in between the NheI and XhoI restriction sites to form the pET20b(+)::4HBT-ACX4-AcsA plasmid. An adenine and thymine rich spacer sequence was included between the NheI and XhoI restriction sites in primer OE.B.R to lower the annealing temperature of the primer such that it closer matched those of the other primers, and to enable efficient double digestion at the adjacent NheI and XhoI restriction sites.

Polymerase chain reaction A (50 µl) contained pET20b(+)::4HBT (10 pg·µl$^{-1}$) as the template DNA, KOD DNA polymerase (1 unit), primer OE.A.F (0.4 µM), primer OE.A.R (0.4 µM), deoxyadenosinetriphosphate (dATP) (0.2 mM), deoxythymidine triphosphate (dTTP) (0.2 mM), deoxycytidinetriphosphate (dCTP) (0.2 mM), deoxyguanosinetriphosphate (dGTP) (0.2 mM), MgCl$_2$ (1 mM) and Novagen buffer for KOD DNA polymerase (1×).

Polymerase chain reaction B (50 µl) was composed of pET20b(+)::ACX4 (20 pg·µl$^{-1}$) as template DNA, KOD DNA polymerase (1 unit) primer OE.B.F (0.4 µM), primer OE.B.R (0.4 µM), dATP (0.2 mM), dTTP (0.2 mM), dCTP (0.2 mM), dGTP (0.2 mM), MgCl$_2$ (1 mM) and Novagen buffer for KOD DNA polymerase (1×).

Both PCR reactions were performed in parallel and under the same conditions, commencing with an initial denaturation step at 95° C. for 3 min, followed by 25 cycles consisting of a 15 s denaturation step at 98° C., a 2 s annealing step at 50° C. and a 20 s extension step at 72° C. These 25 cycles were followed by a further 5 min extension step at 72° C. The two double stranded PCR products, product A and product B, were purified by agarose gel electrophoresis and gel extraction, and their concentrations determined by analytical agarose gel electrophoresis.

PCR products A and B were then concatenated in a second polymerase chain reaction consisting of PCR product A (15 nM), PCR product B (15 nM), dATP (0.2 mM), dTTP (0.2 mM), dCTP (0.2 mM), dGTP (0.2 mM), MgCl$_2$ (1 mM), Novagen Buffer #1 for KOD DNA polymerase (1×), dimethylsulfoxide (5% (v/v)) and KOD DNA polymerase (8 nl/µl). The reaction was performed in a thermocycler programmed to start at 95° C. for 3 min and continue with 15 cycles of a 15 s denaturation step at 98° C., a 2 s annealing step at 50° C. and a 20 s extension step at 72° C., and to finally end with a further extension step lasting 5 min at 72° C.

After this PCR program, the outer forward primer and the outer reverse primer used in the amplification of A and B, respectively, were added directly from a concentrated stock (50 µM) to a final concentration of 0.5 µM. The modified PCR reaction mixture was then subjected to another round of PCR, with the thermocycler programmed to commence with an initial 3 min melting step at 95° C., and continue with 15 cycles consisting of a melting step lasting 15 s at 98° C., an annealing step lasting 2 s at 55° C. and an extension step lasting 20 s at 72° C., before finishing with a further extension step lasting 5 min at 72° C.

The product of this concatenation step (SEQ. ID 11) was purified by agarose gel electrophoresis and gel extraction, and was blunt end ligated into the pJET1.2 cloning vector to form pJET1.2::4HBT-ACX4. The polynucleotide containing the concatenated 4HBT and ACX4 genes were then subcloned into pET20b(+), forming pET20b(+)::4HBT-ACX4. The pET20b(+)::4HBT-ACX4 plasmid was then linearised by restriction digestion at the NheI and XhoI restriction sites.

For the next phase in the construction of the pET20b(+)::4HBT-ACX4-AcsA plasmid, a gene encoding the amino acid sequence of AcsA was codon optimised for expression in *E. coli* and synthesised by Biomatik corporation with a XhoI restriction site appended to the 3' end, and a short sequence appended to the 5' end. This sequence contained an NheI restriction site, a ribosome binding site, and a spacer sequence ending in a cytosine-adenine-thymine trinucleotide, which together with the start codon of AcsA encoded an NdeI restriction site.

The synthesised codon optimised AcsA polynucleotide (SEQ. ID 12) was delivered in the pBMH::AcsA cloning plasmid and the AcsA gene was sub-cloned along with its 5' ribosome binding site into the linearised pET20b(+)::4HBT-ACX4 vector, between the NheI and XhoI restriction sites, forming the pET20b(+)::4HBT-ACX4-AcsA plasmid (FIG. 8). This plasmid was then transformed into *E. coli* BL21 (DE3) pLysS, forming *E. coli* BL21 (DE3) pLysS pET20b (+)::4HBT-ACX4-AcsA. The sequence between, and inclusive of, the NdeI and XhoI restriction sites in the pET20b (+)::4HBT-ACX4-AcsA plasmid, is shown in SEQ ID NO 13.

In order to construct a strain for the expression of just the AcsA gene, the AcsA gene alone was sub-cloned out of the pBMH::AcsA cloning vector and into the pET20b(+) plasmid, in between the NdeI and XhoI restriction sites, forming pET20b(+)::AcsA. The pET20b(+)::AcsA plasmid was then transformed into *E. coli* BL21 (DE3) pLysS, forming *E. coli* BL21 (DE3) pLysS pET20b(+)::AcsA.

The co-expression of 4HBT, ACX4 and AcsA by *E. coli* BL21 (DE3) pLysS pET20b(+)::4HBT-ACX4-AcsA was confirmed by incubating cultures (100 ml) of *E. coli* BL21 (DE3) pLysS pET20b(+)::4HBT-ACX4-AcsA in MSX media supplemented with riboflavin (1 mg·L$^{-1}$) at two different test temperatures, 37° C. and 28° C. Cultures were grown to an $OD_{600}$ of 0.5 and expression was induced with the addition of IPTG (0.4 mM). Samples were taken just prior to the induction of expression, as well as 1 h, 3 h, 5 h and 20 h post induction. Control strains *E. coli* BL21 (DE3) pLysS pET20b(+)::ACX4, as prepared in example 2, and *E. coli* BL21 (DE3) pLysS pET20b(+)::AcsA were also cultured under the same conditions. Samples taken during the co-expression of 4HBT, ACX4 and AcsA in *E. coli* BL21 (DE3) pLysS pET20b(+)::4HBT-ACX4-AcsA, as well as those taken during the expression of just ACX4 in *E. coli* BL21 (DE3) pLysS pET20b(+)::ACX4 and AcsA in *E. coli* BL21 (DE3) pLysS pET20b(+)::AcsA were analysed by sodium dodecylsulfate polyacrylamide gel electrophoresis (SDS-PAGE).

Analysis by SDS-PAGE (FIG. 9) showed that that when expression was performed at 37° C., at 5 h post induction, high levels of soluble 4HBT (left hand bottom band) and good levels of ACX4 (left hand top band) were detected with very little insoluble protein detected, though high levels of insoluble AcsA (right hand top band) were detected with no AcsA protein visible in the soluble fractions. Lane 1) Empty pET20b(+) vector negative control. 2) Spectra BR protein ladder. 3) pET20b(+)::4HBT-ACX4-AcsA expression 0 h soluble. 3) 3 h soluble. 4) 5 h soluble. 5) 0 h insoluble. 6) pET20b(+)::AcsA expression 5 h soluble. 7) pET20b(+):: ACX4 soluble. 8) pET20b(+)::4HBT soluble. 9) pET20b (+):4HBT-ACX4-AcsA 0 h insoluble. 10) pET20b(+): 4HBT-ACX4-AcsA 3 h insoluble. 11) pET20b(+):4HBT-ACX4-AcsA 5 h insoluble. 12) pET20b(+)::AcsA 5 h insoluble.

To test the ability of *E. coli* BL21 (DE3) pLysS pET20b (+)::4HBT-ACX4-AcsA to convert isobutyric acid to methacrylic acid, an MSX pre-culture (20 ml), supplemented with carbenicillin and chloramphenicol, was inoculated from a single colony of *E. coli* BL21 (DE3) pLysS pET20b (+)::4HBT-ACX4-AcsA on an LB agar plate supplemented with glucose carbenicillin and chloramphenicol, and was incubated at 37° C. with shaking at 200 rpm for 16 h. The cells were harvested by centrifugation at 5000 g for 15 min at 4° C., and the cells were re-suspended in MSX media (100 ml) supplemented with carbenicillin, chloramphenicol and riboflavin, in a 250 ml shake flask and this culture was incubated at 37° C. with shaking at 200 rpm. The co-expression of genes was induced with the addition of IPTG (0.4 mM) at an $OD_{600}$ of 0.5. The culture was incubated for a further 1 h prior to the addition of potassium isobutyrate (pH 7.0) from a concentrated stock concentration of 500 mM to a final concentration of 5 mM in the culture media. Samples were taken immediately after the addition of isobutyric acid (0 h sample) and then at 1 h, 2 h, 4 h, 6 h, 8 h and 19.5 h after that.

Samples taken throughout the biotransformation of isobutyric acid to methacrylic acid were centrifuged in an Eppendorf miniSpin F-45-12-11 rotor for 5 min at 6000 rpm. The supernatants were filtered through 0.2 μm Sartorius RC 4 mm filters and then acidified to pH2.5 with 5M HCl.

Acidified supernatant was injected onto an Agilent Zorbax Eclipse XDB C18 column (4.6 mm×150 mm). HPLC was performed at 0.4 ml·min$^{-1}$ and methacrylic acid was resolved from isobutyric acid by an isocratic elution with 14% acetonitrile in $KH_2PO_4$ that was adjusted to pH 2.5 with HCl. The column was washed between runs by increasing the flowrate to 1 ml·min$^{-1}$ and the acetonitrile concentration to 75% for 15 min before the conditions were returned to a flow-rate of 0.4 ml·min$^{-1}$ and 14% acetonitrile for the next sample. The column was allowed allowed to equilibrate for 20 min prior to the injection of next sample.

Three negative controls were also performed and analysed. The first control was the negative control strain, *E. coli* BL21 (DE3) pLysS pET20b(+), which did not contain the 4HBT-ACX4-AcsA co-expression operon and was cultured with no isobutyric acid added to the media after IPTG was added to culture media. The second control used the same strain as that used in the first control, but isobutyric acid (5 mM) was added 1 h after the addition of IPTG to the culture media. The third control used the same *E. coli* BL21 (DE3) pLysS pET20b(+)::4HBT-ACX4-AcsA as used in the main biotransformation culture, but no isobutyric acid was added to the culture media after the co-expression of 4HBT, ACX4 and AcsA was induced.

A summary of the HPLC traces observed in FIG. 10, which are traces of the samples taken at 20.5 hours post induction, from all four cultures that were tested (19.5 h biotransformation time). FIG. 10C is a standard of isobutyric acid (5 mM) and FIG. 10E is a standard of isobutyric acid (5 mM) mixed with a standard of methacrylic acid (200 μM). FIGS. 10A, 10B and 10D show that no methacrylic acid was formed in any of the controls and FIG. 10F shows that methacrylic acid was indeed formed during the biotransformation.

FIG. 11 summarises the production of methacrylic acid with time as well as growth of *E. coli* BL21 (DE3) pLysS pET20b(+)::4HBT-ACX4-AcsA during the biotransformation where the final concentration of the desired product of methacrylic acid is around 0.25 mM.

In this example, a whole cell process to convert isobutyric acid feedstock to methacrylic acid at industrially applicable levels has been demonstrated, by co-expressing 4HBT, ACX4 and AcsA in vitro in recombinant E. coli.

1.6 Example 4—Formation of Methacrylic Acid from Glucose

The branched chain keto acid dehydrogenase complex from *Pseudomonas putida* KT2440 was previously shown to catalyse the oxidative decarboxylation of 2-ketoisovaleric acid to isobutyryl-CoA in a recombinant metabolic pathway for the production of isobutyric acid in *E. coli* (Zhang, K., Xiong, M. and Woodruff, A. P. 2012, Cells and methods for producing isobutyric acid, International Patent Number WO 2012/109534 A2). The genes encoding the branched chain keto acid dehydrogenase alpha subunit (bkdA1), the branched chain keto acid dehydrogenase beta subunit (bkdA2), the lipoamide acyltransferase component (bkdB) and the lipoamide dehydrogenase component (IpdV) of the branched chain keto acid dehydrogenase complex are grouped adjacent to each other and are all found under the control of a single promoter in the *Pseudomonas putida* KT2440 genomic DNA (genbank accession number AE015451.1).

The entire wild-type sequence encoding bkdA1, bkdA2, bkdV and IpdV genes, as they appeared in the *Pseudomonas putida* KT2440 genomic DNA between nucleotides 4992042 and 4996988, was synthesised by Biomatik corporation as a single, ppBCKD, polynucleotide (SEQ. ID 14). The ppBCKD polynucleotide contained a XhoI restriction site at the 3' end, and a short sequence at the 5' end, immediately prior to the start codon of the bkdA1 gene. This 5' appended sequence contained an XbaI restriction site, a spacer sequence, an NheI restriction site, a ribosome binding site, and a second spacer sequence. The XbaI site was included to enable the insertion of the ppBCKD polynucleotide into the pET20b(+) plasmid for the construction of pET20b(+)::ppBCKD, capable of expressing just the four genes of the *Pseudomonas putida* KT2550 branched chain keto acid dehydrogenase. The first spacer sequence was included in order to maintain the same number of base-pairs between the T7 promoter and the ribosome binding site in the pET20b(+)::ppBCKD plasmid as exists in the pET20b (+) plasmid, and with the exception of the six nucleotides encoding the NheI site just prior to the ribosome binding site, the spacer sequence is identical to that between the XbaI site and the ribosome binding site in the pET20b(+) plasmid. The NheI restriction site was included to enable the insertion of the ppBCKD polynucleotide into the pET20b (+)::4HBT-ACX4 plasmid to construct the pET20b(+):: 4HBT-ACX4-ppBCKD plasmid. The ribosome binding site and the spacer sequence were identical to those used just prior to the bkdA1 gene when the BCKD genes were expressed for the production of isobutyric acid that was previously reported (Zhang, K., Xiong, M. and Woodruff, A. P. 2012, Cells and methods for producing isobutyric acid, International Patent Number WO 2012/109534 A2).

The single polynucleotide containing the four genes of the *Pseudomonas putida* KT2440 branched chain keto acid dehydrogenase was delivered in the pBSK plasmid (pBSK:: ppBCKD). The four genes were sub-cloned out of the pBSK::ppBCKD plasmid and into the pET20b(+)::4HBT-ACX4 plasmid from example 2, in between the NheI and XhoI restriction sites, to form pET20b(+)::4HBT-ACX4-ppBCKD (FIG. 12). Sequence ID 15 shows the sequence between the NdeI and XhoI restriction sites in the pET20b (+)::4HBT-ACX4-ppBCKD plasmid. The pET20b(+):: 4HBT-ACX4-ppBCKD plasmid was transformed into *E. coli* BL21 (DE3) pLysS to form *E. coli* BL21 (DE3) pLysS pET20b(+)::4HBT-ACX4-ppBCKD. Similarly, the four genes were also sub-cloned into the pET20b(+) plasmid between the NheI and XhoI restriction sites, forming pET20b(+)::ppBCKD, and this plasmid was transformed into *E. coli* BL21 (DE3) pLysS to form *E. coli* BL21 (DE3) pLysS pET20b(+)::ppBCKD. This latter strain was used to help identify bands on an SDS-PAGE gel corresponding to the bkdA1, bkdA2, bkdB and IpdV genes during expression studies (not shown).

An MSX pre-culture (10 ml) supplemented with carbenicillin and chloramphenicol was inoculated with *E. coli* BL21 (DE3) pLysS pET20b(+)::4HBT-ACX4-ppBCKD from a single colony on an LB agar plate supplemented with glucose, carbenicillin and chloramphenicol. Cultures were incubated at 37° C. with shaking at 250 rpm for 16 h. The cells were harvested by centrifugation at 5000 g for 15 min at 4° C. and then re-suspended in fresh MSX media (100 ml) which was supplemented with riboflavin as well as carbenicillin and chloramphenicol, in a 500 ml shake flask. The fresh cultures were incubated at 37° C. with shaking at 250 rpm and expression was induced in each culture at an $OD_{600}$ of 0.5 by the addition of IPTG (0.4 mM). The cultures were incubated for a further 17 h before samples were taken for analysis by reverse phase high performance liquid chromatography (RP-HPLC). A repeat culture was performed for the *E. coli* BL21 (DE3) pLysS pET20b(+) negative control culture.

Samples were centrifuged in an Eppendorf miniSpin F-45-12-11 rotor for 5 min at 6000 rpm. The supernatants were filtered through 0.2 micron Sartorius RC 4 mm filters and then acidified to pH2.5 with 5M HCl. Acidified supernatant was injected onto an Agilent Zorbax Eclipse XDB C18 column (4.6 mm×250 mm). HPLC was performed at 1 ml·min$^{-1}$ and analytes were eluted by isocratic elution with 14% acetonitrile in 50 mM $KH_2PO_4$ that was adjusted to pH 2.5 with HCl. The column was washed between runs by increasing the acetonitrile concentration to 75% for 15 min before being returned to 14% acetonitrile for a 20 min re-equilibration step.

Standards of methacrylic acid (0.2 mM), isobutyric acid (5 mM) and 2-ketoisovaleric acid (5 mM) eluted at 3.6 min, 8.3 min and 8.6 min, and with peak areas 5980 mAU·min, 330 mAU·min and 1580 mAU·min, respectively. The HPLC analysis of a cocktail of 2-ketoisovaleric acid (5 mM), isobutyric acid (5 mM) and methacrylic acid (200 μM) is shown in FIG. 13.

The HPLC analysis of the sample taken from the *E. coli* BL21 (DE3) pLysS pET20b(+) negative control culture, show in FIG. 14 showed no peaks in the region expected for methacrylic acid, whilst the analysis of the sample taken from the *E. coli* BL21 (DE3) pLysS pET20b(+)::4HBT-ACX4-ppBCKD culture showed a peak at 8.6 min with peak area 0.88 AU·min, corresponding to a methacrylic acid concentration of 0.11 mM (FIG. 15).

To confirm that the peak was indeed representative of methacrylic acid, the sample was spiked with an additional 0.24 mM of methacrylic acid from a 10 mM stock solution, and this spiked sample was also analysed by HPLC, show in FIG. 16. A single peak with an area of 2.7 AU·min, corresponding to a methacrylic acid concentration of 0.34 mM was observed at 8.5 min, corroborating that the *E. coli* BL21

(DE3) pLysS pET20b(+)::4HBT-ACX4-ppBCKD strain produces methacrylic acid directly from glucose.

To determine whether supplementing the cultures with 2-ketoisovaleric acid could boost methacrylic acid production, two MSX pre-cultures (10 ml) supplemented with carbenicillin and chloramphenicol were again prepared, inoculating one with E. coli BL21 (DE3) pLysS pET20b (+)::4HBT-ACX4-ppBCKD and the other with E. coli BL21 (DE3) pLysS pET20b(+) as before. The pre-cultures were incubated at 37° C. with shaking at 250 rpm for 16 h before the cells were pelleted and re-suspended in fresh MSX media (100 ml) supplemented with riboflavin, chloramphenicol and carbenicillin, in a 500 ml shake flask. Expression was induced in each culture at an $OD_{600}$ of 0.5 by the addition of IPTG (0.4 mM), and cultures were incubated for a further 3 h prior to the addition of 2-ketoisovalerate (pH 7.0) to a final concentration of 5 mM in each culture. The cultures were incubated for a further 14 h. Culture samples were taken and analysed by high performance liquid chromatography with isocratic elution as described for the cultures that were not supplemented with 2-ketoisovaleric acid.

The HPLC analysis of the sample taken 14 h after 2-ketoisovalerate was added to the empty E. coli BL21 (DE3) pLysS pET20b(+) negative control culture, shown in FIG. 17, showed no peaks in the region where methacrylic acid is usually observed, as expected. It did show, however, some background consumption of 2-ketoisovaleric acid (FIG. 6), with the peak area for this 2-ketoisovaleric acid in this culture being 3353 mAU·min, corresponding to 2.8 mM 2-Ketoisovaleric acid remaining in the culture as opposed to the original 5 mM.

When the sample taken 14 h after 2-ketoisovalerate was added to the culture expressing the genes for the conversion of 2-ketoisivaleric acid to methacrylic acid, the E. coli BL21 (DE3) pLysS pET20b(+)::4HBT-ACX4-ppBCKD culture, a peak at 8.4 min with peak area 1890 mAU·min appeared on the HPLC trace (FIG. 18), indicating that methacrylic acid was produced to a concentration of 0.24 mM. No 2-ketoisovaleric acid was detected in this sample, indicating that it was completely consumed during the conversion of 2-ketoisovaleric acid to methacrylic acid.

The sample was spiked with an additional 0.24 mM methacrylic acid and the analysis of the spiked sample (FIG. 19) showed a peak with peak area 3.4 AU·min, corresponding to methacrylic acid concentration of 0.44 mM, therefore the original methacrylic acid peak was genuine.

In this example, the branched chain keto acid dehydrogenase, namely BCKD from Pseudomonas putida KT2440, was co-expressed with an acyl-CoA oxidase, namely ACX4 from Arabidopsis thaliana, and a thioesterase enzyme, namely 4HBT from Arthrobacter sp. strain SU in a cellular system. It was demonstrated that production of methacrylic acid from a key feedstock like glucose which is readily available from biomass using recombinant E. coli is possible, and furthermore that production of said methacrylic acid can be boosted by supplementing the growth medium with 2-ketoisovaleric acid.

1.7 Example 5: The Whole Cell Production of Butyl Methacrylate from 2-Ketoisovalerate by Recombinant *Escherichia coli*

The ACX4 gene from A. thaliana was codon-optimized for E. coli, synthesized and cloned into pET16b (Sse) vector. The gene was digested with NheI/Sse8387I and ligated into pET16b (Sse) digested with XbaI/Sse8387I. The resultant plasmid, pMMA121 (see FIG. 20), was introduced into E. coli BL21(DE3), and the recombinant E. coli (BL21(DE3)/pMMA121) was cultured as follows; BL21(DE3)/pET16b (vector control) or BL21(DE3)/pMMA121 was inoculated LB medium supplemented with ampicillin (0.1 mg/ml) and grown overnight in a test tube at 37° C. An aliquot of an overnight culture was transferred to the 100 ml of the same medium in a flask and shaken at 37° C. for 2-3 hours. IPTG (final 1 mM) was added to the flask and the culture was incubated with shaking at 20° C. for overnight.

Cells were harvested by centrifuge and suspended in 0.1M sodium phosphate buffer (pH7.0), then disrupted by sonication. The disrupted E. coli cells were centrifuged to supernatant and pellet fractions, and both the vector control and the cells containing pMMA121 were analysed for ACO (acyl-CoA oxidase) activity (see FIG. 21) and expression of ACX4 protein by SDS-PAGE (see FIG. 22). FIG. 21 shows the presence of only IBA-CoA in the buffer, the presence of IBA-CoA and a small amount of CoA in the sample containing cells comprising only the unaltered plasmid pET16b, and the presence of MAA-CoA, much less IBA-CoA and an unknown compound in the sample containing cells comprising the plasmid pMMA121. Therefore, a high ACO activity was detected in the supernatant fraction of BL21/pMMA121 indicated by the production of methacrylyl CoA, showing that the 40 kDa protein detected by the SDS-PAGE of FIG. 22 is the ACX4 protein. The SDS-PAGE shows at lane 1—BL21/pET16b (vector) SF (soluble fraction); lane 2—BL21/pMMA121 SF; lane 3—BL21/pET16b IF (insoluble fraction); lane 4—BL21/pMMA121 IF; and lane 5—molecular weight marker. Around 40 kDa, a band (highlighted by black boxes) was observed only in the BL21/pMMA121 lanes but not in the BL21/pET16b (vector) lanes.

BCKAD complex gene was cloned from Pseudomonas aeruginosa PA01 strain as follows. DNA fragment containing an entire gene operon which encodes the BCKAD complex gene was obtained by PCR method with primers BCKAD.F and BCKAD.R (table in 1.1.3) using the genomic DNA as a template. The obtained fragment was digested with restriction enzymes BspHI and Sse8387I, and inserted to the vector pET16b(Sse) between NcoI/Sse8387I (BamH site of pET16b was converted to Sse8387I site). The resultant plasmid was named pWA008 (see FIG. 23).

A plasmid for expressing Apple AAT and A. thaliana ACX4 were constructed as follows. DNA fragments containing AAT or ACX4 gene was amplified by PCR method with primers AAT.F and AAT.R or ACX4.F and ACX4.R (table in 1.1.3), using a plasmid containing codon-optimized AAT gene or pMMA121 as a template, respectively. pET (Sse) vector was digested with restriction enzymes NcoI and Sse8387I and joined with the DNA fragment containing AAT gene, by using In-Fusion HD Cloning Kit (Takara Bio). The resultant plasmid, pAAT212, was digested with restriction enzyme SpeI and joined with the DNA fragment containing ACX4 gene, by using In-Fusion HD Cloning Kit. The resultant plasmid, pMMA133, contained AAT and ACX4 genes with T7 promoter control (see FIG. 23).

A plasmid for expressing BCKAD, AAT and ACX4 were constructed as follows. Plasmid pMMA133 was digested with restriction enzymes SpeI and Sse8387I, and the linearized DNA fragment was obtained. Plasmid pWA008 was digested with restriction enzymes XbaI and Sse8387I and the 5.0 kb fragment containing BCKAD complex gene was isolated. Both fragments were ligated using DNA Ligation Kit 'Mighty Mix' (manufactured by Takara Bio Inc.). The resultant plasmid pMMA134 (see FIG. 23) was introduced into E. coli BL21(DE3) for butyl methacrylate production experiments.

*E. coli* BL21(DE3)/pMMA134 was cultured in essentially the same manner as described above in relation to expression of ACX4. Cells were harvested by centrifuge, washed with 0.1M sodium phosphate buffer (pH7.0) and suspended in the same buffer to obtain cell suspension. By using the cell suspension, about 1 ml of a resting cell reaction solution was prepared in each vial, which contained 40 mM 2-ketoisovalerate (2-oxoisovalerate), 60 mM butanol, 0.05 M sodium phosphate buffer (pH7.0) and cells ($OD_{650}$=12.5). The reactions were carried out at 30° C., 180 rpm for 3 to 44 hours, and 1 ml acetonitrile was added to the vials and mixed well for stopping the reaction. After filtration using a syringe filter DISMIC/hole diameter 0.45 micron (manufactured by ADVANTEC), analysis was made by HPLC on ODS column. The HPLC conditions were as follows: Apparatus: Waters 2695, Column: CAPCELL PAK C18 UG120, 2.0 mm·D.×250 mm, Mobile phase: 0.1% phosphoric acid/65% methanol, Flow amount: 0.25 ml/min, Run time: 12 min, Column temperature: 35 C and Detection: UV 210 nm. FIG. 24 shows the concentration of the following chemicals over the time of the fermentation: ■, 2-ketoisovalerate (2-OIV); ▲, Isobutyric acid (IBA); ♦, Butyl methacrylate (BMA): and x, Methacrylic acid (MAA). As the concentration of the feedstock of 2-ketoisovalerate (2-oxoisovalerate) falls, the production of the intermediate in the pathway isobutyric acid, increases, as does the production of the final ester product butyl methacrylate.

This example demonstrates viable in vivo production of a derivative of methacrylic acid, the methacrylate ester butyl methacrylate, from the biochemical intermediate 2-ketoisovalerate (2-oxoisovalerate) which is produced directly from glucose, and the reagent butanol which is a common industrial feedstock. The production of butyl methacrylate is demonstrated at industrially applicably levels from culturing of recombinant *E. coli* cell expressing the BCKAD operon to convert 2-ketoisovalerate into isobutyryl CoA, ACX4 oxidase to convert isobutyryl coA into methacrylyl coA, and AAT to convert methacrylyl CoA into butyl methacrylate by reaction with butanol.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process of producing methacrylic acid and/or derivatives thereof comprising the following steps:
    (a) biologically converting isobutyryl-CoA into methacrylyl-CoA by action of an oxidase, the oxidase is an acyl-CoA oxidase that is ACX4 from *Arabidopsis thaliana*; and
    (b) converting methacrylyl-CoA into methacrylic acid and/or derivatives thereof.

2. The process according to claim 1, wherein step (b) is conducted biologically or chemically.

3. The process according to claim 1, wherein the derivatives thereof of methacrylic acid are methacrylic acid esters.

4. The process according to claim 1, wherein the methacrylic acid esters are butyl methacrylates.

5. The process according to claim 3, wherein the methacrylic acid esters are formed biologically by action of a transferase.

6. The process according to claim 5, wherein the transferase is an alcohol acyltransferase.

7. The process according to claim 6, wherein the alcohol acyltransferase is derived from a fruit origin.

8. The process according to claim 6, wherein the alcohol acyltransferase acts in the presence of an alcohol.

9. The process according to claim 1, wherein the process further comprises step (c) of converting methacrylic acid formed in step (b) into a methacrylic acid ester.

10. The process according to claim 9, wherein step (c) is conducted biologically or chemically.

11. The process according to claim 9, wherein step (c) is conducted biologically by action of an esterase or hydrolase.

12. The process according to claim 1, wherein methacrylyl-CoA is converted into methacrylic acid by the action of a thioesterase, transferase, synthetase, and/or a phosphotransacylase and a short chain fatty acid kinase.

13. The process according to claim 12, wherein methacrylyl-CoA is converted into methacrylic acid by action of a thioesterase.

14. The process according to claim 12, wherein methacrylyl-CoA is converted into methacrylic acid by action of a thioesterase and the thioesterase is acyl-CoA thioesterase 4HBT from *Arthrobacter* sp. Strain SU.

15. A process of producing methacrylic acid comprising the following steps:
(a) converting isobutyryl-CoA into methacrylyl-CoA by action of an oxidase, the oxidase is an acyl-CoA oxidase that is ACX4 from *Arabidopsis thaliana*; and
(b) biologically converting methacrylyl-CoA into methacrylic acid by the action of a thioesterase, transferase, synthetase, and/or a phosphotransacylase and a short chain fatty acid kinase.

16. A method of preparing polymers or copolymers of methacrylic acid or methacrylic acid esters, comprising the steps of:
(i) preparation of methacrylic acid and/or derivatives thereof in accordance with claim 1;
(ii) optional esterification of the methacrylic acid prepared in (i) to produce the methacrylic acid ester;
(iii) polymerization of the methacrylic acid and/or derivatives thereof prepared in (i) and/or, if present, the ester prepared in (ii), optionally with one or more comonomers, to produce polymers or copolymers thereof.

17. The method according to claim 16, wherein the derivatives thereof of methacrylic acid are methacrylic acid esters.

* * * * *

SEQUENCE LISTING

<160> NUMBER OF SEQ ID NOS: 24

<210> SEQ ID NO 1
<211> LENGTH: 471
<212> TYPE: DNA
<213> ORGANISM: Artificial Sequence
<220> FEATURE:
<223> OTHER INFORMATION: optimised 4-hydroxybenzoyl-coA thioesterase
      (4HBT) from Arthrobacter sp. strain SU

<400> SEQUENCE: 1

```
tatacatatg caccgtacct ctaacggttc tcacgcgacc ggtggtaacc tgccggatgt      60
tgcttctcat tacccggttg cgtacgaaca gaccctggac ggcaccgtgg gtttcgttat     120
cgacgaaatg accccggaac gtgcgaccgc gtctgttgaa gttaccgaca ccctgcgtca     180
gcgttggggt ctggttcacg gtggtgctta ctgcgcactg gcggagatgc tggcgaccga     240
agcgaccgtt gcggttgtgc acgaaaaggg tatgatggcg gttggccagt ctaaccacac     300
ctctttcttc cgtccggtta agaaggtca cgttcgcgcg gaagctgttc gcatccacgc     360
gggttctacc acctggttct gggacgtttc cctgcgcgat gatgcgggtc gcctgtgtgc     420
ggtgtcttct atgtctatcg cggtgcgtcc gcgtcgtgac taagcggccg c             471
```

<210> SEQ ID NO 2
<211> LENGTH: 36
<212> TYPE: DNA
<213> ORGANISM: Artificial Sequence
<220> FEATURE:
<223> OTHER INFORMATION: HHT.F forward primer for cloning of 4-HBT

```
<400> SEQUENCE: 2
tatacatatg caccgtacct ctaacggttc tcacgc                              36

<210> SEQ ID NO 3
<211> LENGTH: 24
<212> TYPE: DNA
<213> ORGANISM: Artificial Sequence
<220> FEATURE:
<223> OTHER INFORMATION: HHT.R reverse primer for cloning of 4HBT

<400> SEQUENCE: 3
ctcgagtccg tcacgacgcg gacg                                           24

<210> SEQ ID NO 4
<211> LENGTH: 469
<212> TYPE: DNA
<213> ORGANISM: Artificial Sequence
<220> FEATURE:
<223> OTHER INFORMATION: Product of the PCR performed to modify the 4HBT
      gene for sub cloning into the pET20b(+) plasmid to form the
      pET20b(+)::CtHis 4HBT plasmid.

<400> SEQUENCE: 4
tatacatatg caccgtacct ctaacggttc tcacgcgacc ggtggtaacc tgccggatgt    60
tgcttctcat tacccggttg cgtacgaaca gaccctggac ggcaccgtgg gtttcgttat   120
cgacgaaatg accccggaac gtgcgaccgc gtctgttgaa gttaccgaca ccctgcgtca   180
gcgttggggt ctggttcacg gtggtgctta ctgcgcactg gcggagatgc tggcgaccga   240
agcgaccgtt gcggttgtgc acgaaaaggg tatgatggcg gttggccagt ctaaccacac   300
ctctttcttc cgtccggtta agaaggtca cgttcgcgcg aagctgttc gcatccacgc    360 gggttctacc acctggttct gggacgtttc cctgcgcgat gatgcgggtc gcctgtgtgc   420
ggtgtcttct atgtctatcg cggtgcgtcc gcgtcgtgac ggactcgag               469

<210> SEQ ID NO 5
<211> LENGTH: 483
<212> TYPE: DNA
<213> ORGANISM: Artificial Sequence
<220> FEATURE:
<223> OTHER INFORMATION: carboxy-terminal hexahistidine tagged 4HBT in
      the pET20b(+)::CtHis-4HBT plasmid

<400> SEQUENCE: 5
atgcaccgta cctctaacgg ttctcacgcg accggtggta acctgccgga tgttgcttct    60
cattacccgg ttgcgtacga acagaccctg acggcaccg tgggtttcgt tatcgacgaa   120
atgaccccgg aacgtgcgac cgcgtctgtt gaagttaccg acaccctgcg tcagcgttgg   180
ggtctggttc acgtggtgc ttactgcgca ctggcgagaga tgctggcgac cgaagcgacc   240
gttgcggttg tgcacgaaaa gggtatgatg gcggttggcc agtctaacca cacctctttc   300
ttccgtccgg ttaaagaagg tcacgttcgc gcggaagctg ttcgcatcca cgcgggttct   360
accacctggt tctgggacgt ttccctgcgc gatgatgcgg gtcgcctgtg tgcggtgtct   420
tctatgtcta tcgcggtgcg tccgcgtcgt gacggactcg agcaccacca ccaccaccac   480
tga                                                                 483

<210> SEQ ID NO 6
<211> LENGTH: 1320
<212> TYPE: DNA
<213> ORGANISM: Artificial Sequence
<220> FEATURE:
```

<223> OTHER INFORMATION: optimised acyl-coA oxidase 4 (ACX4) from
      Arabidopsis thaliana

<400> SEQUENCE: 6

| | | | | | |
|---|---|---|---|---|---|
| catatggcag | ttctgagcag | cgcagatcgt | gcaagcaatg | aaaaaaaagt | gaaaagcagc | 60 |
| tatttcgacc | tgcctccgat | ggaaatgagc | gttgcatttc | gcaggcaac | accggcaagc | 120 |
| acctttccgc | cttgtaccag | cgattattat | cattttaatg | atctgctgac | ccctgaagaa | 180 |
| caggccattc | gtaaaaaagt | tcgtgagtgc | atggaaaaag | aagtggcacc | gattatgacc | 240 |
| gaatattggg | aaaaagcaga | attcccgttt | catattaccc | gaaactgggt | gcaatgggt | 300 |
| gttgccggtg | gtagcattaa | aggttatggt | tgtccgggtc | tgagcattac | cgcaaatgca | 360 |
| attgcaaccg | cagaaattgc | acgtgttgat | gcaagctgta | gcacctttat | tctggttcat | 420 |
| agcagcctgg | gtatgctgac | cattgcactg | tgtggtagcg | aagcacagaa | agaaaaatat | 480 |
| ctgccgagcc | tggcacagct | gaataccgtt | gcatgttggg | cactgaccga | accggataat | 540 |
| ggtagtgatg | caagcggtct | gggcaccacc | gcaaccaaag | ttgaaggtgg | ttggaaaatt | 600 |
| aacggtcaga | acgttggat | tggcaatagc | acctttgcag | atctgctgat | tatctttgca | 660 |
| cgtaatacca | ccaccaatca | gattaacggc | ttcatcgtta | aaaaagatgc | accgggtctg | 720 |
| aaagcaacca | aaattccgaa | caaaattggt | ctgcgtatgg | tgcagaatgg | tgatattctg | 780 |
| ctgcagaatg | tttttgtgcc | ggatgaagat | cgtctgcctg | tgttaatag | ctttcaggat | 840 |
| accagcaaag | ttctggcagt | tagccgtgtt | atggttgcat | ggcagccgat | tggtattagc | 900 |
| atgggtattt | atgatatgtg | ccaccgctat | ctgaaagaac | gtaaacagtt | tggtgcaccg | 960 |
| ctggcagcat | ttcagctgaa | tcagcagaaa | ctggttcaga | tgctgggtaa | tgttcaggca | 1020 |
| atgtttctga | tgggttggcg | tctgtgtaaa | ctgtatgaaa | ccggtcagat | gacaccgggt | 1080 |
| caggcaagcc | tgggtaaagc | atggattagc | agcaaagcac | gtgaaaccgc | cagcctgggt | 1140 |
| cgtgaactgc | tgggtggtaa | tggtattctg | gcagattttc | tggttgcaaa | agcatttgt | 1200 |
| gatctggaac | cgatctatac | ctatgaaggc | acctatgata | tcaataccct | ggttaccggt | 1260 |
| cgtgaagtta | ccggtattgc | aagctttaaa | ccggcaaccc | gtagccgtct | gtaactcgag | 1320 |

<210> SEQ ID NO 7
<211> LENGTH: 27
<212> TYPE: DNA
<213> ORGANISM: Artificial Sequence
<220> FEATURE:
<223> OTHER INFORMATION: OE.A.F forward primer for overlap extension
      polymerase chain reaction A

<400> SEQUENCE: 7
acatatgcac cgtacctcta acggttc                                         27

<210> SEQ ID NO 8
<211> LENGTH: 39
<212> TYPE: DNA
<213> ORGANISM: Artificial Sequence
<220> FEATURE:
<223> OTHER INFORMATION: OE.A.R reverse primer for overlap extension
      polymerisation chain reaction B

<400> SEQUENCE: 8
ctgccatatc tatatctcct gttagtcacg acgcggacg                            39

<210> SEQ ID NO 9
<211> LENGTH: 40
<212> TYPE: DNA

<213> ORGANISM: Artificial Sequence
<220> FEATURE:
<223> OTHER INFORMATION: OE.B.F forward primer for overlap extension
    polymerase chain reaction B

<400> SEQUENCE: 9
gtgactaaca ggagatatag atatggcagt tctgagcagc         40

<210> SEQ ID NO 10
<211> LENGTH: 40
<212> TYPE: DNA
<213> ORGANISM: Artificial Sequence
<220> FEATURE:
<223> OTHER INFORMATION: OE.B.R reverse primer for overlap polymerase
    chain reaction B

<400> SEQUENCE: 10
ctcgagatat tatagctagc ttacagacgg ctacgggttg         40

<210> SEQ ID NO 11
<211> LENGTH: 1805
<212> TYPE: DNA
<213> ORGANISM: Artificial Sequence
<220> FEATURE:
<223> OTHER INFORMATION: product of the overlap polymerase chain
    reaction to concatenate 4HBT and ACX4 into one polynucleotide

<400> SEQUENCE: 11

| | | |
|---|---|---|
| acatatgcac cgtacctcta acggttctca cgcgaccggt ggtaacctgc cggatgttgc | 60 |
| ttctcattac ccggttgcgt acgaacagac cctggacggc accgtgggtt tcgttatcga | 120 |
| cgaaatgacc ccggaacgtg cgaccgcgtc tgttgaagtt accgacaccc tgcgtcagcg | 180 |
| ttggggtctg gttcacggtg gtgcttactg cgcactggcg gagatgctgg cgaccgaagc | 240 |
| gaccgttgcg gttgtgcacg aaaagggtat gatggcggtt ggccagtcta accacacctc | 300 |
| tttcttccgt ccggttaaag aaggtcacgt tcgcgcggaa gctgttcgca tccacgcggg | 360 |
| ttctaccacc tggttctggg acgtttccct gcgcgatgat gcgggtcgcc tgtgtgcggt | 420 |
| gtcttctatg tctatcgcgg tgcgtccgcg tcgtgactaa caggagatat agatatggca | 480 |
| gttctgagca gcgcagatcg tgcaagcaat gaaaaaaaag tgaaaagcag ctatttcgac | 540 |
| ctgcctccga tggaaatgag cgttgcattt ccgcaggcaa caccggcaag caccttccg | 600 |
| ccttgtacca gcgattatta tcattttaat gatctgctga cccctgaaga acaggccatt | 660 |
| cgtaaaaaag ttcgtgagtg catggaaaaa gaagtggcac cgattatgac cgaatattgg | 720 |
| gaaaaagcag aattcccgtt tcatattacc ccgaaactgg tgcaatggg tgttgccggt | 780 |
| ggtagcatta aggttatgg ttgtccgggt ctgagcatta ccgcaaatgc aattgcaacc | 840 |
| gcagaaattg cacgtgttga tgcaagctgt agcacccttta ttctggttca tagcagcctg | 900 |
| ggtatgctga ccattgcact gtgtggtagc gaagcacaga agaaaaata tctgccgagc | 960 |
| ctggcacagc tgaataccgt tgcatgttgg gcactgaccg aaccggataa tggtagtgat | 1020 |
| gcaagcggtc tgggcaccac cgcaaccaaa gttgaaggtg gttggaaaat taacggtcag | 1080 |
| aaacgttgga ttgcaatag cacctttgca gatctgctga ttatctttgc acgtaatacc | 1140 |
| accaccaatc agattaacgg cttcatcgtt aaaaagatg caccgggtct gaaagcaacc | 1200 |
| aaaattccga acaaaattgg tctgcgtatg gtgcagaatg gtgatattct gctgcagaat | 1260 |
| gttttttgtgc cggatgaaga tcgtctgcct ggtgttaata gctttcagga taccagcaaa | 1320 |
| gttctggcag ttagccgtgt tatggttgca tggcagccga ttggtattag catgggtatt | 1380 |

| tatgatatgt gccaccgcta tctgaaagaa cgtaaacagt ttggtgcacc gctggcagca | 1440 |
| tttcagctga atcagcagaa actggttcag atgctgggta atgttcaggc aatgtttctg | 1500 |
| atgggttggc gtctgtgtaa actgtatgaa accggtcaga tgacaccggg tcaggcaagc | 1560 |
| ctgggtaaag catggattag cagcaaagca cgtgaaaccg ccagcctggg tcgtgaactg | 1620 |
| ctgggtggta atggtattct ggcagatttt ctggttgcaa aagcattttg tgatctggaa | 1680 |
| ccgatctata cctatgaagg cacctatgat atcaataccc tggttaccgg tcgtgaagtt | 1740 |
| accggtattg caagctttaa accggcaacc cgtagccgtc tgtaagctag ctataatatc | 1800 |
| tcgag | 1805 |

<210> SEQ ID NO 12
<211> LENGTH: 1663
<212> TYPE: DNA
<213> ORGANISM: Artificial Sequence
<220> FEATURE:
<223> OTHER INFORMATION: optimised acyl-CoA synthetase (acsA) from
      Pseudomonas chlororaphis B23

<400> SEQUENCE: 12

| gctagcagga gatatacata tgcgcgacta cgaacacgtt gtggaatctt tcgactacct | 60 |
| gcagagcgca acccaggacc tgcatggcga actgactgct ctgaacgcgt gtgtggagtg | 120 |
| ctgtgatcgt cacgcgcacg gcgaggctgt tgctctgtat tgcgaagcgc aggatggcca | 180 |
| cgcggaacgc taccgtttcc gcgatctgca gcgccaggct gcacgttttg caacttcct | 240 |
| gcgtgagcag ggcgtgaaac cgggcgaccg tgttgcgggc ctgatgccgc gtaccgtgga | 300 |
| actgctgatc gcaatcctgg gcacttggcg catcggtgcg gtttatcagc cgctgtttac | 360 |
| tgcgttcggt ccgaaagcaa ttgagcagcg tctgaactgt tctaacgcac gctggattgt | 420 |
| gaccgatccg cacaaccgcc cgaaactgga cgacgttacc gactgccgt ctattgtggt | 480 |
| taccggtggc gcaccgcaga acccggcaga ccatcactt tggtccgcac tgaaccgtca | 540 |
| ggcggatgac tgtgcgccgg tgctgctgga cgcatctgca ccgttcctgc tgatgtgcac | 600 |
| ctccggcacc actggtccgg caaagccgct ggaagttccg ctgtctgcga ttctggcatt | 660 |
| taaaggttac atgcgtgatg caatcgacct gcgcgctgat gatcgcttct ggaacctggc | 720 |
| agatccgggt tgggcatacg tctgtacta cgcggtgact ggcccgctgg cgtgtggcta | 780 |
| cgcgacctg ttttacgacg tccgttcac tgttgaatcc acccgtcaca tcatcgcgaa | 840 |
| atacgcgatt aacaacctgg cgggtagccc gaccgcttac cgctttctga ttgctgcagg | 900 |
| cgcggaattt gcggacgctg ttcgtggtcg tctgcgtgca gttagcagcg cgggtgaacc | 960 |
| gctgaacccg caggtggttc gttggtttgc tgaacagctg ggtgttgtta ccatgaccca | 1020 |
| ctatggtcag accgaaattg gtatggttct gtgcaaccac cacggcctgc gtcacccggt | 1080 |
| tcgcgagggt agcgctggct atgcagtgcc gggctatcgt atcgtggtgc tggataaagc | 1140 |
| acaccgtgag ctgccggctg gtcagccggg tgttctggcg gtggaccgtg aacgctcccc | 1200 |
| gctgtgctgg tttgacggct acctgggtat gccgactcag gcgttcgcgg tcgttatta | 1260 |
| cctgtctggt gatatcgttg aactgaacga cgatggcagc atctctttcg tgggtcgcaa | 1320 |
| cgatgatctg atcaccacct ctggttatcg tgtgggcccg ttcgacgttg agtctgcact | 1380 |
| gattgaacat ccggcagttg ttgaagctgc tgttatcggt aaaccggacc gcagcgtac | 1440 |
| tgagctgatt aaagcgtttg ttgttctgaa cactccgtac ctgccgagcc ggaactggc | 1500 |
| ggaagaactg cgtctgcatg ttcgtcagcg cctggctgcg cacgcatatc cgcgcgagat | 1560 |

| ggagtttgtg gaccatctgc cgaaaacccc gtctggcaaa ctgcagcgtt tcattctgcg | 1620 |
| taaccaggaa atcgctaagc agcaggctct gggttaactc gag | 1663 |

<210> SEQ ID NO 13
<211> LENGTH: 3447
<212> TYPE: DNA
<213> ORGANISM: Artificial Sequence
<220> FEATURE:
<223> OTHER INFORMATION: The sequence between, and inclusive of, the
      NdeI and XhoI restriction sites in pET20b(+)::4HBT ACX4 AcsA.

<400> SEQUENCE: 13

| catatgcacc gtacctctaa cggttctcac gcgaccggtg gtaacctgcc ggatgttgct | 60 |
| tctcattacc cggttgcgta cgaacagacc ctggacggca ccgtgggttt cgttatcgac | 120 |
| gaaatgaccc cggaacgtgc gaccgcgtct gttgaagtta ccgacaccct gcgtcagcgt | 180 |
| tggggtctgg ttcacggtgg tgcttactgc gcactggcgg agatgctggc gaccgaagcg | 240 |
| accgttgcgg ttgtgcacga aaagggtatg atggcggttg ccagtctaa ccacacctct | 300 |
| ttcttccgtc cggttaaaga aggtcacgtt cgcgcggaag ctgttcgcat ccacgcgggt | 360 |
| tctaccacct ggttctggga cgtttccctg cgcgatgatg cgggtcgcct gtgtgcggtg | 420 |
| tcttctatgt ctatcgcggt gcgtccgcgt cgtgactaac aggagatata gatatggcag | 480 |
| ttctgagcag cgcagatcgt gcaagcaatg aaaaaaagt gaaaagcagc tatttcgacc | 540 |
| tgcctccgat ggaaatgagc gttgcatttc gcaggcaac accggcaagc accttttccgc | 600 |
| cttgtaccag cgattattat cattttaatg atctgctgac ccctgaagaa caggccattc | 660 |
| gtaaaaaagt tcgtgagtgc atggaaaaag aagtggcacc gattatgacc gaatattggg | 720 |
| aaaaagcaga attcccgttt catattaccc cgaaactggg tgcaatgggt gttgccggtg | 780 |
| gtagcattaa aggttatggt tgtccgggtc tgagcattac cgcaaatgca attgcaaccg | 840 |
| cagaaattgc acgtgttgat gcaagctgta gcacctttat tctggttcat agcagcctgg | 900 |
| gtatgctgac cattgcactg tgtggtagcg aagcacagaa agaaaaatat ctgccgagcc | 960 |
| tggcacagct gaataccgtt gcatgttggg cactgaccga accggataat ggtagtgatg | 1020 |
| caagcggtct gggcaccacc gcaaccaaag ttgaaggtgg ttggaaaatt aacggtcaga | 1080 |
| aacgttggat tggcaatagc acctttgcag atctgctgat tatctttgca cgtaatacca | 1140 |
| ccaccaatca gattaacggc ttcatcgtta aaaaagatgc accgggtctg aaagcaacca | 1200 |
| aaattccgaa caaaattggt ctgcgtatgg tgcagaatgg tgatattctg ctgcagaatg | 1260 |
| tttttgtgcc ggatgaagat cgtctgcctg gtgttaatag ctttcaggat accagcaaag | 1320 |
| ttctggcagt tagccgtgtt atggttgcat ggcagccgat tggtattagc atgggtattt | 1380 |
| atgatatgtg ccaccgctat ctgaaagaac gtaaacagtt tggtgcaccg ctggcagcat | 1440 |
| ttcagctgaa tcagcagaaa ctggttcaga tgctgggtaa tgttcaggca atgtttctga | 1500 |
| tgggttggcg tctgtgtaaa ctgtatgaaa ccggtcagat gacaccgggt caggcaagcc | 1560 |
| tgggtaaagc atggattagc agcaaagcac gtgaaaccgc cagcctgggt cgtgaactgc | 1620 |
| tgggtggtaa tggtattctg gcagattttc tggttgcaaa agcatttgt gatctggaac | 1680 |
| cgatctatac ctatgaaggc acctatgata tcaataccct ggttaccggt cgtgaagtta | 1740 |
| ccggtattgc aagctttaaa ccggcaaccc gtagccgtct gtaagctagc aggagatata | 1800 |
| catatgcgcg actacgaaca cgttgtggaa tctttcgact acctgcagag cgcaacccag | 1860 |
| gacctgcatg gcgaactgac tgctctgaac gcgtgtgtgg agtgctgtga tcgtcacgcg | 1920 |

```
cacggcgagg ctgttgctct gtattgcgaa gcgcaggatg gccacgcgga acgctaccgt    1980
ttccgcgatc tgcagcgcca ggctgcacgt tttggcaact tcctgcgtga gcagggcgtg    2040
aaaccgggcg accgtgttgc gggcctgatg ccgcgtaccg tggaactgct gatcgcaatc    2100
ctgggcactt ggcgcatcgg tgcggtttat cagccgctgt ttactgcgtt cggtccgaaa    2160
gcaattgagc agcgtctgaa ctgttctaac gcacgctgga ttgtgaccga tccgcacaac    2220
cgcccgaaac tggacgacgt taccgactgc ccgtctattg tggttaccgg tggcgcaccg    2280
cagaacccgg cagaccatca cttttggtcc gcactgaacc gtcaggcgga tgactgtgcg    2340
ccggtgctgc tggacgcatc tgcaccgttc ctgctgatgt gcacctccgg caccactggt    2400
ccggcaaagc cgctggaagt tccgctgtct gcgattctgg catttaaagg ttacatgcgt    2460
gatgcaatcg acctgcgcgc tgatgatcgc ttctggaacc tggcagatcc gggttgggca    2520
tacggtctgt actacgcggt gactggcccg ctggcgtgtg gctacgcgac cctgttttac    2580
gacggtccgt tcactgttga atccacccgt cacatcatcg cgaaatacgc gattaacaac    2640
ctggcgggta gcccgaccgc ttaccgcttt ctgattgctg caggcgcgga atttgcggac    2700
gctgttcgtg gtcgtctgcg tgcagttagc agcgcgggtg aaccgctgaa cccgcaggtg    2760
gttcgttggt ttgctgaaca gctgggtgtt gttatccatg accactatgg tcagaccgaa    2820
attggtatgg ttctgtgcaa ccaccacggc ctgcgtcacc cggttcgcga gggtagcgct    2880
ggctatgcag tgccgggcta tcgtatcgtg gtgctggata agcacaccg tgagctgccg    2940 gctggtcagc cgggtgttct ggcggtggac cgtgaacgct ccccgctgtg ctggtttgac    3000
ggctacctgg gtatgccgac tcaggcgttc gcgggtcgtt attacctgtc tggtgatatc    3060
gttgaactga cgacgatgg cagcatctct ttcgtgggtc gcaacgatga tctgatcacc    3120
acctctggtt atcgtgtggg cccgttcgac gttgagtctg cactgattga acatccggca    3180
gttgttgaag ctgctgttat cggtaaaccg gacccgcagc gtactgagct gattaaagcg    3240
tttgttgttc tgaacactcc gtacctgccg agcccggaac tggcggaaga actgcgtctg    3300
catgttcgtc agcgcctggc tgcgcacgca tatccgcgcg agatggagtt tgtggaccat    3360
ctgccgaaaa ccccgtctgg caaactgcag cgtttcattc tgcgtaacca ggaaatcgct    3420
aagcagcagg ctctgggtta actcgag                                       3447
```

<210> SEQ ID NO 14
<211> LENGTH: 4996
<212> TYPE: DNA
<213> ORGANISM: Artificial Sequence
<220> FEATURE:
<223> OTHER INFORMATION: ppBCKD polynucleotide containing the four genes
      encoding the subunits of the Pseudomonas putida KT2440 branched
      chain keto acid dehydrogenase delivered in the pBSK::ppBCKD
      plasmid

<400> SEQUENCE: 14

```
tctagaaata attttgttta actgctagca ggagaaatta actatgaacg agtacgcccc      60
cctgcgtttg catgtgcccg agcccaccgg ccggccaggc tgccagaccg attttttcta     120
cctgcgcctc aacgatgcag gtcaagcccg taaacccgcg atcgatgtcg atgctgccga     180
cactgccgac ctgtcctaca gcctggtccg cgtgctcgac gagcaaggcg atgcgcaagg     240
cccctgggcc gaagacatcg acccgcagat cctccgtcaa ggcatgcgcg ccatgctcaa     300
gacgcggatc ttcgacagcc gcatggtggt tgcccagcgc cagaagaaga tgtccttcta     360
catgcaaagc ctgggcgaag aagccatcgg cagcggccag gcgctggcgc tgaaccgcac     420
```

-continued

```
cgacatgtgc ttcccgacct accgccagca aagcatcctg atggcccgcg acgtgtcgct    480
ggtcgagatg atctgccaac tgctgtccaa cgagcgcgac ccctcaagg gccgccagtt    540 gccgatcatg tattcggtgc gcgaagccgg cttcttcacc atcagcggca acctggcgac    600
ccagttcgtg caggcggtcg gctgggccat ggcatcggcg atcaagggcg ataccaagat    660
cgcctcggca tggatcggtg acggcgctac tgccgagtcg gacttccaca ccgcccttac    720
ctttgcccac gtataccgcg ccccggtcat cctcaacgtg gtcaacaacc aatgggccat    780
ttccaccttc caggccatcg ccggtggcga gtcgaccacc tttgccggcc gtggcgtggg    840
ttgcggtatt gcttcgctgc gggttgacgg caacgacttc gtcgccgtgt acgctgcctc    900
gcgctgggcg gccgagcgcg cccgccgcgg cctgggccca agcctgatcg agtgggtcac    960
ctaccgtgcc ggcccgcact cgacgtcgga cgacccctcc aagtaccgcc ctgccgacga   1020
ctggagccac ttcccgctgg gtgacccgat cgcccgcctg aagcagcacc tgatcaagat   1080
cggccactgg tccgaggaag aacaccaggc cgtcacggcc gagctcgaag ctgcggtgat   1140
tgccgcacag aaagaagccg agcagtacgg caccctggcc aacgggcaca tcccgagcgc   1200
cgcctcgatg ttcgaggatg tgtacaagga aatgcccgac cacctgcgcc gtcaacgcca   1260
ggaactgggg gtttgagatg aacgaccaca acaacagcat caacccggaa accgccatgg   1320
ccaccactac catgaccatg atccaggccc tgcgctcggc catggatgtc atgcttgagc   1380
gcgacgacaa tgtggtggtg tacggccagg acgtcggtta cttcggcggc gtgttccgct   1440
gcaccgaagg cctgcagaac aagtacggca atcgcgcgt gttcgacgcg cccatctccg   1500
agagcggcat cgtcggtacc gccgtgggca tgggtgccta tggcctgcgc ccggtggtgg   1560
agatccagtt cgccgactac ttctacccgg cctccgacca gatcgtctcc gagctggccc   1620
gcctgcgtta ccgttcggcc ggcgagttca ttgccccgct gaccctgcgc atgccttgcg   1680
gcggcggcat ctatggcggc cagactcaca gccagagccc ggaagcgatg ttcacccagg   1740
tgtgcggcct gcgcaccgtg atgccgtcca acccttatga cgccaaaggc ctgttgattg   1800
cctcgatcga atgcgacgac ccggtaatct tcctggagcc caaacgcctg tacaacggcc   1860
cgttcgatgg ccaccacgac cgccctgtaa ccccgtggtc gaagcacccg cacagcgccg   1920
tgcccgacgg ttattacacc gtaccgctgg acaaggccgc cattacccgc ctggcaatg   1980 acgtgaccgt gctgacctac ggcaccacgg tgtacgtggc ccaggtggcc gccgaagaaa   2040
gcggcgtcga tgccgaagtg atcgacctgc gcagcctgtg gccgctggac ctggacacta   2100
tcgtcgagtc ggtgaaaaag accggccgtt cgtggtggt gcacgaggcc acccgcacct   2160
gcggcttcgg tgccgagctg gtgtcgctgg tgcaggagca ctgcttccac cacctggagg   2220
cgccgatcga acgcgtcacc ggctgggaca cccccctaccc tcacgcacag gaatgggctt   2280
acttcccagg cccttcgcgg gtaggtgcgg cactgaaaaa ggtcatggag gtctgaatgg   2340
gcacgcacgt catcaagatg ccggacattg gcgaaggcat cgcgcaggtc gagttggtgg   2400
aatggttcgt caaggtcggc gacatcatcg ccgaggacca ggtggtggcc gacgtcatga   2460
ccgacaaggc caccgtggaa atcccctcgc cggtcagcgg caaggtgttg gccctgggtg   2520
gccagcccgg ggaagtgatg gcggtcggta gcgaactgat ccgcatcgaa gtggaaggca   2580
gcggcaacca tgtggatgtg cctcagccaa aaccggtaga ggccccggct gcccccattg   2640
cagccaagcc ggaaccgcag aaagacgtaa aacccgccgt gtaccaggcg cccgccaacc   2700
acgaagctgc gcccatcgtg ccgcgccagc cgggcgacaa gccgctggcc tcgcctgccg   2760
tgcgcaaacg cgccctggac gccggtatcg aactgcgtta tgtgcatggt agcggcccgg   2820
```

```
ccgggcgtat tctgcacgaa gacctcgatg ccttcatgag caagccgcaa agcaatgccg      2880
ggcaagcacc tgatggttat gccaagcgca ccgacagcga gcaggtgcca gtgatcggcc      2940
tgcgccgcaa gattgcccag cgcatgcagg acgccaaacg ccgggtcgcg cacttcagtt      3000
atgtcgagga aatcgacgtc accgccctgg aggccctgcg ccagcaactc aacagcaagc      3060
acggcgacag ccggggcaag ctgaccttgc tgccattcct ggtacgcgcc ctggtcgtgg      3120
cgctgcgtga cttcccgcag atcaacgcga cctacgatga cgaagcgcag atcatcaccc      3180
gccatggcgc ggtgcatgtg ggcattgcca cccaaggtga caacggcctg atggtgcccg      3240
tgctgcgcca cgccgaagcg ggcagcctgt gggccaatgc cggcgagatt tcgcgcctgg      3300
ccaacgctgc acgtaacaac aaggccagcc gtgaagagct gtccggctcg accatcaccc      3360
tgaccagcct tggcgccctg gtggcattgt cagcacgcc ggtggtcaac ccccggaag      3420 tggcaatcgt cggggtcaac cgcatggtcg aacggccagt ggtgatcgac ggccagatcg      3480
tcgtgcgcaa gatgatgaac ctgtccagct cgttcgacca ccgcgtggtc gatgcatgg      3540 atgccgccct gttcatccag gccgtacgtg gcctgctcga caacccgcc tgcctgttcg      3600 tggagtgagc atgcaacaga ttatccagac taccctgttg atcatcggcg gcggccctgg      3660
cggctatgta gcagccatcc gcgccgggca actgggcatt cctaccgtac tggtggaagg      3720
ccaggcactg gcggcacct gcctgaacat cggctgcatc ccgtccaagg cgctgatcca      3780
cgtggccgag cagtttcacc aggcctcgcg ctttaccgaa ccctcgccgc tgggcatcag      3840
cgtggcttcg ccgcgcctgg acatcggcca gagcgtcacc tggaaggacg gcattgtcga      3900
ccgcctgacc acaggtgttg ccgccctgct gaaaaagcac ggggtgaaag tggtgcatgg      3960
ttgggccaag gtactggacg gcaagcaggt cgaggtcgat ggccagcgta tccagtgcga      4020
gcatctgttg ctggcgaccg gttccagcag tgtcgaactg cctatgctgc cgctgggtgg      4080
cccggtgatt tcctcgaccg aagccctggc gccgaaaacc ctgccgcaac acctggtggt      4140
ggtcggcggt ggctatatcg gcctggagct gggcattgcc tatcgcaagc tgggtgcaca      4200
ggtgagtgtg gtggaagcgc gggagcgcat cctgccgacc tacgacagcg aattgaccgc      4260
cccggtggcc gagtcgctga agaaactggg catagcgttg cacctgggcc acagcgtcga      4320
gggctacgaa aatggctgcc tgctggccag cgacggcaag ggtgggcaac tgcgccttga      4380
ggccgaccag gtactggtgg ccgtgggacg ccggccacgc accaagggct caacctgga      4440 atgcctggac ctgaagatga acggcgccgc cattgccatc gacgagcgct gtcacaccag      4500
catgcacaac gtctgggcca tcggcgacgt cgctggcgaa ccgatgctgg cgcaccgggc      4560
catggcccag ggcgagatgg tcgccgaaat catcgccggc aaggcccgac gctttgaacc      4620
gacagcgatt gccgccgtgt gctttaccga cccggaagtg gtggtggtcg gcaagacccc      4680
ggaacaagcc agccagcagg gcctggactg catcgtcgcg cagttcccgt tgccgccaa      4740 tggccgggcc atgagcctgg aatcgaaaag cggtttcgtg cgggtggtgg cgcgccgtga      4800
caaccacctg atcgtgggtt ggcaggcggt tggcgtggcg gtctccgagc tatccaccgc      4860
gtttgcccaa tcgctggaga tgggcgcgtg cctggaagat gtggccggta ccattcatgc      4920
ccacccaacg ctcggtgaag cggtacagga agccgcactg cgcgcccggg ccacgcctt      4980 gcatatctga ctcgag                                                      4996
```

<210> SEQ ID NO 15
<211> LENGTH: 6758
<212> TYPE: DNA

<213> ORGANISM: Artificial Sequence
<220> FEATURE:
<223> OTHER INFORMATION: The sequence between, and inclusive of, the
    NdeI and XhoI restriction sites in the pET20b(+)::4HBT ACX4 ppBCKD
    plasmid

<400> SEQUENCE: 15

```
acatatgcac cgtacctcta acggttctca cgcgaccggt ggtaacctgc cggatgttgc      60
ttctcattac ccggttgcgt acgaacagac cctggacggc accgtgggtt tcgttatcga     120
cgaaatgacc ccggaacgtg cgaccgcgtc tgttgaagtt accgacaccc tgcgtcagcg     180
ttggggtctg gttcacggtg gtgcttactg cgcactggcg gagatgctgg cgaccgaagc     240
gaccgttgcg gttgtgcacg aaaagggtat gatggcggtt ggccagtcta accacacctc     300
tttcttccgt ccggttaaag aaggtcacgt tcgcgcggaa gctgttcgca tccacgcggg     360
ttctaccacc tggttctggg acgtttccct gcgcgatgat gcgggtcgcc tgtgtgcggt     420
gtcttctatg tctatcgcgg tgcgtccgcg tcgtgactaa caggagatat agatatggca     480
gttctgagca gcgcagatcg tgcaagcaat gaaaaaaaag tgaaaagcag ctatttcgac     540
ctgcctccga tggaaatgag cgttgcattt ccgcaggcaa caccggcaag cacctttccg     600
ccttgtacca gcgattatta tcattttaat gatctgctga ccctgaaga acaggccatt     660
cgtaaaaaag ttcgtgagtg catggaaaaa gaagtggcac cgattatgac cgaatattgg     720
gaaaaagcag aattcccgtt tcatattacc ccgaaactgg tgcaatggg tgttgccggt     780
ggtagcatta aaggttatgg ttgtccgggt ctgagcatta ccgcaaatgc aattgcaacc     840
gcagaaattg cacgtgttga tgcaagctgt agcaccttta ttctggttca tagcagcctg     900
ggtatgctga ccattgcact gtgtggtagc aagcacaga agaaaaata tctgccgagc     960
ctggcacagc tgaataccgt tgcatgttgg gcactgaccg aaccggataa tggtagtgat    1020
gcaagcggtc tgggcaccac cgcaaccaaa gttgaaggtg gttggaaaat taacggtcag    1080
aaacgttgga ttggcaatag caccttgca gatctgctga ttatctttgc acgtaatacc    1140
accaccaatc agattaacgg cttcatcgtt aaaaaagatg caccgggtct gaaagcaacc    1200
aaaattccga acaaaattgg tctgcgtatg gtgcagaatg gtgatattct gctgcagaat    1260
gttttttgtgc cggatgaaga tcgtctgcct ggtgttaata gctttcagga taccagcaaa    1320
gttctggcag ttagccgtgt tatggttgca tggcagccga ttggtattag catgggtatt    1380
tatgatatgt gccaccgcta tctgaaagaa cgtaaacagt ttggtgcacc gctggcagca    1440
tttcagctga atcagcagaa actggttcag atgctgggta atgttcaggc aatgtttctg    1500
atgggttggc gtctgtgtaa actgtatgaa accggtcaga tgacaccggg tcaggcaagc    1560
ctgggtaaag catggattag cagcaaagca cgtgaaaccg ccagcctggg tcgtgaactg    1620
ctgggtggta atggtattct ggcagatttt ctggttgcaa aagcattttg tgatctggaa    1680
ccgatctata cctatgaagg cacctatgat atcaataccc tggttaccgg tcgtgaagtt    1740
accggtattg caagctttaa accggcaacc cgtagccgtc tgtaagctag caggagaaat    1800
taactatgaa cgagtacgcc cccctgcgtt tgcatgtgcc cgagcccacc ggccggccag    1860
gctgccagac cgattttcc tacctgcgcc tcaacgatgc aggtcaagcc cgtaaacccg    1920
cgatcgatgt cgatgctgcc gacactgccg acctgtccta cagcctggtc cgcgtgctcg    1980
acgagcaagg cgatgcgcaa ggccctggg ccgaagacat cgaccgcag atcctccgtc    2040
aaggcatgcg cgccatgctc aagacgcgga tcttcgacag ccgcatggtg gttgcccagc    2100
gccagaagaa gatgtccttc tacatgcaaa gcctgggcga agaagccatc ggcagcggcc    2160
```

```
aggcgctggc gctgaaccgc accgacatgt gcttcccgac ctaccgccag caaagcatcc   2220
tgatggcccg cgacgtgtcg ctggtcgaga tgatctgcca actgctgtcc aacgagcgcg   2280
accccctcaa gggccgccag ttgccgatca tgtattcggt gcgcgaagcc ggcttcttca   2340
ccatcagcgc caacctggcg acccagttcg tgcaggcggt cggctgggcc atggcatcgg   2400
cgatcaaggg cgataccaag atcgcctcgg catggatcgg tgacggcgct actgccgagt   2460
cggacttcca caccgccctt accttttgccc acgtataccg cgccccggtc atcctcaacg   2520
tggtcaacaa ccaatgggcc atttccacct tccaggccat cgccggtggc gagtcgacca   2580
cctttgccgg ccgtggcgtg ggttgcggta ttgcttcgct gcgggttgac ggcaacgact   2640
tcgtcgccgt gtacgctgcc tcgcgctggg cggccgagcg cgcccgccgc ggcctgggcc   2700
caagcctgat cgagtgggtc acctaccgtg ccggcccgca ctcgacgtcg gacgacccct   2760
ccaagtaccg ccctgccgac gactggagcc acttcccgct gggtgacccg atcgcccgcc   2820
tgaagcagca cctgatcaag atcggccact ggtccgagga gaacaccag gccgtcacgg   2880
ccgagctcga agctgcggtg attgccgcac agaaagaagc cgagcagtac ggcaccctgg   2940
ccaacgggca catcccgagc gccgcctcga tgttcgagga tgtgtacaag gaaatgcccg   3000
accacctgcg ccgtcaacgc caggaactgg gggtttgaga tgaacgacca caacaacagc   3060
atcaacccgg aaaccgccat ggccaccact accatgacca tgatccaggc cctgcgctcg   3120
gccatggatg tcatgcttga gcgcgacgac aatgtggtgg tgtacggcca ggacgtcggt   3180
tacttcggcg gcgtgttccg ctgcaccgaa ggcctgcaga caagtacgg caaatcgcgc   3240
gtgttcgacg cgcccatctc cgagagcggc atcgtcggta ccgccgtggg catgggtgcc   3300
tatggcctgc gcccggtggt ggagatccag ttcgccgact acttctaccc ggcctccgac   3360
cagatcgtct ccgagctggc ccgcctgcgt taccgttcgg ccggcgagtt cattgccccg   3420
ctgaccctgc gcatgccttg cggcggcggc atctatggcg ccagactcca cagccagagc   3480
ccggaagcga tgttcaccca ggtgtgcggc ctgcgcaccg tgatgccgtc caacccttat   3540
gacgccaaag gcctgttgat tgcctcgatc gaatgcgacg accggtaat cttcctggag   3600
cccaaacgcc tgtacaacgg cccgttcgat ggccaccacc accgccctgt aaccccgtgg   3660
tcgaagcacc cgcacagcgc cgtgcccgac ggttattaca ccgtaccgct ggacaaggcc   3720
gccattaccc gccctggcaa tgacgtgacc gtgctgacct acggcaccac ggtgtacgtg   3780
gcccaggtgg ccgccgaaga aagcggcgtc gatgccgaag tgatcgacct gcgcagcctg   3840
tggccgctga acctggacac tatcgtcgag tcggtgaaaa agaccggccg ttgcgtggtg   3900
gtgcacgagg ccacccgcac ctgcggcttc ggtgccgagc tggtgtcgct ggtgcaggag   3960
cactgcttcc accacctgga ggcgccgatc gaacgcgtca ccggctggga cacccccttac   4020
cctcacgcac aggaatgggc ttacttccca ggcccttcgc gggtaggtgc ggcactgaaa   4080
aaggtcatgg aggtctgaat gggcacgcac gtcatcaaga tgccggacat ggcgaaggc   4140
atcgcgcagg tcgagttggt ggaatggttc gtcaaggtcg gcgacatcat cgccgaggac   4200
caggtggtgg ccgacgtcat gaccgacaag gccaccgtgg aaatccccct cgccggtcagc   4260
ggcaaggtgt tggccctggg tggccagccc ggggaagtga tggcggtcgg tagcgaactg   4320
atccgcatcg aagtggaagg cagcggcaac catgtggatg tgcctcagcc aaaaccggta   4380
gaggcccccg ctgcccccat tgcagccaag ccggaaccgc agaaagacgt aaacccgcc   4440
gtgtaccagg cgcccgccaa ccacgaagct gcgcccatcg tgccgcgcca gccgggcgac   4500
```

-continued

```
aagccgctgg cctcgcctgc cgtgcgcaaa cgcgccctgg acgccggtat cgaactgcgt    4560
tatgtgcatg gtagcggccc ggccgggcgt attctgcacg aagacctcga tgccttcatg    4620
agcaagccgc aaagcaatgc cgggcaagca cctgatggtt atgccaagcg caccgacagc    4680
gagcaggtgc cagtgatcgg cctgcgccgc aagattgccc agcgcatgca ggacgccaaa    4740
cgccgggtcg cgcacttcag ttatgtcgag gaaatcgacg tcaccgccct ggaggccctg    4800
cgccagcaac tcaacagcaa gcacggcgac agcggggca agctgacctt gctgccattc     4860
ctggtacgcg ccctggtcgt ggcgctgcgt gacttcccgc agatcaacgc gacctacgat    4920
gacgaagcgc agatcatcac ccgccatggc gcggtgcatg tgggcattgc cacccaaggt    4980
gacaacggcc tgatggtgcc cgtgctgcgc cacgccgaag cgggcagcct gtgggccaat    5040
gccggcgaga tttcgcgcct ggccaacgct gcacgtaaca caaggccag ccgtgaagag      5100 ctgtccggct cgaccatcac cctgaccagc cttggcgccc tgggtggcat tgtcagcacg    5160
ccggtggtca acaccccgga agtggcaatc gtcggggtca accgcatggt cgaacggcca    5220
gtggtgatcg acgccagat cgtcgtgcgc aagatgatga acctgtccag ctcgttcgac      5280
caccgcgtgg tcgatggcat ggatgccgcc ctgttcatcc aggccgtacg tggcctgctc    5340
gaacaacccg cctgcctgtt cgtggagtga gcatgcaaca gattatccag actaccctgt    5400
tgatcatcgg cggcggccct ggcggctatg tagcagccat ccgcgccggg caactgggca    5460
ttcctaccgt actggtggaa ggccaggcac tgggcggcac ctgcctgaac atcggctgca    5520
tcccgtccaa ggcgctgatc cacgtggccg agcagtttca ccaggcctcg cgctttaccg    5580
aaccctcgcc gctgggcatc agcgtggctt cgccgcgcct ggacatcggc cagagcgtca    5640
cctggaagga cggcattgtc gaccgcctga ccacaggtgt tgccgccctg ctgaaaaagc    5700
acggggtgaa agtggtgcat ggttgggcca aggtactgga cggcaagcag gtcgaggtcg    5760
atggccagcg tatccagtgc gagcatctgt tgctggcgac cggttccagc agtgtcgaac    5820
tgcctatgct gccgctgggt ggcccggtga tttcctcgac cgaagccctg cgccgaaaa     5880 ccctgccgca cacctggtg gtggtcggcg gtggctatat cggcctggag ctgggcattg      5940
cctatcgcaa gctgggtgca caggtgagtg tggtggaagc gcgggagcgc atcctgccga    6000
cctacgacag cgaattgacc gccccggtgg ccgagtcgct gaagaaactg ggcatagcgt    6060
tgcacctggg ccacagcgtc gagggctacg aaaatggctg cctgctggcc agcgacggca    6120
agggtgggca actgcgccctt gaggccgacc aggtactggt ggccgtggga cgccggccac    6180
gcaccaaggg cttcaacctg gaatgcctgg acctgaagat gaacggcgcc gccattgcca    6240
tcgacgagcg ctgtcacacc agcatgcaca acgtctgggc catcggcgac gtcgctggcg    6300
aaccgatgct ggcgcaccgg gccatggccc agggcgagat ggtcgccgaa atcatcgccg    6360
gcaaggcccg acgctttgaa ccgacagcga ttgccgccgt gtgctttacc gacccggaag    6420
tggtggtggt cggcaagacc ccggaacaag ccagccagca gggcctggac tgcatcgtcg    6480
cgcagttccc gtttgccgcc aatggccggg ccatgagcct ggaatcgaaa agcggtttcg    6540
tgcgggtggt ggcgcgccgt gacaaccacc tgatcgtggg ttggcaggcg gttggcgtgg    6600
cggtctccga gctatccacc gcgtttgccc aatcgctgga gatgggcgcg tgcctggaag    6660
atgtggccgg taccattcat gcccacccaa cgctcggtga agcggtacag gaagccgcac    6720
tgcgcgccct gggccacgcc ttgcatatct gactcgag                             6758
```

<210> SEQ ID NO 16
<211> LENGTH: 26

```
<212> TYPE: DNA
<213> ORGANISM: Artificial Sequence
<220> FEATURE:
<223> OTHER INFORMATION: BCKAD.F forward primer for cloning of BCKAD
      operon

<400> SEQUENCE: 16
ggcctgtcat gagtgattac gagccg                                        26

<210> SEQ ID NO 17
<211> LENGTH: 32
<212> TYPE: DNA
<213> ORGANISM: Artificial Sequence
<220> FEATURE:
<223> OTHER INFORMATION: BCKAD.R reverse primer for cloning of BCKAD
      operon

<400> SEQUENCE: 17
cggccctgca ggttcgcggg aatcagatgt gc                                 32

<210> SEQ ID NO 18
<211> LENGTH: 33
<212> TYPE: DNA
<213> ORGANISM: Artificial Sequence
<220> FEATURE:
<223> OTHER INFORMATION: AAT.F forward primer for cloning of AAT

<400> SEQUENCE: 18
aggagatata ccatgaaaag cttttctgta ctc                                33

<210> SEQ ID NO 19
<211> LENGTH: 44
<212> TYPE: DNA
<213> ORGANISM: Artificial Sequence
<220> FEATURE:
<223> OTHER INFORMATION: AAT.R reverse primer for cloning of AAT

<400> SEQUENCE: 19
agcagccgga tcccctgcag gactagttta ctggctggtg ctac                    44

<210> SEQ ID NO 20
<211> LENGTH: 39
<212> TYPE: DNA
<213> ORGANISM: Artificial Sequence
<220> FEATURE:
<223> OTHER INFORMATION: ACX4.F forward primer for cloning of ACX4

<400> SEQUENCE: 20
caccagccag taagctagca aggagatata ccatggctg                          39

<210> SEQ ID NO 21
<211> LENGTH: 37
<212> TYPE: DNA
<213> ORGANISM: Artificial Sequence
<220> FEATURE:
<223> OTHER INFORMATION: ACX4.R reverse primer for cloning of ACX4

<400> SEQUENCE: 21
tcccctgcag gactagttta caggcgagaa cgggtag                            37

<210> SEQ ID NO 22
<211> LENGTH: 5652
<212> TYPE: DNA
<213> ORGANISM: Artificial Sequence
<220> FEATURE:
<223> OTHER INFORMATION: pET16b(Sse) expression vector
```

<400> SEQUENCE: 22

```
ttcttgaaga cgaaagggcc tcgtgatacg cctattttta taggttaatg tcatgataat      60
aatggtttct tagacgtcag gtggcacttt tcggggaaat gtgcgcggaa cccctatttg     120
tttattttc taaatacatt caaatatgta tccgctcatg agacaataac cctgataaat     180
gcttcaataa tattgaaaaa ggaagagtat gagtattcaa catttccgtg tcgcccttat     240
tcccttttt gcggcatttt gccttcctgt ttttgctcac ccagaaacgc tggtgaaagt     300
aaaagatgct gaagatcagt tgggtgcacg agtgggttac atcgaactgg atctcaacag     360
cggtaagatc cttgagagtt ttcgccccga agaacgtttt ccaatgatga gcacttttaa     420
agttctgcta tgtggcgcgg tattatcccg tgttgacgcc gggcaagagc aactcggtcg     480
ccgcatacac tattctcaga atgacttggt tgagtactca ccagtcacag aaaagcatct     540
tacggatggc atgacagtaa gagaattatg cagtgctgcc ataaccatga gtgataacac     600
tgcggccaac ttacttctga caacgatcgg aggaccgaag gagctaaccg cttttttgca     660
caacatgggg gatcatgtaa ctcgccttga tcgttgggaa ccggagctga atgaagccat     720
accaaacgac gagcgtgaca ccacgatgcc tgcagcaatg gcaacaacgt tgcgcaaact     780
attaactggc gaactactta ctctagcttc ccggcaacaa ttaatagact ggatggaggc     840
ggataaagtt gcaggaccac ttctgcgctc ggcccttccg gctggctggt ttattgctga     900
taaatctgga gccggtgagc gtgggtctcg cggtatcatt gcagcactgg ggccagatgg     960
taagccctcc cgtatcgtag ttatctacac gacggggagt caggcaacta tggatgaacg    1020
aaatagacag atcgctgaga taggtgcctc actgattaag cattggtaac tgtcagacca    1080
agtttactca tatatacttt agattgattt aaaacttcat ttttaattta aaaggatcta    1140
ggtgaagatc cttttgata atctcatgac caaaatccct taacgtgagt tttcgttcca    1200
ctgagcgtca gaccccgtag aaaagatcaa aggatcttct tgagatcctt ttttttctgcg    1260
cgtaatctgt gcttgcaaa caaaaaaacc accgctacca gcggtggttt gtttgccgga    1320
tcaagagcta ccaactcttt ttccgaaggt aactggcttc agcagagcgc agataccaaa    1380
tactgtcctt ctagtgtagc cgtagttagg ccaccacttc aagaactctg tagcaccgcc    1440
tacatacctc gctctgctaa tcctgttacc agtggctgct gccagtggcg ataagtcgtg    1500
tcttaccggg ttggactcaa gacgatagtt accggataag gcgcagcggt cgggctgaac    1560
ggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggcctttt tacggttcct    1860
ggccttttgc tggccttttg ctcacatgtt ctttcctgcg ttatccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
```

```
tgtctgcctg ttcatccgcg tccagctcgt tgagtttctc cagaagcgtt aatgtctggc     2400
ttctgataaa gcgggccatg ttaagggcgg ttttttcctg tttggtcact gatgcctccg     2460
tgtaagggg atttctgttc atggggtaa tgataccgat gaaacgagag aggatgctca       2520
cgatacgggt tactgatgat gaacatgccc ggttactgga acgttgtgag ggtaaacaac     2580
tggcggtatg gatgcggcgg gaccagagaa aaatcactca gggtcaatgc cagcgcttcg     2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg    3120
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat    3360
aatggggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg cgacgatag tcatgccccg     3660
cgcccaccgg aaggagctga ctgggttgaa ggctctcaag gcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt   3840
gcgtattggg cgccagggtg ttttttcttt tcaccagtga cgggcaac agctgattgc     3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc   4080
gcattgcgcc cagcgccatc tgatcgttgg caaccagcat cgcagtggga acgatgccct   4140
cattcagcat ttgcatggtt tgttgaaaac cggacatggc actccagtcg ccttcccgtt   4200
ccgctatcgg ctgaatttga ttgcgagtga gatatttatg ccagccagcc agacgcagac   4260
gcgccgagac agaacttaat gggcccgcta acagcgcgat ttgctggtga cccaatgcga   4320
ccagatgctc cacgcccagt cgcgtaccgt cttcatggga gaaaataata ctgttgatgg   4380
gtgtctggtc agagacatca agaaataacg ccggaacatt agtgcaggca gcttccacag   4440
caatggcatc ctggtcatcc agcggatagt taatgatcag cccactgacg cgttgcgcga   4500
gaagattgtg caccgccgct ttacaggctt cgacgccgct tcgttctacc atcgacacca   4560
ccacgctgga acccagttga tcggcgcgag atttaatcgc cgcgacaatt tgcgacggcg   4620
cgtgcagggc cagactggag gtggcaacgc caatcagcaa cgactgtttg cccgccagtt   4680
```

```
gttgtgccac gcggttggga atgtaattca gctccgccat cgccgcttcc acttttccc    4740
gcgttttcgc agaaacgtgg ctggcctggt tcaccacgcg ggaaacggtc tgataagaga   4800
caccggcata ctctgcgaca tcgtataacg ttactggttt cacattcacc accctgaatt  4860
gactctcttc cgggcgctat catgccatac cgcgaaaggt tttgcgccat tcgatggtgt   4920
ccgggatctc gacgctctcc cttatgcgac tcctgcatta ggaagcagcc cagtagtagg   4980
ttgaggccgt tgagcaccgc cgccgcaagg aatggtgcat gcaaggagat ggcgcccaac   5040
agtccccgg ccacggggcc tgccaccata cccacgccga acaagcgct catgagcccg     5100
aagtggcgag cccgatcttc cccatcggtg atgtcggcga tataggcgcc agcaaccgca   5160
cctgtggcgc cggtgatgcc ggccacgatg cgtccggcgt agaggatcga gatctcgatc   5220
ccgcgaaatt aatacgactc actatagggg aattgtgagc ggataacaat tcccctctag   5280
aaataatttt gtttaacttt aagaaggaga tataccatgg cctgcagggg atccggctgc   5340
taacaaagcc cgaaaggaag ctgagttggc tgctgccacc gctgagcaat aactagcata   5400
acccccttggg gcctctaaac gggtcttgag gggtttttg ctgaaaggag gaactatatc   5460
cggatatccc gcaagaggcc cggcagtacc ggcataacca agcctatgcc tacagcatcc   5520
agggtgacgg tgccgaggat gacgatgagc gcattgttag atttcataca cggtgcctga   5580
ctgcgttagc aatttaactg tgataaacta ccgcattaaa gcttatcgat gataagctgt   5640
caaacatgag aa                                                      5652

<210> SEQ ID NO 23
<211> LENGTH: 1311
<212> TYPE: DNA
<213> ORGANISM: Artificial Sequence
<220> FEATURE:
<223> OTHER INFORMATION: optimised acyl-coA oxidase 4 (ACX4) from
      Arabidopsis thaliana for expression in pET16b (Sse)

<400> SEQUENCE: 23
atggctgtcc tgtcaagcgc tgaccgtgcg agcaatgaaa aaaagtgaa atcttcttac      60
ttcgatctgc cgccgatgga aatgtctgtt gcatttccgc aggcaacgcc ggcatcaacc    120
ttcccgccgt gcacgtcgga ttattaccat tttaacgacc tgctgacccc ggaagaacag    180
gccattcgta aaaagttcg cgaatgtatg gaaaaagaag tcgcaccgat tatgaccgaa    240
tattgggaaa aagcggaatt ccgttccac attaccccga actgggtgc gatgggtgtg    300
gccggcggta gtatcaaagg ctacggttgc ccgggtctgt ccattacggc aaatgctatc   360
gcgaccgccg aaattgcacg tgtggatgct tcatgctcga cgttcatcct ggttcatagc   420
tctctgggta tgctgaccat tgcgctgtgt ggctcagaag cccagaaaga aaaatatctg   480
ccgtcgctgg cgcaactgaa cacggtcgca tgttgggctc tgaccgaacc ggataatggc   540
agcgacgcat ctggcctggg taccacggct accaaagtgg aaggcggttg aaaatcaac    600
ggtcagaaac gttggattgg caatagtacc tttgcggatc tgctgattat cttcgcccgc   660
aacaccacga ccaaccagat caacggtttc atcgtcaaaa aagacgcacc gggcctgaaa   720
gctaccaaaa ttccgaataa atccggtctg cgcatggtgc agaacggcga tattctgctg   780
caaaatgtgt tgttccgga tgaagaccgt ctgccgggtg ttaacagttt ccaggacacc   840
agcaaagttc tggcagtcag ccgcgtcatg gtggcttggc aaccgattgg catctctatg   900
ggtatctatg atatgtgcca ccgttacctg aaagaacgta aacagtttgg tgcaccgctg   960
gcagcattcc aactgaacca gcaaaaactg gtccagatgc tgggtaatgt gcaagcaatg  1020
```

-continued

```
tttctgatgg gctggcgtct gtgtaaactg tatgaaacgg gtcagatgac cccgggtcaa    1080
gcaagcctgg gcaaagcctg gattagttcc aaagcgcgtg aaaccgcaag cctgggtcgt    1140
gaactgctgg gcggtaacgg catcctggcc gattttctgg ttgcaaaagc tttctgcgac    1200
ctggaaccga tctatacgta cgaaggtacc tacgatatta atacgctggt gaccggtcgc    1260
gaagttacgg gcattgcaag cttcaaaccg gctacccgtt ctcgcctgta a             1311
```

<210> SEQ ID NO 24
<211> LENGTH: 1368
<212> TYPE: DNA
<213> ORGANISM: Artificial Sequence
<220> FEATURE:
<223> OTHER INFORMATION: optimised alcohol acyl transferase (AAT) from Apple for expression in pET16b(Sse)

<400> SEQUENCE: 24

```
atgaaaagct tttctgtact ccaagtcaaa cgcctgcaac cagaactgat tacgccagcg     60
aaatcgaccc gcaggaaac caaattcctg tctgacatcg atgaccaaga gagcttgcgt    120
gtgcagattc cgatcatcat gtgctataaa gacaacccga gcctgaataa gaatcgcaat    180
ccggttaagg ccattcgtga ggccctgtcc cgtgcgctgg tttactatta cccgctggcg    240
ggtcgtctgc gtgagggtcc gaatcgcaaa ctggtggtgg actgcaatgg tgagggtatt    300
ctgtttgttg aggcgagcgc ggacgtcacc ctggaacagc tgggcgacaa gatcctgccg    360
ccgtgtccgc tgttggaaga gttctgtac aacttcccgg gcagcgatgg tatcatcgat    420
tgcccgctgc tgctgattca agtcacttgt ctgacgtgtg gtggctttat tctggctctg    480
cgcctgaacc acaccatgtg tgatgcagcg ggtttgttgc tgttcctgac cgccatcgca    540
gagatggccc gtggtgccca cgcaccgagc attctgccgg tgtgggaacg tgaactgctg    600
ttcgcacgtg acccgcctcg tattacttgc gcgcaccatg aatacgagga cgttatcggc    660
catagcgacg gcagctacgc gagcagcaac caaagcaata tggtgcagcg tagcttttac    720
ttcggcgcga agaaatgcg tgttctgcgc aagcagatcc cgcctcacct gatcagcacg    780
tgcagcacct ttgatttgat taccgcatgc ctgtggaagt gccgtacgct ggcgctgaac    840
atcaacccga aagaagccgt ccgtgtgagc tgtatcgtta acgcgcgtgg taaacacaac    900
aatgttcgcc tgccgctggg ctattacggc aatgcgttcg cattcccggc tgctatctct    960
aaggcagagc cgctgtgtaa gaaccctctg ggttacgccc tggagttggt gaagaaggcg    1020
aaagcgacca tgaatgaaga gtatctgcgc agcgtggcgg atctgctggt ttgcgcggt    1080 cgtccgcaat actccagcac gggttcctat ctgattgtga gcgacaatac ccgcgtgggt    1140
tttggtgatg tcaacttcgg ttggggccag ccagtctttg ctggcccggt caaagcattg    1200
gacctgatta gcttctatgt tcaacataag aacaacacgg aagatggtat cttggttccg    1260
atgtgcctgc cgtcctcggc gatggagcgt ttccaacagg agctggagcg cattacccag    1320
gaaccgaaag aggatatttg caacaatctg cgtagcacca gccagtaa               1368
```